(12) United States Patent
Lohse

(10) Patent No.: US 9,091,691 B2
(45) Date of Patent: *Jul. 28, 2015

(54) IMMUNOCHEMICAL DETECTION OF SINGLE TARGET ENTITIES

(75) Inventor: Jesper Lohse, Herlev (DK)

(73) Assignee: Dako Denmark A/S, Glostrup (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/502,727

(22) PCT Filed: Oct. 15, 2010

(86) PCT No.: PCT/DK2010/000137
§ 371 (c)(1),
(2), (4) Date: Jul. 9, 2012

(87) PCT Pub. No.: WO2011/047680
PCT Pub. Date: Apr. 28, 2011

(65) Prior Publication Data
US 2012/0270242 A1    Oct. 25, 2012

Related U.S. Application Data

(60) Provisional application No. 61/253,116, filed on Oct. 20, 2009.

(51) Int. Cl.
*G01N 33/535* (2006.01)
*C12Q 1/28* (2006.01)
*G01N 33/53* (2006.01)
*G01N 33/58* (2006.01)
*G01N 33/543* (2006.01)

(52) U.S. Cl.
CPC ........ *G01N 33/581* (2013.01); *G01N 33/54306* (2013.01)

(58) Field of Classification Search
CPC . G01N 33/581; G01N 33/54393; C12Q 1/28; C08G 63/672
See application file for complete search history.

(56) References Cited

U.S. PATENT DOCUMENTS

| | | | |
|---|---|---|---|
| 5,804,404 A * | 9/1998 | Heras et al. | 435/28 |
| 6,723,524 B1 * | 4/2004 | Hermens et al. | 435/7.92 |
| 6,767,716 B2 | 7/2004 | Giri | |

FOREIGN PATENT DOCUMENTS

WO    WO 2007/015168 A2    2/2007

OTHER PUBLICATIONS

International Search Report issued in PCT/DK2010/000137 by the International Searching Authority of the European Patent Office; Date of Mailing: Jan. 28, 2011.
Takei et al., "Regulation of Enzyme-Substrate Complexation by a Substrate Conjugated with a Phospholipid Polymer" *Biomacromolecules*, 5:585-862 (2004).
Uchihara et al., "Dual enhancement of double immunofluorescent signals by CARD: participation of ubiquitin during formation of neurofibrillary tangles" *Histochem. Cell Biol.*, 114:447-451 (2000).

* cited by examiner

*Primary Examiner* — Shafiqul Haq

(57) ABSTRACT

The present invention relates to immunochemical visualization and quantification of single target entities, such as single molecules, single molecular structures, single particles, etc. in samples wherein said single entities are immobilized. In particular, the invention relates to methods for visualization and quantification of single units of biological or chemical targets, in particular to immunochemical visualization of single molecules of biological targets in histological samples. The methods of the invention comprise a step of forming discrete deposits of detectable molecules at single target sites of sample mediated by an enzyme with oxydoreductase activity, wherein a single target site comprises a single unit of a target. The invention also relates to assays comprising the present visualization and quantification methods and diagnostic applications of said methods.

30 Claims, 3 Drawing Sheets

IMMUNOCHEMICAL DETECTION OF SINGLE TARGET ENTITIES

CROSS-REFERENCE TO RELATED APPLICATIONS

This application is a U.S. national stage entry under 35 U.S.C. §371 of International Application No. PCT/DK2010/000137, filed Oct. 15, 2010, which claims priority to U.S. Provisional Application No. 61/253,116, filed Oct. 20, 2009, both of which are incorporated herein by reference.

FIELD OF THE INVENTION

The present invention lies in the field of immunochemical visualization and quantification of single target entities, such as single molecules, single molecular structures, single particles, etc. in samples wherein said single entities are immobilized. In particular, the invention relates to methods for visualization and quantification of single units of biological or chemical targets, in particular to immunochemical visualization of single molecules of biological targets in histological samples. The methods of the invention comprise a step of forming discrete deposits of detectable molecules at single target sites of sample mediated by an enzyme with oxydoreductase activity, wherein a single target site comprises a single unit of a target.

BACKGROUND OF THE INVENTION

Immunochemistry is a common tool in medical diagnostics and it is also usual for the assessment of therapeutic biomarkers. The latter, in particular, often require a quantitative evaluation of the extent of their presence. The application of antibodies to cells and tissues presents specific difficulties beyond those encountered when these reagents are applied to purified proteins immobilized onto solid supports in or solution. There are many factors that can affect immunodetection, among these fixation and preparation of tissue, duration and type of antigen retrieval and antibody specificity. An additional difficulty is the ability to detect targets present at low levels. In common with soluble assays, this becomes a matter of increasing signal without raising the level of nonspecific background. The approach that has been most commonly explored is signal amplification, which is achieved by successive rounds of enzymatic reactions.

DAB is a chromogeninc substrate of horse radish peroxidase (HRP) that is widely used for visualizing of target proteins in histological samples which are labeled with peroxidase activity. The method utilizes that HRP linked to antibodies targeted to proteins of a sample deposits DAB from a solution to the sites of targeted proteins and thereby labels the proteins. The method is not especially sensitive and therefore suitable for detection of relatively abundant target proteins. The signal associated with DAB deposits cannot be further amplified. Other drawbacks to mention are that the method demands rather high amounts of target specific antibodies to saturate all target sites and it is relatively slow. Furthermore, the method provides a uniform staining pattern that appears to the microscopist as a homogeneous color with intracellular resolution of cellular structures, e.g. membrane, cytoplasm, and nucleus, which makes it impossible to quantify the staining accurately.

Catalyzed signal amplification (CSA) (described in U.S. Pat. Nos. 5,863,748; 5,688,966; 5,767,267; 5,721,158; 5,583,001; 5,196,306; 6,372,937; 6,593,100; U.S. Pat. No. 6,593,100) adopted biotinyl- and fluorescyl-tyramide to increase the signal from HRP labeled target proteins and allowed thus detection of low abundance targets that are otherwise undetectable by the conventional method (i.e. above method). However, due to a strong background staining and difficult interpretation of the results of staining, in particular of Fluorescent in-situ hybridization (FISH) and immunohistochemistry (IHC) samples, CSA has never been widely accepted as a routine approach for evaluation of histological samples in clinical histopathology.

Recently, it has been described another HRP-based amplification method allowing detection of low abundance target molecules in IHC samples (described in WO2009036760, WO2010094283 and WO2010094284). The method utilizes DAB not as a chromogenic substrate of HRP, but as a cross-linking agent which mediates deposition of other detectable HRP substrates by HRP. The method provides for a strong amplification of a signal of the deposited HRP substrate, which makes the sensitivity of the method to be comparable with the CSA method, but compared to the latter method the new method advantageously provides no background labeling. Among other advantages of this new method it is worth to mention that the speed of the detection procedure is much faster than either the traditional DAB or biotinyl-tyramide detection procedure. However, the problem of the previous methods, namely assessment of quantity of the target in IHC samples that is based on the assessment of the quantity of detected stain, has not been solved. The new method provides a staining pattern which is very crisp, but is the same uniform staining with intracellular resolution of cellular structures as of the traditional DAB methods or CSA method. This stain pattern does not allow direct approximating the quantity of the target to the quantity of the stain in a sample, because the correlation between these two quantities is not linear. Accordingly, the quantity of a target in a histological sample visualized by all these methods can only be assessed relatively, not precisely.

Thus, whilst quality assurance schemes for the methodology have been improved and raised the standards of IHC staining, the schemes that relate to interpretation of the staining results have not been changed. Different scoring systems using varying cut-off levels for assessing whether a tissue is "positive" or "negative" are normally used for assessment of antigens. Such currently used assessment is inevitably associated with errors which may be of crucial importance in medical diagnostic.

Assessment of target expression based of evaluation of the precise quantity of individual target molecules present in samples, so called single molecule detection (SMD) approach, could be a way to a new scoring system in IHC that would be more reliable and reputable for both medical diagnostics and therapy. Unfortunately, the number of available techniques allowing visualizing single molecules of target proteins in histological samples is presently very limited and they are rather laborious and long procedures.

Basically, all the available single protein molecule detection techniques use DNA-based amplification systems Single protein molecule detection was first demonstrated with the advent of immuno-PCR (Sano T, Smith C L, Cantor C R. Immuno-PCR: very sensitive antigen detection by means of specific antibody-DNA conjugates. Science 1992; 258:120-122; Adler M, Wacker R, Niemeyer C M. A real-time immuno-PCR assay for routine ultrasensitive quantification of proteins. Biochem Biophys Res Commun 2003; 308:240-250; Niemeyer C M, Adler M, Wacker R. Immuno-PCR: high sensitivity detection of proteins by nucleic acid amplification. Trends Biotechnol 2005; 23:208-216). Using antibody-DNA hybrid constructs, the antibody's binding affinity was complemented by the sensitive detection achievable with PCR. In addition, immuno-DNA detection strategies have been extended to use rolling circle amplification (RCA), an isothermal technique that generates a long ssDNA oligomer tethered to the immuno-DNA conjugate. (Gusev Y, Sparkowski J, Raghunathan A, Ferguson H Jr, Montano J, Bogdan N, Schweitzer B, Wiltshire S, Kingsmore S F, Maltzman W, Wheeler V. Rolling circle amplification: a new approach to increase sensitivity for immunohistochemistry and flow cytometry. Am J Pathol 2001; 159:63-69).

Some of the substantial drawbacks of these SMD approaches to mention are that
  (i) synthesis of the antibody-DNA hybrids can be problematic as controlling the location and number of DNA conjugates per protein is not always straightforward, often leading to heterogeneous ratios of DNA tags per antibody; amplification reaction is difficult to control; amplification step is temperature sensitive; labeling is not stable-the label will defuse from the target over time; etc. Despite of recent developments in site-specific conjugation of oligonucleotide tags to proteins using intein chemistry (or chemical ligation) have been very successful, conjugate preparation still remains laborious;
  (ii) steps of the methods require the temperature control;
  (iii) detection procedures comprise too many steps; and
  (iv) the whole process of detection takes a relatively long time.

The SMD approach of the present invention overcomes the above obstacles and makes visualization and quantification of single entities of targets in samples wherein said single entities are immobilized simple and reliable.

SUMMARY OF THE INVENTION

This invention provides rapid, simple and robust methods for visualization, detection and quantification of single entities a variety of targets in different samples, wherein the targets are immobilized. The methods are particular advantageous for evaluation of complex biological samples, such as histological samples.

Methods of the invention comprises a novel powerful signal amplification system that makes possible visualizing individual single entities of targets, such as single molecules, single molecular structures, single molecular complexes, single particles etc., in a very wide dynamic concentration range in a host variety of samples. The term "single entity of target" is interchangeably used herein with the term "single/individual unit of target".

The methods of the invention comprise steps of:
a) forming in a sample one or more target sites labeled with enzymatic activity, wherein each of said target sites comprise a single unit of a target, wherein said target sites are formed with a fractional sub-population of the total amount of single target units of the sample; and
b) forming discrete deposits of detectable molecules (also termed herein "reporter molecules" or "reporter") at each single target site.

In some embodiments, the step (a) as above may be redundant as the sample may already comprise target sites according to the invention.

In other embodiments, methods of the invention may comprises one or more further steps, e.g.
c) detecting the discrete deposits of reporter molecules at the single target sites as visually distinct dots.

In one embodiment the invention relates to a method (method (1)) for visualization of individual single units of a target in a sample, wherein said target is immobilized, comprising
  a) Incubating a sample comprising a population of individual units of a target with of one or more binding agents, wherein
    (1) at least one of the binding agents comprises an enzyme;
    (2) at least one of the binding agents is capable of directly binding to an individual single unit of the target,
    and forming one or more discrete single target sites a fractional sub-population of individual single units of the target, wherein each single discrete single target site comprises a complex of one individual single unit of said fractional sub-population and one or more binding agents, at least one thereof comprising the enzyme;
  a) incubating a sample of (a) in an aqueous solution (i) comprising a peroxide compound in an amount that is less than 2 mM,
    a first substrate of the enzyme associated with discrete single target sites of (a) and,
    a second substrate of said enzyme,
  wherein said first substrate is a water soluble electron rich organic compound which is
    (1) capable of generating a radical upon a reaction with said enzyme; and
    (2) capable of cross-linking molecules of said second substrate in the presence of both said enzyme and a peroxide compound, thereby producing a water insoluble polymeric product of said second substrate,
  and wherein said second substrate is a conjugate molecule comprising at least two compounds that are capable of serving as substrates of said enzyme and a detectable label, wherein the detectable label is selected from the group consisting of a fluorescent, luminescent, radioactive or chromogenic matter and a member of a specific binding pair,
  thereby forming discrete deposits of the second substrate at discrete single target sites of (a) and visualizing said single target sites of (a)

A method of the invention comprising steps (a) and (b) as above may further comprise one or more steps of detection of discrete deposits at single target sites.

In one embodiment the method (1) of above may be used for detection and visualization of single individual units of an immobilized target in a sample, wherein the target is present in a broad dynamic concentration range, which comprises the following steps:
  a) incubating the sample with one or more binding agents, wherein
    (1) at least one of the binding agents comprises an enzyme;
    (2) at least one of the binding agents is capable of directly binding to an individual single unit of the target,
    and forming one or more discrete first target sites with a first fractional sub-population of individual single units of the target, wherein each single discrete first target site comprises a complex of one individual single unit of said first fractional sub-population of individual single units and one or more binding agents, at least one thereof comprising the enzyme with oxidoreductase activity;
  b) incubating the sample of (a) with a first substrate of the enzyme associated with the first target sites of (a), a first population of molecules of second substrate said enzyme and a peroxide compound according to step (b)

of claim 1, thereby forming discrete deposits of molecules of second substrate of the first population at the first target sites of (a);
c) incubating the sample of (b) with a solution hydrogen peroxide in an amount sufficient to quench the residual activity of the associated with the first single target sites of (a);
d) incubating the sample (c) with one or more binding agents, wherein
  (1) at least one of the binding agents comprises an enzyme;
  (2) at least one of the binding agents is capable of directly binding to an individual unit of the target,
thereby forming one or more discrete second target sites with a second fractional sub-population of individual single units of the target, wherein each single discrete second target site comprises a complex of one individual unit of said second fractional sub-population of individual single units and one or more binding agents, at least one thereof comprising the enzyme;
e) incubating the sample of (d) with a first substrate of the enzyme associated with the second single target sites, a second population of a molecules of second substrate of said enzyme and a peroxide compound according to step (b) of method (1) above (i.e. step (b) of claim 1), thereby forming discrete deposits of molecules of second substrate of the second population at the second target sites of (d);
f) detecting in the sample the discrete deposits of molecules of second substrate of the first population at the first target sites as first visually distinct dot, thereby detecting one or more individual single units of the first population of the target;
g) detecting in the sample the discrete deposits of molecules of second substrate of the second population at the second target sites as second visually distinct dots, thereby detecting one or more individual single units of the second population of the target In another embodiment of the invention the method (1) may be used for detection and visualization of individual units of at least two different immobilized targets in a sample, which comprises the following steps:
a) incubating the sample with one or more binding agents capable of binding a first target, wherein
  (1) at least one of the binding agents comprises an enzyme;
  (2) at least one of the binding agents is capable of directly binding to an individual single unit of first target,
thereby forming one or more discrete first single target sites with individual single units of the first target, wherein each single discrete first target site comprises a complex of one individual single unit of the first target and one or more binding agents, at least one of the binding agents comprising the enzyme;
b) incubating the sample of (a) with a first substrate of the enzyme associated with the first single target sites, a first population of molecules of second substrate of said enzyme and a peroxide compound according to step (b) of method (1) above (i.e. step (b) of claim 1), thereby forming discrete deposits of molecules of second substrate of the first population at the first single target sites of (a);
c) incubating the sample of (b) with a solution of hydrogen peroxide in an amount sufficient to quench the residual activity of the enzyme associated with the first single binding sites of (a);
d) incubating the sample (c) with one or more binding agents capable of binding to a second target, wherein
  (1) at least one of the binding agents comprises an enzyme;
  (2) at least one of the binding agents is capable of directly binding to an individual unit of second target,
thereby forming one or more discrete second single target sites with individual single units of the second target, wherein each single discrete second target site comprises a complex of one individual unit of the second target and one or more binding agents, at least one of the binding agents comprising the enzyme;
e) incubating the sample of (d) with a first substrate of the associated with the second single binding sites, a second population of a molecules of second substrate of the enzyme with oxidoreductase activity and a peroxide compound according to step (b) of methods (1) above (i.e. step (b) of claim 1), thereby forming discrete deposits of molecules of second substrate of the second population at the second target sites of (d);
f) detecting in the sample the discrete deposits of molecules of second substrate of the first population at the first target sites as first visually distinct dots, thereby detecting one or more individual single units of the first target;
g) detecting in the sample the discrete deposits of molecules of second substrate of the second population at the second target sites as second visually distinct dots, thereby detecting one or more individual single units of the second target.

Another aspect of the invention relates to a method for quantification of a target in a sample, comprising
  a) processing a biological sample according to any of the methods of the invention (as above);
  b) quantifying visually distinct dots in the sample;
  c) evaluating the quantity of the target in the sample.

In another aspect the invention relates to use of single target detection and quantification methods described herein in medical diagnostics, in particular for prognostic and therapeutic applications where visualization and quantification of single units of biological markers is essential for accuracy of a diagnosis, estimation of the efficacy of therapeutic treatment, prediction of the outcome of a disease, prognosis of the risk of a disease, or stratification of patients for a therapeutic regime, etc.

In another aspect the invention relates to assays for the detection and quantification of individual single units of a variety of targets employing the methods of the invention.

The amplification system of the invention being very powerful and robust is at the same time flexible and easily controllable. It vastly expands the limits of current detection methods, in particular detection methods using a regular bright field or fluorescent microscopy for evaluation of samples. In particular, using detection methods comprising the amplification system of the invention
(i) single entities of an immobilized target can be visualized and quantified in complex samples such as histological samples;
(ii) single entities of an immobilized target can be detected and quantified using a variety assay formats;
(iii) single entities of an immobilized target can be detected and quantified very rapidly, such as within 10-20 min, however, if necessary, the visualization and detection procedures may be prolonged or interrupted for longer periods of time without compromising quality of the results;
(iv) blocking, typically used to reduce background labeling, is unnecessary;

(v) temperature control is unnecessary;
(vi) single entities of an immobilized target can be detected and quantified in a very broad dynamic range,
(vii) single entities of multiple immobilized targets can be detected and quantified in the sample in one procedure.

Thus, great advantages of the SMD visualization system of the invention are that it is simple, rapid, robust, reliable and flexible. It allows visualization and quantification of single entities of a variety of targets in a variety of samples using a variety of assays. Additional advantages are that the methods utilize compounds that are well-defined chemical compounds which are either commercially available or easy to produce. A further advantage is that all procedures of the methods can be carried out both manually and automatically.

DETAILED DESCRIPTION OF THE INVENTION

Figure 1:
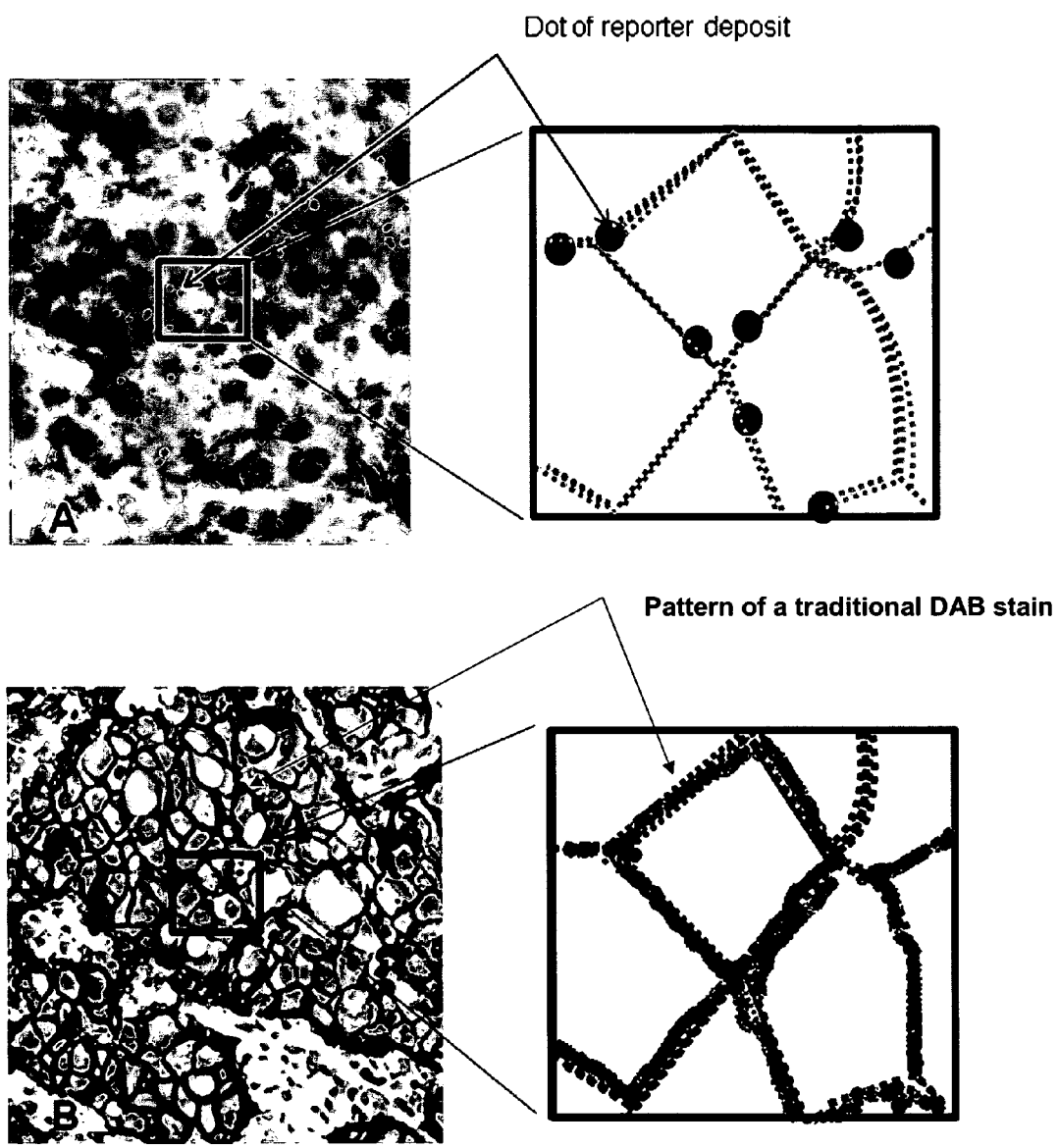
FIG. 1 shows representative microphotographs of immunochemical staining of tissue samples expressing Her2 (+2), wherein (1) is a sample where Her2 is visualized according to the invention and (2) is a sample where Her2 is visualized according to the method described in WO2009036760. The right panel is a schematic presentation of the staining pattern of method (1) and method (2).
Figure 2:
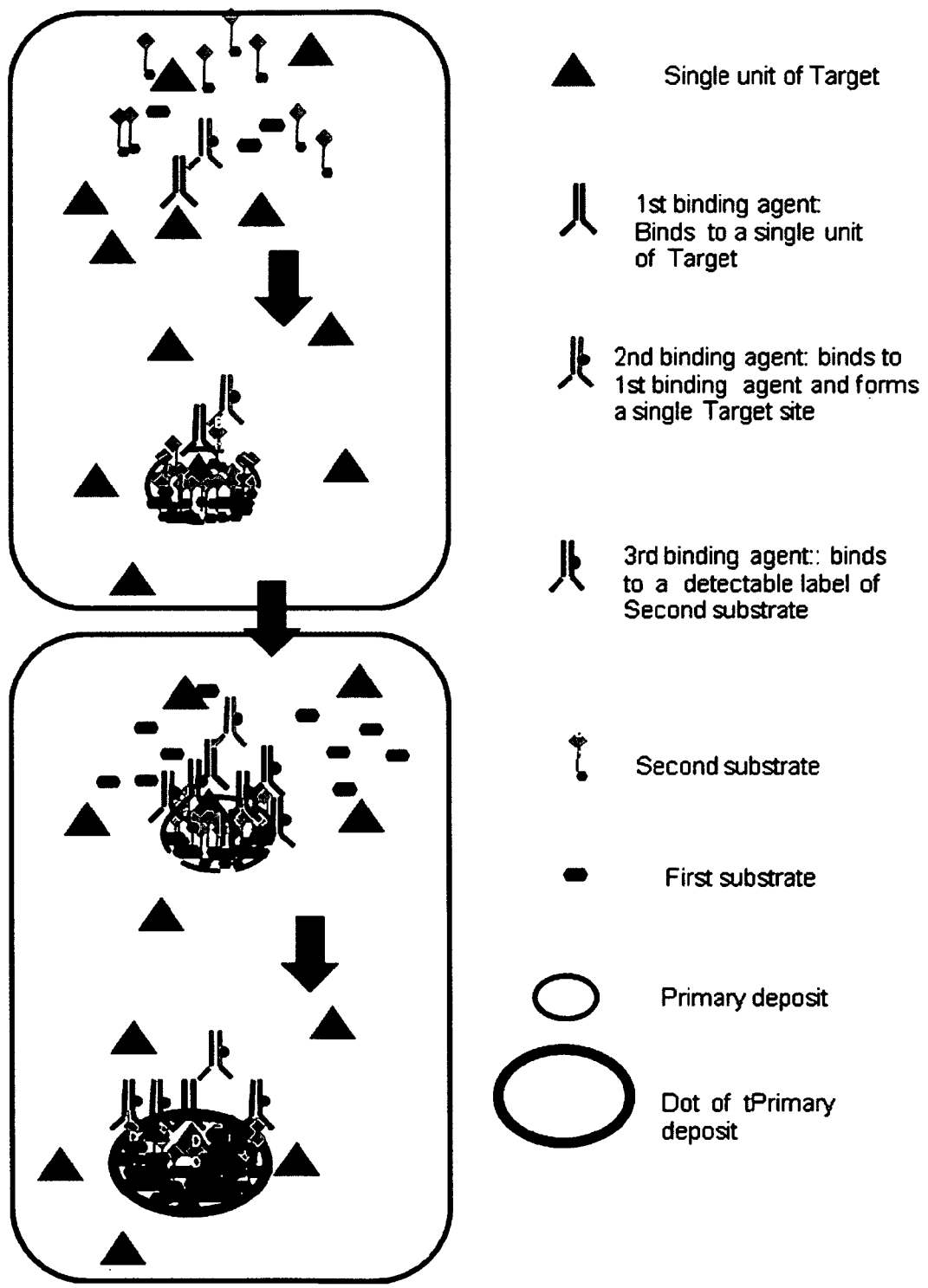
FIG. 2 is a schematic presentation of process of single molecule detection according to the method of the invention (shown the step (b) of claim 1 and step (c) claims 23-24)

Method of Visualization of Individual Units of Immobilized Targets in Samples

One aspect of the invention relates to methods of visualization of single individual units of targets, e.g. single target molecules, single particles, etc., in a sample wherein tsingle individual units of the targets are immobilized.

In one embodiment the invention relates to a method of visualization single units of an immobilized target, said method comprising the following steps:
a) forming one or more discrete single target sites, herein each discrete single target site comprises a single individual unit of the target;
b) forming discrete deposits of detectable molecules at discrete single target sites of (a) and thereby visualizing said single target sites, and, optionally,
c) detecting the discrete deposits at the discrete single target sites.

In particular, the steps (a), (b) and, optionally, (c) of the method above may be performed as the following:
a) a) Incubating a sample comprising a population of individual units of a target with of one or more binding agents, wherein
(1) at least one of the binding agents comprises an enzyme;
(2) at least one of the binding agents is capable of directly binding to an individual single unit of the target,
and forming one or more discrete single target sites a fractional sub-population of individual single units of the target, wherein each single discrete single target site comprises a complex of one individual single unit of said fractional sub-population and one or more binding agents, at least one thereof comprising the enzyme;
b) incubating a sample of (a) in an aqueous solution (i) comprising
a peroxide compound in an amount that is less than 2 mM,
a first substrate of the enzyme associated with the discrete single target sites of (a) and,
a second substrate of said enzyme,
wherein said first substrate is a water soluble electron rich organic compound which is
1) capable of generating a radical upon a reaction with said enzyme; and
2) capable of cross-linking molecules of said second substrate in the presence of both said enzyme and a peroxide compound, thereby producing a water insoluble polymeric product of said second substrate,
and wherein said second substrate is a conjugate molecule comprising at least two compounds that are capable of serving as substrates of said enzyme and a detectable label, wherein the detectable label is selected from the group consisting of a fluorescent, luminescent, radioactive or chromogenic matter or a member of a specific binding pair,
thereby forming discrete deposits of the second substrate at the discrete single target sites of (a) and visualizing said single target sites of (a) as visually distinct dots,
and, optionally,
c) detecting the discrete deposits of the first substrate at single target sites of (a), and visualizing the single target sites of (a) as visually distinct dots, and thereby visualizing single individual units of the target.

In some embodiments the step (b) may comprise sequential sub-steps:
(b') incubating the sample of (a) in an aqueous solution (ii) comprising a peroxide compound and
a first substrate of the enzyme associated with the target sites of (a),
wherein said first substrate is a water soluble electron rich organic compound which is
(1) capable of generating a radical upon a reaction with said enzyme; and
(2) capable of cross-linking molecules of said second substrate in the presence of both said enzyme and a peroxide compound, thereby producing a water insoluble polymeric product of said second substrate;
wherein the amount of the peroxide compound is less than 2 mM;
and, sequentially,
(b") incubating the sample (b') in an aqueous solution (i) (as above).

In some embodiments the step (c) may comprise the following sub-steps:
c') incubating the sample of (b) comprising discrete deposits of the second substrate at single target sites of (a) with a binding agent capable of specifically binding to a detectable label of the deposited second substrate and form a complex comprising one or more molecules of the deposited second substrate and one or more molecules of said binding agent, (c'') detecting in the sample (c') the binding agent bound to the discrete deposits of the second substrate, thereby detecting single target sites and thereby detecting the individual single unit of the target associated with said single target site.

The methods of the invention (as above and as described below) may optionally comprise one or more additional steps, e.g. steps preceding the step (a), (b) or (c) e.g. a step of quenching the sample with a compound inhibiting endogenous or residual peroxidase activity of the sample preceding step (a), or one or more steps between the steps (a), (b) and/or (c), or steps following the step (c), e.g. one or more washing steps preceding, following or between the steps (a), (b) and (c). In one embodiment, the methods may comprise at least one automated step.

Other embodiments of the method are discussed in the following sections.

Sample

The term "sample" means a representative part or a single item from a larger whole or group, an amount or portion of a matter or object that supposedly contain a target to be detected, e.g. a portion or amount of biological, chemical, environmental material comprising a target molecule, particle, structure to be analyzed, e.g. a biopsy sample, a food sample, a soil sample, etc. A typical sample shows what the rest of the matter or object is or should be like. In one embodiment a sample of the invention may be an environmental sample, e.g. a sample of a soil or a sample of a spillage. In another embodiment the sample may be a food sample. In another embodiment the sample may be a portion of a library of organic molecules. In another embodiment the sample may be a sample of warfare.

In one embodiment a sample of the invention is a biological sample.

A biological sample may be exemplified by:
1. a sample comprising suspended cells and/or cells debris, e.g. blood sample, suspension of cloned cells, body tissue homogenate, etc;
2. a sample comprising of intact or damaged cells of an animal body, a body tissue, smear or fluid or a sample of a tumor, e.g. a biopsy sample; It may be a fresh tissue sample or preserved tissue sample, e.g. a formalin fixed paraffin embedded tissue sample;
3. a sample comprising a living organism, e.g. a sample of a medium comprising an animal, plant, bacterium, fungi, etc;
4. a sample comprising viral particles, debris thereof, or viral products, e.g., a body smear comprising viral nucleic acids, proteins, peptides, etc;
5. a sample comprising a cell organelle(s);
6. a sample comprising natural or recombinant biological molecules, e.g. blood plasma sample, conditioned cell culture media, etc.
7. a sample comprising plant cells or derbies thereof.

The above mentioned examples of biological samples are given for the purpose of illustration, but not limitation of embodiments of the invention.

Examples of chemical samples may be illustrated by and are not limited to samples of libraries of chemical compounds, e.g. peptide libraries. Examples of the environmental samples may be illustrated by and are not limited to soil, water or air samples and food samples.

The invention relates to samples (e.g. as any of the above examples) comprising an immobilized target, i.e. to samples where the target is prevented from freedom of movement during the detection procedure according to the present invention, e.g. samples where the target motion is substantially reduced or eliminate by mechanical or chemical means, as e.g. in case of samples or targets attached to or within a certain support or medium. Thus, a sample comprising single individual units of a target of interest may in one embodiment be immobilized onto a solid support before the detection procedure, e.g. a solid body tissue sample immobilized on a glass slide. Examples of samples comprising immobilized targets of the invention include but not limited to body tissue samples immobilized on glass or plastic slides, or to samples comprising biological or chemical molecules immobilized onto membranes or ELISA plates, etc. A target of a sample in these embodiments may be immobilized either within the sample, e.g. a protein fixed within a tissue sample, or is immobilized on the surface or within certain material, such as e.g. a portion of a solid material or a gel such as a nitrocellulose membrane, etc. In one embodiment the solid support may be a three-dimensional structure, e.g. a collagen or agar block. In this embodiment a target, e.g. molecule or particle may be immobilized within the structure.

In one embodiment the invention relate to a sample that does not comprise the target, e.g. a control sample. In another embodiment, the invention relate to a sample that supposedly comprise the target, e.g. a sample with unknown content.

The term "solid support" mentioned above means a piece of any material that is insoluble under conditions of the procedures according to the invention, e.g. it may be a nitrocellulose membrane, glass slide etc. Examples of supports suitable for immobilizing samples and/or targets include but not limited to synthetic polymer supports, such as polystyrene, polypropylene, substituted polystyrene, e.g, aminated or carboxylated polystyrene; polyacrylamides; polyamides; polyvinylchloride; glass; agarose; nitrocellulose; nylon; polyvinylidenedifluoride; surface-modified nylon, etc. The invention relates to a solid support that is chemically inert under conditions described herein, i.e. the chosen support may not have any major influence on the results of detection by the method. Accordingly, any such inert support suitable for immobilizing a sample or target fitting the chosen assay format, e.g. for IHC, ELISA, blotting etc, may be selected Target The term "target" means in the present content an object of interest supposedly present in a sample that can be characterized by particular physical and/or functional features. It is understood that in the context of the invention the term "target" relates to the whole pool of substantially identical entities of that object, not to a single entity of that object in a sample. The term "substantially identical" in the present context means that all or substantially all single entities of the total pool of a target in a sample possess one or more features that make them recognizable as the target. For example, the target may be a particular protein including all molecules of that particular protein in a sample; another example of a target of the invention may be a particular molecular complex or structure including substantially all objects of the sample that comprise that particular molecular complex or molecular structure; another example of a target of the invention may be a viral particle or a bacterium, wherein total population of that viral particles or that bacteria of the sample is the target.

Biological objects such as molecules, molecular complexes, structures, particles or organisms which are associated with features that are characteristic for a particular cell type, tissue, cellular structure, physiological condition, etc., are often termed "biological markers" of that particular cell type, tissue, cellular structure, or physiological condition. Non-limited examples of such biological markers include but not-limited to particular nucleotide sequences, proteins or other biological molecules, e.g. carbohydrates or lipids, chromosomal or membrane structures, viruses, bacteria, microorganisms etc. In some embodiments of the invention, the term "target" is used interchangeable with the term "biological marker" and relates to a molecule, molecular complex, structure or particle that is characteristic for a particular cell type, tissue, physiologic condition, etc, wherein the total population of any of the latter biological markers in the test sample is considered to be the target.

In one embodiment, the target may be a protein, e.g. a cellular membrane receptor or a cytoplasmic protein, in another embodiment the target may be a nucleic acid, e.g. a cytoplasmic nucleic acid. Derivatives of any latter mentioned targets, e.g. fragments, precursors, mutants of target proteins or nucleic acids, etc. may also be targets in some embodiments of the invention.

Thus, in different embodiments of the invention the target may be a biological or chemical target molecule, or a particle, or a molecular or cellular complex, or molecular or cellular structure, or a virus, or a microorganism, or a fragment of said target molecule, particle, complex, structure, virus or microorganism. Among targets contained in chemical and environmental samples may be different pollutants, toxins, warfare substances, members of molecular libraries, industrial noxious waste compounds, etc.

In particular the invention relates to targets that may be represented in a sample by a plurality of independent substantially identical units, in particular the invention relates to single individual units of a target.

By the term "unit" is meant a single quantity of a target regarded as a whole in calculation and serving to perform one particular function. The term "individual" means that a unit is separable from the other units of the same kind or other components of the environment (by physical features of a function) and can be considered and counted separately. The term "individual unit" is interchangeably used with the term "single unit". The term "single" in the present content means a target unit is consisting of a separate whole, is consisting of only one in number, is consisting of one as opposed to or in contrast with many. For example a single/individual unit of a target protein means a single individual protein molecule of the target protein, i.e. one molecule of plurality molecules of the same kind. The term "substantially identical units" means that a plurality of single units of a target possesses one or more features that make these units be considered as the target. The term "independent" means that a single unit of a target exists as a distinct entity and do not depend on the existence of other distinct entities of the same kind in the sample.

The invention is some embodiments relate to a single unit being a single part of a molecule. The term "single part of molecule" relates to a part of a molecule that has particular properties that allow considering this part of the molecule separately from the other parts of the same molecule, e.g. a proteolytic fragment of a target protein, a part of a fusion protein, a particular domain of a target protein, a particular structure of a nucleic acid, an epitope, etc.

Thus, in one embodiment, the invention may relate to single/individual units of a target being single individual target molecules, i.e. to a plurality of single individual target molecules present in a sample, in another embodiment the invention may relates to single/individual units of a target being single individual parts of a molecule, e.g. a particular molecular structures that presents in a plurality target molecule in a sample, e.g. an epitope. In another embodiment the invention may relate to a plurality of single individual viral particles making a pool of viral particles present in a sample.

In different embodiments a plurality of single units of a target may be represented by single individual biological or chemical molecules, single individual single particles, single individual molecular or cellular complexes, single individual molecular or cellular structures, or single individual viruses or single individual microorganisms, or single individual fragments of said molecules, particles, complexes, structures viruses or microorganisms.

In one preferred embodiment, the target is a biological marker related to cancer, e.g. nucleic acids and polypeptides of hormones and growth factors and their receptors, cell adhesion molecules signal transduction molecules, cell cycle regulation molecules, etc, e.g. genes, RNAs and proteins of the group including growth factors PDGF, VEGF, TGF, HGF or EGF, their receptors and the pathway related molecules, genes and their products relating to signal transduction pathways, e.g. the JAK/STAT pathway or Akt1/PKB cell survival pathway, or 5-FU pathway, estrogen receptor ER and its gene (ERS1), etc. The methods of the invention allow simple and rapid visualization and quantification of said biological markers.

The methods of the invention allow visualizing and quantifying single individual units of a target present in a sample in a broad dynamic range. Both very high amounts and very low amounts of a target may be visualized and quantified in one and the same sample, or they may be evaluated in separate samples. Two or more different targets may be visualized in one or the same sample, e.g. a protein target and nucleic acid target, or two or more different protein targets, or two or more different nucleic acid targets, etc.

In one embodiment, single units of a target may be distributed substantially homogeneously throughout a sample, in other embodiments, single units of a target may present more abundant in one part of a sample and less abundant in other parts thereof. In all the latter embodiments, single units of the target may be visualized and quantified in one and the same sample using methods of the present invention. In some embodiments, wherein a single target unit is associated with another target of interest, e.g. present in a particular molecular association or a structure which said particular association or structure is a biomarker of a pathological condition. said another target of interest may be visualized and quantified by visualizing and quantifying single target units in the sample as well.

In one embodiment, the invention relate to a fractional sub-population of single target units present in a sample, such as a majority or a minority of the total number of single individual target units present in the sample. The term "fractional subpopulation" in the present context means a portion of the total population of single target units that is equal or less than 99%. e.g. equal or less than 90% of the total quantity of single units of the target in the sample, such as less than 85%, e.g. 75-80% of the total quantity of units of the target in the sample, such as less than 75%, for example from 1% to 50% of the total quantity of single units of the target in the sample, such as. from 1% to 25% of the total quantity of units of the target in the sample, etc. A fractional sub-population single target units that is represented by 50%-99% of the total population is defined according to the invention as a majority of single target units present in the sample. A fractional sub-population is represented by less than 50% of the total population of single target units in a sample is defined according to the invention as a minority of single target units present in the sample In one embodiment, a majority of individual single target units may be involved in formation of discrete single target sites of the invention; in another embodiment, a minority of individual single target units may be involved in formation of discrete single target sites of the invention. In one embodiment, when a target or single units of a target are present in a sample in very low amounts, it may be preferred that substantially all individual single units are involved in formation of discrete single binding sites of the invention.

Binding Agent

Methods of the invention comprise a step wherein a sample presumably comprising a target is incubated with one or more binding agents, at least one thereof is capable of recognizing and specifically binding to a single individual unit of the target.

The term "binding agent" designates a molecule that is capable of directly or indirectly specifically binding to a single unit of a target, e.g. an individual molecule of a target. protein. The term "specifically" means that the binding agent has a particular affinity to the target, e.g. affinity to a target molecule, or particular affinity to an agent that is bound to the target, e.g. affinity to a primary antibody bound to a target protein, affinity to a hapten conjugated with a primary antibody, etc. The term "directly" means that a binding agent having a specific affinity to a single individual unit of target interacts and forms an immediate bond with this single individual unit upon interaction, e.g. a primary antibody binds directly to a single individual target molecule that was used as an antigen for raising said primary antibody. The term "indirectly" in the present context relates to a binding agent, wherein said binding agent has no specific affinity to a single individual unit of the target, but wherein said binding agent has a specific affinity to another substance that is capable of specifically binding to that single individual unit, e.g. a primary antibody, or wherein said binding agent has a specific affinity to a substance that is associated or linked to said single individual unit, e.g. to a hapten; said binding agent directly interacts with the latter substances and forms a bond with said substance, and thereby the binding agent becomes indirectly bound to the single unit of the target.

A binding agent which is capable of directly specifically binding to a single unit of target is typically represented herein by a first binding agent. A binding agent which is capable of indirectly specifically binding to a single unit of target is typically represented by a second binding agent. However, a detection system according to the invention may comprise further binding agents that can be indirectly bound to the single unit of the target, e.g. third, fourth, and further binding agents.

Typically, a first binding agent or, in some embodiments, a second or third binding agent, is used to contact the sample to recognize the target, bind to it and form a complex with it. Second, third and further binding agents may be used in further steps of methods according to the invention, e.g. for recognition of deposits of detectable molecules i at target sites described below. In some embodiments, second, third and further binding agents are used to amplify a signal associated with a target. These binding agents are also useful to add flexibility to the detection system, e.g. to change the original signal associated with the target, e.g. a red fluorescent signal to green, etc, Binding agents of the invention may be members of different specific binding pairs.

A number of different specific binding pairs are known in the art, these are the pairs of two different molecules which are capable of specific binding to each other. Members of specific binding pairs suitable for use in practicing the invention may be of the immune or non-immune type.

Non-immune specific binding pairs include systems wherein the two components share a natural affinity for each other but are not antibodies. Exemplary non-immune binding pairs are biotin-avidin or biotin-streptavidin, folic acid-folate binding protein, complementary nucleic acids, receptor-ligand, etc. The invention also includes non-immune binding pairs which form a covalent bond with each other. Exemplary covalent binding pairs include sulfhydryl reactive groups such as maleimides and haloacetyl derivatives and amine reactive groups such as isothiocyanates, succinimidyl esters, sulfonyl halides, and coupler dyes such as 3-methyl-2-benzothiazolinone hydrazone (MBTH) and 3-(dimethyl-amino) benzoic acid (DMAB), etc.

Immune specific binding pairs may be exemplified by antibody-antibody systems or hapten-anti-hapten systems. In one embodiment the immune specific binding pair of the invention may be an antibody-antibody binding pair comprising two or more antibody molecules having affinity to each other, for example a primary antibody and secondary antibody pair, wherein the primary antibody represents the first binding agent and the secondary antibody represents the second binding agent; Antibody systems comprising 3 or 4, or more antibody members may be used in another embodiment. In other embodiments of the invention the immune binding pair may be represented by a hapten-anti-hapten system. In such embodiments the first binding agent may be represented by a conjugate comprising a molecule having affinity to the target and a hapten, e.g. a primary antibody or nucleic acid sequence linked to a hapten, and the second binding agent may be represented by an anti-hapten antibody.

The term "hapten" designates a small molecule which can be considered as an isolated epitope to which an antibody can be made, although the hapten alone will not induce an immune response if injected into an animal, it must be conjugated to a carrier (usually a protein). As haptens are small molecules, multiple copies of a hapten may be attached to a large molecule, e.g. a polymer molecule, such as protein, nucleotide sequence, dextran, etc. Haptens may serve as convenient label molecules for assay formats where it is necessary or advantageous to amplify a signal. Thus, the bound multiple copies of a hapten provide for enhanced sensitivity, e.g. increased signal strength. Non-limited examples of suitable haptens include Fluorescein (FITC), 2,4-Dinitrophenol (DNP), myc Digoxigenin (DIG), tyrosine, nitrotyrosine biotin and dyes. e.g. tetramethylrhodamine, Texas Red, dansyl, Alexa Fluor 488, BODIPY FL, lucifer yellow and Alexa Fluor 405/Cascade Blue fluorophores, Haptens are described in US20080305497 may also be used for the purposes of the invention.

The term "antibody", as used herein, designates an immunoglobulin or a part thereof, and includes any polypeptide comprising an antigen binding site regardless of the source, method of production, and other characteristics. The term includes for example, polyclonal, monoclonal, monospecific, polyspecific, humanized, single chain, chimeric, synthetic, recombinant, hybrid, mutated, and CDR-grafted antibodies. A part of an antibody can include any fragment which can still bind antigen, for example, an Fab, $F(ab')_2$, Fv, scFv. The origin of the antibody is defined by the genomic sequence irrespective of the method of production.

Primary antibody, in context of the present invention, refers to an antibody binding agent, e.g. a whole antibody molecule, a fragment or a derivative of said molecule, e.g. a conjugate comprising an antibody or a polymerized antibody, that specifically binds to a target, more specifically to a single unit of a target of a sample, e.g. to a single target molecule. In some embodiments, a primary antibody may be a bivalent antibody which is capable of binding to two (or more) single individual units of different targets, e.g. an antibody that is capable of binding to a receptor dimer, e.g. Her2/Her3 dimer. In this embodiment the single unit of a target according to the invention is a single Her2/Her3 dimer, and the target is a population of Her2/her3 dimers in a sample including all said dimers of the sample. Primary antibodies may be derived from any warm blooded species, e.g. mammals, birds.

Secondary antibody, in context of the present invention, refers to an antibody binding agent, e.g. a whole antibody molecule, a fragment or a derivative of said molecule, e.g. a conjugate comprising an antibody or a polymerized antibody, that has an antigen binding domain that specifically binds to the primary antibody, or a hapten deposited in the target site, or hapten linked directly or indirectly to a primary antibody or another binding agent.

Tertiary antibody, in context of the present invention, refers to an antibody binding agent, e.g. a whole antibody molecule, a fragment or a derivative of said molecule, e.g. a conjugate comprising an antibody or a polymerized antibody that comprise an antigen binding domain that specifically binds to a secondary antibody or a hapten linked to a secondary antibody or a hapten linked to polymer conjugated to a secondary antibody, or hapten deposited in the target site.

Sometimes an antibody may function both as a secondary and a tertiary antibody.

Antibodies used in the invention, including primary antibodies, secondary antibodies and tertiary antibodies, may be derived from any mammal species, e.g., a rat, a mouse, a goat, a guinea pig, a donkey, a rabbit, horse, lama, camel, or any avian species e.g., chicken, duck. Derived from any mammal or avian species, as used herein, means that at least a part of the nucleic acid sequence encoding a particular antibody originated from the genomic sequence of a specific mammal, e.g., a rat, a mouse, a goat, or a rabbit or a specific bird e.g., chicken, duck. The antibody may be of any isotype, e.g., IgG, IgM, IgA, IgD, IgE or any subclass, e.g., IgG1, IgG2, IgG3, IgG4.

In certain embodiments a primary antibody contains an antigen binding region which can specifically bind to a biological marker, in particular to a single individual unit of said biological marker, expressed by cells of a biological sample. The marker may be expressed on the cell surface or within the cell membrane, i.e., on the interior of the cell, e.g., within the cytoplasm, within the endoplasmic reticulum, etc. In some embodiments the biological marker may be extracted from the cell and thus it is present in a cell-free medium, e.g. in an aqueous solution, or it is a soluble molecule present in a cell culture media, blood plasma, cerebrospinal fluid, etc. Examples of the corresponding samples are described above.

In certain embodiments, a secondary antibody contains an antigen binding region which specifically binds to a primary antibody, e.g., to the constant region of the primary antibody. In certain embodiments, a secondary antibody may be conjugated to a polymer. In some embodiments, 2-20 secondary antibodies, such as 5-15 secondary antibodies may be conjugated with a polymer. In other embodiments, a polymer may be conjugated with 1-10 secondary antibodies, such as 1, 2, 3, 4, 5, 6, 7, 8, 9 or 10 secondary antibodies.

In certain embodiments, a tertiary antibody may contain an antigen binding region which specifically binds to a secondary antibody, e.g., to a constant region of a secondary antibody, or to a hapten linked to a secondary antibody, or to a polymer conjugated with a secondary antibody. In certain embodiments, a tertiary antibody is conjugated to a polymer. In some embodiments, 1-20 tertiary antibodies may be conjugated a polymer. In other embodiments, 1-5 tertiary antibodies, such as 1, 2, 3, 4 or 5 tertiary antibodies may be conjugated with a polymer.

In some embodiments, polymers comprising a single binding unit of a binding agent, e.g. a polymer conjugated with one molecule of primary, secondary or tertiary antibody, may be preferred.

Antibodies that may be used for the purposes of the invention include monoclonal and polyclonal antibodies, engineered antibodies including chimeric, CDR-grafted and artificially selected antibodies produced using phage display or alternative techniques.

Antibody binding agents of the invention may be produced by any of numerous methods well-known in the art e.g., according to Harlow and Lane, *Antibodies: a Laboratory Manual*, (1988) (Cold Spring Harbor Press, Cold Spring Harbor, N.Y.). Techniques for the preparation of recombinant antibody molecules are described in the above reference and a number of other references, e.g., EP 0623679; EP 0368684; and EP 0436597. Nucleic acids encoding antibodies may be isolated from a cDNA library. Nucleic acids encoding antibodies may be isolated from a phage library (see e.g. McCafferty et al. 1990, Nature 348:552, Kang et al. 1991, *Proc. Natl. Acad. Sci. USA* 88:4363; EP 0 589 877 B1). Nucleic acids encoding antibodies can be obtained by gene shuffling of known sequences (Mark et al. 1992, *Bio/Technol.* 10:779). Nucleic acids encoding antibodies can be isolated by in vivo recombination (Waterhouse et al. 1993, *Nucl. Acid Res.* 21:2265). The antibodies used in the methods of the invention include humanized immunoglobulins (see U.S. Pat. No. 5,585,089, Jones et al. 1986, *Nature* 332:323). Antibodies of the invention may be altered any possible way, presuming that they retain their binding affinity, e.g, they may fused with an effector protein, toxin, label, etc. Methods of conjugation of antibody with different agents are also well known in the and described in exemplary embodiment of the invention below.

In one embodiment of the invention, an antibody binding agent is represented by the Fab region.

In one embodiment an antibody binding agent may be a composition comprising two or more different antibody binding agents, e.g., a composition comprising a first antibody binding agent and a second antibody binding agent, wherein the two or more different antibody agents are of different immune binding pairs. In one embodiment, in the composition, at least one of two or more different antibody binding agents of is an antibody that is capable of specifically binding to a target and at least one another is an antibody which comprises a an enzyme.

In another embodiment, the invention relates to binding agents that are members of non-immune specific binding pairs, such as complementary nucleotide sequences, or nucleic acid analog molecules.

A binding agent comprising a nucleic acid or nucleic acid analog molecule, e.g., a DNA molecule, an RNA molecule, a PNA molecule, may be useful for the visualization and quantification of single individual units of nucleic acid targets.

Nucleic acid sequences used as binding agents for the purposes of the invention may be synthesized chemically or produced in recombinant cells. Both modes of production are well known in ht eart (see e.g. Sambrook et al. (1989) *Molecular Cloning: A Laboratory Manual, 2nd ed.* Cold Spring Harbor Press). In some embodiments, a nucleic acid binding agent may comprise a peptide nucleic acid (PNA). A peptide nucleic acid is a nucleic acid molecule in which the deoxyribose or ribose sugar backbone, usually present in DNA and RNA is replaced with a peptide backbone. Methods of making PNAs are known in the art (see e.g. Nielson, 2001, *Current Opinion in Biotechnology* 12:16) (hereby incorporated by reference). In other embodiments, the binding agent may comprise a locked nucleic acid (LNA) (Sorenson et al. 2003, *Chem. Commun.* 7(17):2130).

A nucleic acid binding agent, in some embodiments, may comprise at least one oligo- or at least one polynucleotide sequence that specifically hybridizes to a single unit of a target sequence in a biological sample, e.g. a single mRNA sequence, under specific conditions of stringency. The term "hybridization under stringent conditions," is used herein to describe conditions for hybridization under which nucleotide sequences that are significantly complementary to each other, such as at least 70%, at least 80%, at least 85-90% complementary, remain bound to each other. The percent complementary is determined as described in Altschul et al. (1997) *Nucleic Acids Res.* 25:3389-3402 (hereby incorporated by reference).

Specified conditions of stringency are known in the art and can be found in *Current Protocols in Molecular Biology*, John Wiley & Sons, Inc. (Ausubel et al. 1995 eds.), sections 2, 4, and 6 (hereby incorporated by reference). Additionally, specified stringent conditions are described in Sambrook et al. (1989) *Molecular Cloning: A Laboratory Manual, 2nd ed.* Cold Spring Harbor Press, chapters 7, 9, and 11 (hereby incorporated by reference). In some embodiments, the hybridization conditions are high stringency conditions. An example of high stringency hybridization conditions is hybridization in 4× sodium chloride/sodium citrate (SSC) at 65-70° C. or hybridization in 4×SSC plus 50% formamide at 42-50° C., followed by one or more washes in 1×SSC, at 65-70° C. It will be understood that additional reagents may be added to hybridization and/or wash buffers, e.g., blocking agents (BSA or salmon sperm DNA), detergents (SDS), chelating agents (EDTA), Ficoll, PVP, etc.

In some embodiments, the binding agents may hybridize to a target sequence in a sample under moderately stringent conditions. Moderate stringency, as used herein, include conditions that can be readily determined by those having ordinary skill in the art based on, for example, the length of the DNA. Exemplified conditions are set forth by Sambrook et al. *Molecular Cloning: A Laboratory Manual*, 2d ed. Vol. 1, pp. 1.101-104, Cold Spring Harbor Laboratory Press (1989) (hereby incorporated by reference), and include use of a prewashing solution of 5×SSC, 0.5% SDS, 1.0 mM EDTA (pH 8.0), hybridization conditions of 50% formamide, 6×SSC at 42° C. (or other similar hybridization solution, such as Stark's solution, in 50% formamide at 42° C.), and washing conditions of 60° C., 0.5×SSC, 0.1% SDS.

In some embodiments, the binding agents hybridize to a target sequence in a sample under low stringent conditions. Low stringency conditions may include, as used herein, conditions that can be readily determined by those having ordinary skill in the art based on, for example, the length of the DNA. Low stringency may include, for example, pretreating the DNA for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ CPM binding agent is used. Samples are incubated in hybridization mixture for 18-20 hours at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C.

In other embodiments the invention may relate to binding agents that are peptide sequences or comprise peptide sequences that are derived from non-antibody proteins, e.g. peptide sequences derived from nucleic acid binding domains of different proteins, ligands of different cellular and nuclear receptors and their derivatives. Some non-limiting examples of such binding agents may be c1q protein of the classical pathway of the complement cascade which can bind to an antibody constant region, a MHC molecule, e.g., MHC class I and MHC class II and non conventional MHC, a molecule having a specific binding partner, such as molecules involved in cellular signaling pathways such as molecules having leucine zipper domains, e.g., fos/jun, myc, GCN4, molecules having SH1 or SH2 domains, such as Src or Grb-2; an immunoglobulin receptor, e.g., an Fc receptor; a chimeric protein, i.e., a protein engineered to combine the features of two or more specific binding partners, e.g., a leucine zipper could be engineered into a Fc region of an antibody, an SH2 domain could be engineered to be expressed in a Fc region of an antibody. In other embodiments, fusion proteins can be engineered comprising an Fc portion of an antibody with a substituted variable domain.

The binding agent may also be small molecules which can bind specifically to certain structural units of large biological molecules.

In some embodiments binding agents may comprises a detectable label, e.g. a fluorescent substance, hapten, enzyme, etc. In one embodiment, the invention relates to labeled binding agents, i.e. labeled third or further binding agents, that are capable of specifically binding to the deposited detectable molecules and are used for visualization of target sites of the invention. In one embodiment, the invention relates to a binding agent comprising an enzyme label. Non-limiting examples of suitable enzyme labels may be horseradish peroxidase (HRP), alkaline phosphatase (AP), beta-galactosidase (GAL), glucose-6-phosphate dehydrogenase, beta-N-acetylglucosaminidase, β-glucuronidase, invertase, xanthine oxidase, firefly luciferase, glucose oxidase (GO). In one embodiment a binding agent may comprise HRP as a label. In another embodiment, a binding agent may comprise AP as a label.

Amounts of binding agents necessary for forming target sited of the invention may vary depending on different factors, e.g. sample species, target species, binding agent species, binding affinity of binding agents, etc. Using common general knowledge the skilled in the art can select an appropriate binding agent and determine the amount needed for every particular embodiment. In some embodiments it may be preferred that the amounts of binding agents forming the target sites are adjusted so that not all single units of a target present in the sample, but a fractional sub-population thereof is involved in formation of target sites of the invention, e.g. in embodiments when the sample comprise a target in abundant amounts, or a target present in a broad dynamic concentration range. In other embodiments, it may be preferred that all or substantially all single units of a target are involved in formation of target sites of the invention, e.g. in case of samples with a very low target expression of a target or single units of a target. In the latter embodiments, it may be preferred to use binding agents in amounts that will secure formation of binding sites with a substantial majority of individual single units of the sample, i.e. a substantial majority of single units of a target present will be involved in formation the target sites.

Enzyme

According to the invention a sample comprising one or more individual unit of a target According to the invention at least one binding agent comprising an enzyme binds, directly or indirectly, a single unit of the target and forms a complex with said unit.

The enzyme according to the invention is an enzyme with oxidoreductase activity (interchangeably termed herein as "oxidoreductase" or "enzyme of the invention").

By the term "enzyme with oxidoreductase activity" is meant an enzyme classified as EC 1 in the EC number classification of enzymes that catalyzes the transfer of electrons from one molecule (the reductant, also called the hydrogen or electron donor) to another (the oxidant, also called the hydrogen or electron acceptor). In some preferred embodiments, the invention relates to oxidoreductases classified as E 1.10. (phenoloxidases) and E 1.11. (peroxidases).

In one preferred embodiment the invention relates to phenoloxidases, in particular to the family of copper-containing oxidase enzymes, laccases (E 1.10.3.2). Laccases act on phenols and similar molecules, performing one-electron oxidation. Laccases play a role in the formation of lignin by promoting the oxidative coupling of lignols, a family of naturally occurring phenols. A laccase suitable for the purposes of the invention may be for example an enzyme described by Phillips L E and Leonard T J (Benzidine as a Substrate for Measuring Phenoloxidase Activity in Crude Cell-Free Extracts of Schizophyllum commune. Mycologia 1976, 68: 277-285,), or Kunamneni A, Plou F J, Ballesteros A, Alcalde M. (Laccases and their applications: a patent review. Recent Pat Biotechnol. 2008, 2(1):10-24), or Rodríguez Couto S, Toca Herrera J L (Industrial and biotechnological applications of laccases: a review. Biotechnol Adv. 2006, 24(5):500-13.)

The term "laccase" is used herein to designate an enzyme with phenoloxidase activity of the invention, however it is understood then laccase is one of many embodiments of penoloxidase that are suitable for the purposes of the invention.

In another preferred embodiment, the invention relates to a peroxidase enzymatic activity catalyzing a reaction of the form:

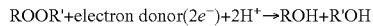

ROOR'+electron donor($2e^-$)+$2H^+$→ROH+R'OH

In one preferred embodiment of the invention, the enzyme with peroxidase activity is horseradish peroxidase (HRP). In another embodiment of the invention, the enzyme with peroxidase activity is soyabean peroxidase (SP).

For some peroxidases the optimal substrate is hydrogen peroxide, some others are more active with organic hydroperoxides such as organic peroxides. The nature of the electron donor is very dependent on the structure of the enzyme, e.g. horseradish peroxidase (HRP) can use a variety of organic compounds both as electron donors and acceptors. HRP has an accessible active site, and many compounds can reach the site of the reaction.

The enzymatic activity, i.e. oxidireductase activity, e.g. phenoloxidase or peroxidase activity, may be represented by a full-length molecule of an enzyme which is directly or indirectly linked to the molecule of a binding agent, or a fragment of the enzyme conflated with the enzymatic activity, e.g. 51% to 99.9% of the full size of the enzyme molecule, or less than 51%, e.g. 40%, 30% or less.

A binding agent of the invention may be directly or indirectly conjugated with one or more enzyme moieties, (the term "moiety" in the present content means a part of molecule of the enzyme that is capable of oxidoreductase activity, it includes both entire or substantially entire enzyme molecule and portions of said molecule that are capable of oxidoreductase enzymatic activity). Molecules of both or either first and/or second binding agents may be conjugated with one or several functionally active moieties of an oxidoreductase. In one embodiment at least one molecule of a first binding agent may be conjugated with one or more enzymatic moieties capable of oxidoreductase activity; in another embodiment at least one molecule of a second binding agent may be conjugated with one or more such moieties. Molecules of third and further binding agents may also be conjugated with an oxidoreductase. The term "directly conjugated" means that an enzyme moiety is linked to a molecule of a binding agent via a chemical bond. The term "indirectly conjugated" means that a moiety of an enzyme is linked to the molecule of a binding agent via a linking molecule, which has one chemical bond with binding agent and another chemical bond with the enzyme. Methods of conjugating biological molecules and linker molecules are well-known in the art and exemplified below.

In one embodiment the moiety of oxidoreductase is a moiety of HRP, e.g. the whole HRP molecule a fragment thereof that is capable of the HRP enzymatic activity, it may also be a recombinant protein comprising the part of HRP that possesses the enzymatic activity, etc. In another embodiment the moiety of oxidoreductase may be a moiety of soybean peroxidase (SP). In another embodiment the moiety of oxidoreductase may be a moiety of laccase.

Non-limiting examples of binding agents which comprise an enzyme with oxidoreductase activity may be antibody molecules or derivatives thereof, e.g. a Fab, conjugated with one or more moieties of HRP, and nucleic acid binding agents conjugated with HRP. Such binding agents may bind directly or indirectly to single target units, e.g. single target molecules, and form thereby complexes, wherein a single such complex comprises a single individual unit of the target and one or more of binding agents wherein one or more of the binding agents comprise an enzyme with oxidoreductase activity.

In one embodiment the binding agent is a conjugate comprising one, or two or more moieties of a peroxidase wherein said moieties are directly linked to the binding agent, e.g. an antibody molecule directly conjugated with one or more moieties of HRP. In another embodiment the binding agent may be a conjugate that comprises two or more enzymes with peroxidase activity, e.g. two or more moieties of HRP, that are linked to the binding agent indirectly, e.g. a conjugate wherein one or more molecules of an antibody and one or more HRP moieties independently linked to a backbone polymer, i.e. the enzyme with peroxidase activity is indirectly linked to the binding agent, i.e. to the antibody.

The number of HRP per molecule of binding agent may vary, from being 1 enzyme moiety per a binding agent 20-50 per a binding agent or be even higher. In some embodiments it may be preferred to use binding agents wherein the number of HRP moieties is at least two, preferably from two to twenty-twenty five enzyme moieties per binding agent, e.g. between three and twenty, such as 4, 5, 6, 7, 8, 9, 10 etc. It has surprisingly been found that, using binding agents, wherein the number of the enzyme moieties per binding agent is more than one, preferably more than two per binding agent, preferably more than tree per binding agent. In some embodiments it may be preferred to use binding agents comprising more than four enzyme moieties per binding agent per binding agent, preferably between 5 and 20, for example from 5 to 15. Binding agents with more than four enzyme moieties are favorable for formation of target sites which can be visualized as substantially identical in size dots. In some embodiments, it may be even preferred that each binding agent molecule comprising the enzyme of a pool of such binding molecules comprises approximately the same number of enzyme moieties, e.g. 4-6 per binding agents of a pool, 5-7, 6-8, 7-9, 8-10, etc moieties of enzyme per binding agent molecule, e.g. 5-6 or 6-7 HRP moieties per an antibody molecule, e.g. per primary or per secondary antibody molecule. The latter mentioned binding agent constructs comprising multiple moieties of HRP are exemplary. To achieve the mentioned effect, a binding agent may comprises multiple moieties of any enzymes with oxidoreductase activity of the invention discussed above. The binding agent may also comprise a combination of multiple moieties of different oxidoreductase enzymes.

In some other embodiments, relatively small conjugate molecules of binding agents, e.g. single antibody molecules or isolated Fab regions of antibodies that are conjugated with one, or two, or more moieties of an enzyme, e.g. HRP, may be preferred. Such binding agents are relatively compact molecules and this may be advantageous for detecting individual units of targets that are "hidden" or masked in a target or in a sample, e.g. individual single target molecules may be masked by other molecules of the surroundings, single target structures can be hidden in a target molecule, or single viral particles may be hard to reach in complicated biological samples comprising cells.

In some other embodiments, large conjugates comprising a binding agent and tens to hundreds enzyme moieties may be preferred. Such binding agents may be advantageous e.g. in cases where very fast target detection is concerned or obtaining large deposits per individual target site is desirable.

A single unit of a target bound (directly or indirectly) to a binding agent comprising an enzyme with oxidoreductase activity, e.g. peroxidase activity, constitutes a single target site of the invention.

In one embodiment, a single target site of the invention comprises a single target unit of a target, at least one primary antibody, or a derivative thereof, and at least one secondary antibody, or a derivative thereof, conjugated with one, two or more enzymes with peroxidase activity, e.g. HRP.

In another embodiment, a single target site may comprise a single unit of a target, at least one primary antibody molecule conjugated with a hapten and an antibody against hapten which are conjugated with one, two or more enzymes with peroxidase activity, e.g. HRP.

In another embodiment, a target site may comprise a single unit of a target, one or more first nucleic acid/nucleic acid analog binding agents specific for the target, and one or more second nucleic acid/nucleic acid analog binding agents specific for the first nucleic acid/nucleic acid analog binding agents.

The above embodiments are not limiting. The invention in other embodiments may relate to any combination of a single unit of any target discussed above with any binding agents discussed above making a target site of the invention.

A single target site of the invention in one embodiment may be a single site of a solid support comprising a single unit of a target labeled with enzymatic activity of the invention, i.e. conjugated directly or indirectly with an enzyme with oxidoreductase activity, or a single unit of recombinant fusion molecule comprising a an enzyme with oxidoreductase activity. In one embodiment an oxidoreductase enzyme may the target per se. correspondingly, a target site in this embodiment may comprises just a single unit of an oxidoreductase enzyme, such as an immobilized moiety of an oxidoreductase enzyme, e.g. HRP or laccase which is immobilized on or within a solid support.

Enzyme Substrates

After incubation with one or more binding agents and formation of target sites of the invention described above, a sample comprising one or more single target sites according to the invention is incubated in an aqueous solution (i). An aqueous solution (i) according to the invention comprises a first substrate of an enzyme associated with a single target site of the invention, wherein said first substrate is a water soluble electron rich organic compound which is (1) capable of generating a stable radical upon a reaction with the enzyme; and (2) capable of cross-linking molecules of a second substrate of said enzyme in the presence of both the enzyme and a peroxide compound, thereby producing a water insoluble polymeric product of said second substrate. An aqueous solution (i) according to the invention also comprises a second substrate of an enzyme associated with a single target site of the invention, wherein said second substrate is a conjugate molecule comprising at least two compounds that are capable of serving as substrates of said enzyme and a detectable label, wherein the detectable label is selected from the group consisting of a fluorescent, luminescent, radioactive or chromogenic matter or a member of a specific binding pair.

First Substrate

A first substrate of an enzyme associated with a single target site of the invention (also termed hereafter as "first substrate") is a substrate of an enzyme with oxidoreductase activity. This substrate (1) is a water soluble electron rich organic compound, (2) is capable of generating a radical upon a reaction with said enzyme, and (3) is capable of cross-linking water soluble molecules of a second substrate of said enzyme (in the presence of said enzyme and a peroxide compound) producing thereby a water insoluble polymeric product of said second substrate.

By the term "water soluble" is meant that molecules of the first substrate are soluble in water and water containing solutions. By the term "electron rich compound" is in the present content means an organic compound that comprises a conjugated system of connected p-orbitals including compounds with alternating single and multiple bonds. Lone pairs and radicals may be part of the system. The compound may be cylic, acyclic or both. By "conjugated" is meant that there is an overlap of one p-orbital with another across an intervening sigma bond (in larger atoms d-orbitals can be involved). A conjugated system has a region of overlapping p-orbitals, bridging the interjacent single bonds. They allow a delocalization of pi electrons across all the adjacent aligned p-orbitals, which in general may lower the overall energy of the molecule and increase stability. The pi electrons of a conjugated system do not belong to a single bond or atom, but rather to a group of atoms.

The group of enzymes with oxidoreductase activity of the invention includes diverse enzymes that can utilize a great number of substrates. Among these substrates, the substrates of the invention are those compounds that are water soluble organic electron-rich organic compounds comprising a conjugated pi-system, which are capable of generating radicals, preferably stable radicals, upon a reaction with an enzyme with oxidoreductase activity of the invention. The term "stable radical" in the present context means that under conditions of the present invention, e.g. in an aqueous solution (i), a radical of the first substrate has a life time of at least 20 seconds, preferably from about 1 minute to about 15 minutes, or longer e.g. 2, 3, 4, or 5 minutes, between 5 and 10 minutes, etc. Further, radicals of compounds that make up the group of the first substrates of the invention are capable of cross-linking water soluble molecules of the second substrate of the invention and thereby converting said water soluble molecules into a water insoluble polymeric product.

In particular, in one embodiment the invention relates to the first substrate which is represented a group of a water soluble organic electron-rich compounds that comprise a group of interconnected carbon atoms, wherein every second bond is a double bond, preferably compounds that comprise a chain of at least three (C—C=) repeats, or compounds comprising an aromatic ring structure.

In one embodiment, the first substrate may be represented by a compound comprising a structure of formula (I):

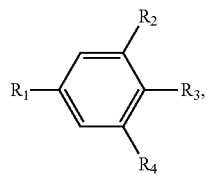

wherein
R1 is an aryl or vinyl,
R2, R3 and R4 is independently H, N—(X)$_2$, O—(X)$_2$, wherein X is an alkyl, vinyl or aryl, or H, and wherein R2, R3 and R4 are not simultaneously H,
wherein.
H is hydrogen;
O is oxygen.

Non-limiting examples of compounds of above formula that have capacity as the first substrate of an enzyme with oxidoreductase activity of the invention may be 3'3'-diaminobenzidine, ferulic acid, alpha-cyano-4-hydroxy-cinnamic acid and derivatives thereof.

In one preferred embodiment the invention relates to 3'3'-diaminobenzidine (DAB) as the first substrate.

The present invention utilizes the capacity of DAB to form a stable radical which can cross-link molecules of the second substrate in the presence of an enzyme with oxidoreductase activity, i.e. horse radish peroxidase (HRP), and a peroxide compound, i.e. hydrogen peroxide, and deposit the cross-linked molecules of the second substrate discretely at single target sites.

In another preferred embodiment, the invention relates to ferulic acid as the first substrate.

Ferulic acid is also capable to cross-link molecules of second substrates of the invention in the presence of an enzyme with oxidoreductase activity, i.e. horse radish peroxidase (HRP), and a peroxide compound, i.e. hydrogen peroxide, and deposit said second substrate discretely at single target sites of the invention.

In some other preferred embodiments the invention may relate to derivatives of 3'3'-diaminobenzidine, ferulic acid. The term "derivative" means in the present content a compound that is derived from 3'3'-diaminobenzidine, ferulic acid or a compound that can be imagined to arise from 3'3'-diaminobenzidine, ferulic acid, if one atom in the latter molecules is replaced with another atom or group of atoms. The invention relates to derivatives of 3'3'-diaminobenzidine, ferulic acid that meet the requirements for the first substrate of the invention discussed above The amount of a first substrate in the aqueous media (i) and/or aqueous media (ii) may vary from around 0.05 mM to around 2 mM, depending on the structure of the compound representing the first substrate. Generally, compounds of formula (I) with R1 being a vinyl or a vinyl derivative, are used in higher amounts, than compounds, wherein R1 is an aryl or its derivative. Thus, DAB serves as the first substrate according to the present invention when its amount in an aqueous solution (ii) is less than 1 mM, preferably within the range of 0.05 mM to 1 mM, such as between 0.05 mM and 0.08 mM, e.g. around 0.07 mM, i.e. from 0.066 mM to 0.074 mM, or between 0.08 mM to 0.1. mM, e.g. around 0.09 mM, or between 0.1. mM and 0.3 mM, e.g. around 0.15 mM, around 0.2 mM, around 0.25 mM, or between 0.3 mM and 0.6 mM, e.g. around 0.35 mM, around 0.4 mM, around 0.45 mM, around 0.5 mM, around 0.55 mM, or between 0.6 mM and 1 mM, e.g. around 0.7 mM, around 0.75 mM, around 0.8 mM, between 0.8 mM and 1 mM. It was surprisingly found that when DAB present at the latter amounts, it is possible to form discrete rounded deposits of the second substrate that are larger than 0.4 micrometer in diameter, such around 1 micrometer, 1.5 micrometers, 2 micrometer or larger, e.g. around 3 or 4 micrometers. To produce such deposits of the second substrate, ferulic acid as the first substrate may present in the aqueous media (ii) in an amount that is between around 1 mM and around 2 mM, such as for example around 1.5 mM.

Second Substrate

According to the invention the second substrate of an enzyme of the invention (also termed herein as "second substrate") is a conjugate molecule comprising at least two compounds that are capable of serving as substrates of said enzyme and a detectable label, wherein the detectable label is selected from the group consisting of a fluorescent, luminescent, radioactive or chromogenic matter or a member of a specific binding pair.

In some preferred embodiments the invention relates to a large group of conjugate molecules as second substrates that share the following features:

1. The conjugate molecules are water soluble molecules comprising two or more substances that can serve as substrates of the enzyme of the invention, preferably as substrates of HRP, and one or more labels wherein the substrates and labels are linked together via a water soluble linker compound (termed hereafter "linker");
2. The enzyme substrate moieties are "concentrated" in the conjugate molecule in one part of said molecule and the labels are "concentrated in another part of said molecule, wherein the label(s) are distanced away from the substrates by approximately 30 consecutively interconnected atoms or more, i.e. separated approximately by 2.5 nm or more, preferably by more than 3 nm
3. The enzyme substrates are separated from each other by a distance that is less than 2.5 nm, e.g. separated within molecule of the conjugate by less than 30 interconnected carbon or heretoatoms, such as carbon, nitrogen, sulphur and/or oxygen atoms or less, preferably not more than 5-20 atoms;
4. The linker is a compound which comprises at least 30 consecutively connected atoms;
5. The conjugates do not precipitate from an aqueous solution (ii) containing a peroxide compound and a first substrate of the invention in the absence in the environment of an enzyme with oxidoreductase activity.
6. The conjugates do not precipitate from an aqueous solution (ii) containing a peroxide compound in the presence of an enzyme with oxidoreductase activity and in the absence the first substrate of said enzyme in the environment.
7. The conjugates precipitate from an aqueous solution (ii) containing a peroxide compound and a first substrate of an enzyme with oxidoreductase activity of the invention in the presence of said enzyme in the environment.

Deposits of the second substrate may be directly detectable by visual means because they, in some embodiments, may comprise a chomogenic, fluorescent or luminescent label. In other embodiments the precipitated second substrate may be "stained" in steps following the deposition to be visible. In both cases, the deposits of the second substrate will "report" to the observer the presence a single target site of the invention in the surroundings. The molecules of second substrate of the invention are thus interchangeably termed herein "reporter" molecules.

Non-limiting embodiments of second substrate molecules are described in detail below and in EXAMPLES.

In one embodiment the invention relates to a second substrate which is a water soluble conjugate molecule that comprises (i) one or more detectable substances (termed interchangeably "label")

(ii) at least two substances, which are capable of serving as substrates of the enzyme of the invention, and (iii) a linker
   wherein
   said linker is a compound comprising at least one linear chain consisting of at least 30 consecutively connected atoms that contains at least two branching points, wherein said brunching points are separated by a molecular distance of at least 30 consecutively connected atoms;
   wherein
   the labels (i) and oxidoreductase substrate moieties (ii) are attached to the linker at its two branching points that are separated by a distance of at least 30 consecutively connected atoms, and
   wherein
   any two neighboring enzyme substrates are separated from each other by a molecular distance that is less than 30 consecutively interconnected atoms The term "detectable substance" means that the substance can give off a detectable chromogenic, fluorescent, luminescent or radioactive signal be detected by visual means, or it can be detected using its specific binding partner, e.g. an antibody, nucleic acid sequence, nucleic sequence analog sequence, hapten, antigen, receptor, receptor ligand, enzyme, etc.

In some embodiments a water soluble conjugate molecule of the invention may additionally comprise moieties that may enhance its features, e.g. improve its capacity as the label or enzyme substrate, or increase/reduce its water solubility.

In one embodiment, conjugate molecules of the invention may be selected from a group of compounds of formula (II):

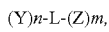

wherein

Y is a moiety capable of serving as substrate of an enzyme with oxidoreductase activity;

Z is a detectable label;

L is a linker compound wherein n is an integer from 2 to 150, and m is an integer from 1 to 150

In one preferred embodiment Y is selected from compounds of the following formula (II):

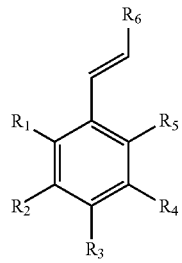

wherein
R1 is —H, —O—X, N(X)$_2$ or —S—X;
R2 is —H, —O—X, —N(X)$_2$, or —S—X,
R3 is —H, —OH, —NH$_2$ or —SH;
R4 is —H, —O—X, —N(X)$_2$, or —S—X,
R5 is —H, —O—X, N(X)$_2$, or —S—X,
R6 is —CON(X)$_2$, or CO—X,
wherein
   H is hydrogen;
   O is oxygen
   S is sulphur
   N is nitrogen, and
   X is H, alkyl or aryl.

In one embodiment at least one of the compounds that are capable of serving as substrate of an enzyme with oxidoreductase activity is a compound of formula (ii).

In one embodiment at least two of the compounds that are capable of serving as substrate of an enzyme with oxidoreductase activity in the conjugate molecule are compound of formula (ii).

In one embodiment at least two of the compounds that are capable of serving as substrate of an enzyme with oxidoreductase activity in the conjugate molecule are identical compounds of formula (ii).

In one embodiment at least two of the compounds that are capable of serving as substrate of an enzyme with oxidoreductase activity in the conjugate molecule are different compounds of formula (ii).

In one embodiment all compounds that are capable of serving as substrate of an enzyme with oxidoreductase activity in the conjugate molecule are defined by formula (II). In one embodiment these are identical compounds, in another embodiment the conjugate molecule comprises any combination of different compounds defined by formula (II).

In one preferred embodiment Y may be a residue of cinnamic acid; in another preferred embodiment Y may be a residue of ferulic acid. In another preferred embodiment Y may be a residue of caffeic acid; in another preferred embodiment Y may be a residue of amino cinnamic acid. In another preferred embodiment Y may be a residue of sinapinic acid. In another preferred embodiment, Y may be a derivative of ferulic acid, cinnamic acid, caffeic acid, amino cinnamic acid or sinappinic acid.

Preferably a residue Y defined by the formula (II) is connected to a linker L via group R6.

In one preferred embodiment the conjugate comprises two to four identical residues Y. In another preferred embodiment the conjugate comprises a combination of two to four different residues Y. In one preferred embodiment the two to four residues Y are compounds defined the formula (II).

In one preferred embodiment, the conjugate may comprise two to four residues ferulic acid or residues of derivatives thereof, in another embodiment the conjugate may comprise two to four residues cinnamic acid or residues of derivatives thereof; in another embodiment the conjugate may comprise two to four residues of caffeic acid or residues of derivatives thereof; in another embodiment the conjugate may comprise two to four residues amino cinnamic acid; in another embodiment the conjugate may comprise two to four residues sinapinic acid or residues of derivatives thereof. The two to four derivatives of the latter compounds may be the same compound or may be different compounds.

In one preferred embodiment a conjugate molecule may comprise two Y compounds of formula (II), or two derivatives thereof, e.g. two ferulic acid residues, or two cinnamic acid residues, or two amino cinnamic acid residues, or two caffeic acid residues, or two sinapinic acid residues, etc. and one or more detectable labels; in another embodiment the conjugate may comprise three molecules of formula (II) or three derivatives thereof, such as three ferulic acid, cinnamic acid, caffeic acid, amino cinnamic acid, sinapinic acid, etc., and one or more detectable label; in another embodiment the conjugate may comprise four compounds of formula (II) or four derivatives thereof, e.g. four ferulic acid, cinnamic acid, caffeic acid, amino cinnamic acid, sinapinic acid, or four derivatives the latter, and one or more detectable labels.

In some embodiments the number of Y compounds may be higher than 4, e.g. such as 5-10, 10-15, 15-20, 20-50, 50-100, or 100-150 compounds. Non-limiting examples of such conjugate molecules are described in Examples. In some preferred embodiments such conjugates may comprise more than one linear chain of at least 30 consecutively connected atoms, e.g. 30-150 atoms, wherein two to four Y compounds are attached to each linear chain at first and the same branching point of the chain, and several of such linear chains are linked to another water soluble linker molecule, e.g. a dextran, via a second (another) branching point of said linear chains.

In one preferred embodiment, a conjugate molecule may comprise a combination of two or four different compounds of formula (II), or a combination of two or four derivatives thereof, e.g. two ferulic acid residues and one cinnamic acid residue, two sinapinic acid residues and two caffeic acid residues, etc.

In one preferred embodiment Y may be a residue of amino acid tyrosine or residue of a derivative thereof. A conjugate may comprise 2 to 4 or more such residues.

In one embodiment conjugate molecule may comprise a combination of substrates of the enzyme with oxidoreductase activity, wherein at least one of said substrates is tyrosine. In one embodiment the conjugate molecule comprises at least one tyrosine residue and at least one compound of formula (II), or a derivative thereof. and at least one another is a compound of formula (II) a derivative thereof, e.g. one tyrosine residues and two residues of sinapinic acid or derivatives thereof.

In some embodiments it may be preferred that the conjugate comprises 4 to 6 residues Y, wherein Y is represented by any compound or a combination of any compounds as described above.

According to the invention, Y compounds are located in a conjugate molecule as a group, preferably grouped as two to four Y compounds per group, (i.e. a conjugate comprising more than four Y compounds may comprise several groups of two to four Y compounds, wherein said groups are separated in the conjugate molecule by a group of atoms, e.g. by a molecular distance corresponding to 30 connected atoms or more). Preferably, the two to four Y compounds in such groups are linked together via a spacer compound that provides a distance between two neighboring Y residues which is not longer than 5-15 interconnected atoms, e.g. 5-10, 6-12, 7-13, 8-14, 9-15, etc., For example, 2-4 Y compounds may be attached to amino acids making up a peptide chain comprising 2 to 4 amino acid residues, e.g. residues of lysine, serine, cystein, etc., wherein the Y compounds are attached to reactive groups of the amino acid residues of the peptide, e.g. to the epsilon amino groups of lysine residues. Two to four compounds Y may also be connected to each other via other short polymers which comprise a number of brunching points, wherein a molecular distance between these branching points corresponds to a chain of not more than 3-7 atoms, preferably 3-5 atoms, wherein the Y compounds may be directly indirectly linked to said branching points. Two to four compounds Y may also be grouped together being conjugated to a non-polimeric molecule that have two to four reactive groups allowing attaching any two to four Y compounds. Such grouped location of Y compound is termed thereafter "Y-head" of the conjugate molecule.

In one preferred embodiment, the Y-head comprises two to four Y-residues linked via a short polymer, e.g. a short PNA molecule or a short peptide, wherein the peptide, preferably, comprises lysine, serine glutamate and/or cystein residues. However, any other polymeric or non-polimeric water soluble molecules that comprise 15 or less atoms that can be conjugated with at least two Y-residues and a linker L may be suitable.

In one embodiment one Y-head comprising two to four compounds Y may be linked to a polymer comprising two or more repeats of the following formula (III)

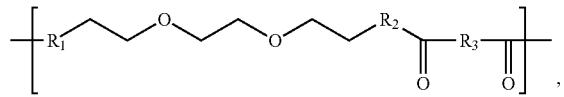

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups. The resulting conjugate may be further conjugated with one (or more) detectable label, or it may be conjugated with another water soluble molecule which comprises one or more reactive groups allowing attaching one or several such conjugates. One non-limiting example of such water soluble molecule may be a dextran polymer.

Close spacing of Y compounds in conjugate molecules has influence on functional capacity of the conjugates as second substrates of the invention, namely the conjugates remain soluble in aqueous solutions containing a peroxide compound and 3,3'-diaminobenzedine (DAB) in the absence of an enzyme with oxidoreductase activity in the environment, but rapidly and efficiently precipitates from such solutions when an enzyme with oxidoreductase activity presents in the environment (compared to conjugates that comprise only one Y compound or comprise several Y compounds that are not "concentrated" in the conjugate molecule in form of an Y-head, i.e. molecular space between two neighboring Y residues is larger than the discussed above distance. Such compounds are not efficient to form discrete deposits at single target sites of the invention).

The detectable label of a conjugate molecule may be any substance which can be visually detected, e.g. a fluorescent or luminescent substance, or any substance that can be detected by using some detecting means, e.g. a radioactive label, a member of a specific binding pair, e.g. a nucleic acid sequence, hapten, etc.

Any fluorescent, luminescent, bioluminescent or radioactive molecules may be used as the labels. Many of them are commercially available, for example fluorescent stains Alexa Fluors (Molecular Probes) and DyLight Fluors (Thermo Fisher Scientific). Other non-limited examples of fluorescent labels may be the following molecules: 5-(and 6)-carboxyfluorescein, 5- or 6-carboxyfluorescein, 6-(fluorescein)-5-(and 6)-carboxamido hexanoic acid, fluorescein isothiocyanate, rhodamine, tetramethylrhodamine, Cy2, Cy3, Cy5, AMCA, PerCP, R-phycoerythrin (RPE) allophycoerythrin (APC), Texas Red, Princeton Red, Green fluorescent protein (GFP) coated CdSe nanocrystallites, ruthenium derivatives, luminol, isoluminol, acridinium esters, 1,2-dioxetanes and pyridopyridazines, radioactive isotopes of hydrogen, carbon, sulfur, iodide, cobalt, selenium, tritium, or phosphor.

In some embodiments the detectable label may be an enzyme. Non-limiting examples of suitable enzyme labels may be alkaline phosphatase (AP), beta-galactosidase (GAL), glucose-6-phosphate dehydrogenase, beta-N-acetyl-glucosaminidase, β-glucuronidase, invertase, xanthine oxidase, firefly luciferase, glucose oxidase (GO).

In other embodiments, the detectable label may be a member of a specific binding pair, e.g. a hapten. As non-limiting examples of suitable haptens may be mentioned 2,4-dinitrophenol (DNP), digoxiginin, fluorescein, Texas Red, tetra methyl rhodamine, nitrotyrosine, acetylaminofluorene, mercury trintrophonol, estradiol, bromodeoxy uridine, dimethylaminonaphthalene sulfonate (dansyl), amino acids tyrosine, serine, etc. As examples of suitable specific binding pairs may also be mentioned biotin, streptavidin, complementary natural and non-natural oligonucleotide sequences, zink fingers binding domain pairs, etc. Other examples are discussed above.

In one preferred embodiment the label is a hapten. In another preferred embodiment, the label is a fluorescent substance. In another preferred embodiment, the label is a member of a specific binding pair. Other labels may be preferred in other embodiments.

The number or detectable labels per conjugate molecule (as any of the described above) may vary. In some embodiments the number of labels may be from 1 to 3, for example 1, 2 or 3 labels per conjugate molecules. In some other embodiments, the conjugate may comprise more from 4 to 150 labels per conjugate molecule.

In one preferred embodiment a conjugate (as any of the described above) comprises one detectable label. In one preferred embodiment a conjugate molecule may comprise one Y-head (as any of the discussed above) and one label.

According to the invention, in a conjugate molecule the detectable substance (a single label or a plurality thereof) is separated from the compounds that are substrate of an enzyme with oxidoreductase activity, e.g. from an Y-head, by a molecular distance of more than 2.5 nm, e.g. separated by a chain of at least 30 consecutive atoms, e.g. 30-150 or more consecutive atoms. In embodiments where the conjugate comprises one chain of connected atoms as L linker between an Y-head and 1 (or more) labels, the Y-head and the label(s) are linked to said chain at branching points located at least 30 atoms apart from each other, e.g. on the opposite ends of a chain of 30 connected atoms.

In some embodiments, when a conjugate comprises more than 1 label, it is preferred that the labels are grouped so that there is a molecular distance between the labels, that correspond to a chain of at least 30 consecutively connected atoms (termed "spacer"), preferably 60 consecutively atoms or more, e.g. 90 consecutively interconnected atoms. It is preferred that the spacer between the labels is a hydrophilic compound. The latter group of labels is then attached to a linker compound linking said labels and enzyme substrate moieties in a conjugate molecule in the way described above, i.e. a label of the group that is positioned closest to the Y-head is distanced away from any of the enzyme substrates of the Y-head by at least 30 interconnected atoms, i.e. by at least 2.5 nm distance. Such arrangement of multiple labels in a conjugate molecule is termed thereafter "Z-tail".

Preferably, a spacer of at least 30 consecutive atoms between labels of a Z-tail is a polymeric compound comprising two or more repeats of the following formula (III)

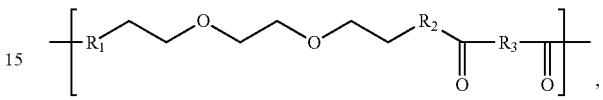

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Multiple labels attached to and separated by the above spacer may be conjugated with one Y-head or several Y-heads via any suitable linker, e.g. water soluble polymers allowing multiple attachments, e.g. dextran. In some embodiments several Y-heads may be conjugated with several Z-tails via such polymer.

In one embodiment multiple labels of a conjugate molecule of the invention may be same detectable substances, in another embodiment the labels may be different detectable substances.

The Z-tail arrangement of labels has advantages in that (1) conjugates comprising multiple hydrophobic labels remain good solubility in water solutions, and (2) the labels are better accessible for binding agents, when binding agents are used to detect the deposited conjugates.

The linker between oxidoreductase substrates and labels (e.g. between Y head and Z tail), L, is according to the invention a molecule that comprises a chain of at least 30 contiguous atoms, such as 30-150 atoms or more, e.g. 30, 45, 60, 90, 150, 300, 500 atoms or more. In one preferred embodiment preferably, L comprises 150 contiguous atoms. In some embodiments, a linker molecule comprises a linear chain of atoms wherein every two connected carbon atoms are followed by an atom of oxygen or nitrogen.

In one preferred embodiment L may be a single linear polymer molecule; in another preferred embodiment L may be a conjugate molecule which may comprise several different polymers conjugated together.

In one preferred embodiment L is a linear polymer that comprises a chain of atoms wherein two consecutive carbon atoms are followed by a heteroatom selected from oxygen or nitrogen, e.g. such as a linker comprising described below, or polyethylene glycol, etc.

In another preferred embodiment the linker is a compound comprising two or more repeats of the following formula (III)

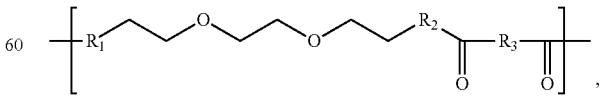

wherein $R_1$ and $R_2$ are selected from NH and O, and $R_3$ is selected from methyl, ethyl, propyl, $CH_2OCH_2$, and $(CH_2OCH_2)_2$, and wherein no more than three consecutively repeating ethyloxy groups.

Preferably, L comprises at least two repeats of the above formula wherein both R1 and R$_2$ are NH and R$_3$ is CH$_2$OCH$_2$. Preferably, L comprises one or more repeats of the following formula (IV)

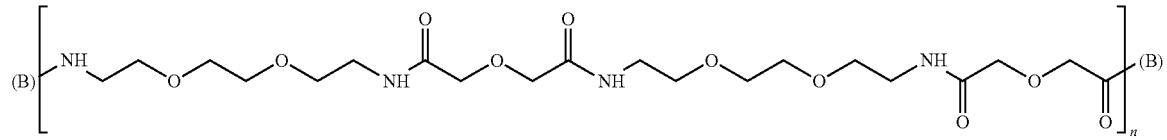

wherein n is an integer from 1 to 10, and (B) is a branching point. The L molecules of this formula and their synthesis are in detail described in WO2007/015168, which is incorporated herein by reference.

By the term "branching point" is meant a point in a polymer molecule wherein a branch, e.g. a side chain of the same polymer, or other molecules may be attached. The branching point may be an atom, a group of atoms, or a functional group via which compounds Y and Z may be directly or indirectly conjugated to L.

There is a great variety of polymer molecules that may be used as linker L. Examples include polysaccharides such as dextrans, carboxy methyl dextran, dextran polyaldehyde, carboxymethyl dextran lactone, and cyclodextrins; pullulans, schizophyllan, scleroglucan, xanthan, gellan, O-ethylamino guaran, chitins and chitosans such as 6-O-carboxymethyl chitin and N-carboxymethyl chitosan; derivatized cellolosics such as carboxymethyl cellulose, carboxymethyl hydroxyethyl cellulose, hydroxyethyl cellulose, 6-amino-6-deoxy cellulose and O-ethylamine cellulose; hydroxylated starch, hydroxypropyl starch, hydroxyethyl starch, carrageenans, alginates, and agarose; synthetic polysaccharides such as ficoll and carboxymethylated ficoll; vinyl polymers including poly(acrylic acid), poly(acryl amides), poly(acrylic esters), poly(2-hydroxy ethyl methacrylate), poly(methyl methacrylate), poly(maleic acid), poly(maleic anhydride), poly(acrylamide), poly(ethyl-co-vinyl acetate), poly(methacrylic acid), poly(vinylalcohol), poly(vinyl alcohol-co-vinyl chloroacetate), aminated poly(vinyl alcohol), and co block polymers thereof; poly ethylene glycol (PEG) or polypropylene glycol or poly(ethylene oxide-co-propylene oxides) containing polymer backbones including linear, comb-shaped or hyperbranched polymers and dendrimers, including branched PAMAM-dendrimers; poly amino acids including polylysines, polyglutamic acid, polyurethanes, poly(ethylene imines), pluriol; proteins including albumins, immunoglobulins, and virus-like proteins (VLP), and polynucleotides, DNA, PNA, LNA, oligonucleotides and oligonucleotide dendrimer constructs; mixed polymers, i.e., polymers comprised of one or more of the preceding examples of polymers, co-block polymers and random co-polymers.

Properties of the chosen polymer can be modified to optimize performance, e.g. the length or branching can be optimized. Furthermore, the polymer may be chemically modified to carry various substituents. The substituents may be further chemically protected and/or activated, allowing the polymer to be derivatized further.

In one preferred embodiment the linker compound between oxidoreductase substrates and labels is a dextran polymer or a conjugate molecule comprising a dextran polymer.

Methods of conjugating polymers with different chemical substances, e.g. labels, are well known in the art and can be used to make conjugates of the invention. For example, the polymer may be activated with vinylsulfon and mixed with a detectable label and a molecule of formula (II) to form the polymer conjugate. In other embodiments, aldehydes can be used to activate a polymer, e.g. dextran, which is then mixed with a detectable label and a molecule of formula (II). Yet another method of preparing polymeric conjugates is by using so called chemo selective coupling schemes for coupling the components together, e.g. molecules can be derivatized with thiol reactive maleimide groups before being covalent coupled to an thiol modified polymeric backbone. In some other embodiments, a molecule for formula (I) and a detectable label can be attached to the polymer via a linking compound. Examples of this method include the use of homobifunctional linker compounds such as glutaric dialdehyde, hexan di isocyanate, dimethylapimidate, 1,5-difluoro-2,4-dinitrobenzene, heterobifunctional cross binders like e.g. N-gamma-maleimidobytyroloxy succinimide ester, and zero length cross binders such as 1-ethyl-3-(3-dimethylaminopropyl)cabodiimide.

Methods of derivatization of polymers comprising one or more repeats of formula (III) (termed hereafter "L30") are described in detail in WO2007/015168, which is incorporated herein by reference.

Exemplary conjugates comprising linkers that are polymers comprising various number of repeats of formula (III), such as a polymer comprising two L30 repeats, (termed L60), such as a polymer comprising three L30 repeats (termed L90), such as a polymer comprising five L30 repeats (termed L150) are described in EXAMPLES.

The amount of the second substrate in the aqueous media (ii) may vary from about $10^{-10}$ M to about $10^{-4}$ M, for example, in case a conjugate (as any of the described above) comprises a radioactive label, the applicable amount may be from about $10^{-10}$ M to about $10^{-6}$ M, and from about $10^{-9}$ M to about $10^{-4}$ M, in case a conjugate comprises a fluorescent label or a label which is a member of a specific binding pair.

Incubation Media

In one embodiment a sample comprising single units of a target is incubated during a visualization procedure according to the invention in different aqueous media (collectively termed herein "incubation media").

The term "incubation media" means in the present context an aqueous solution where the sample is maintained during a certain period of time (termed herein "incubation time") in order to achieve results of a desirable reaction.

Time for maintaining/incubating the sample in an incubation medium, i.e. incubating time, may vary depending on the technical effect which is desired to be achieved following the incubation. In different embodiments an incubation may lasts from approximately 3 seconds to approximately 3 min, e.g. around 10 seconds, 20 seconds, 30 seconds, 1 minute, 2 minutes, 5 minutes, 10 minutes. or longer, e.g. one-two hours, overnight. In one embodiment, incubating time at all steps of the method may have the same duration, i.e. every incubating may lasts 5 to 10 minutes, etc. In another sample in an aqueous solution comprising a binding agent (termed hereafter "binding agent solution") may lasts 1-3 minutes, incubating in an aqueous media (i) and/or aqueous solution (ii) media may lasts 10 minutes.

Incubating may be performed at various temperatures, depending on the type of target, binding agent, etc. The procedures according to the invention are substantially temperature independent and can be performed at a temperature from around +4 C.° to around +40 C.°, however, if desired, the temperature may be used for extending or reducing duration of an incubation, e.g. lower temperatures may be used to prolong the incubating time, and, vice versa, higher temperatures may be used to shorten the time for incubating.

Non-limiting embodiments of compositions of incubation media are discussed below.

Binding Agent Media

On step (a) of the methods of the invention a sample is incubated with one or more binding agents as described above. Accordingly, in one embodiment, the invention relates to an aqueous solution comprising a binding agent, such as e.g. a binding agent comprising an enzyme with oxidoreductase activity. This medium is termed herein "binding agent medium".

One desired technical effect to be achieved due to incubation of the sample in such media is to form target sites according to the invention. Accordingly, the binding agent medium is an aqueous medium, in which the chosen binding agent is soluble and is capable of binding to a single target unit. Basically, the binding agent medium is a buffered aqueous solution of one or more binding agents that has pH in the range from 4 to 9. In some embodiments the binding agent medium may comprise an organic or inorganic salt. The inorganic salt may be selected form e.g. sodium chloride, magnesium chloride, potassium chloride, calcium chloride, sodium phosphate, or ammonium sulfate. The organic salt may be selected from e.g. sodium acetate, ammonium acetate or imidazole salts, e.g. imidazole hydrochloride, etc.

The amount of salt in binding agent media may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

As mentioned, typically, the pH value of binding agent mediua may vary from about 4 to about 9, such as between pH 3.5 and pH 9.5, e.g. between pH 5 and pH 7, between pH 5.5 and pH 6.5 or between pH 6.5 and 7.5, or between pH 7 and pH 8, or between pH 7.5 and pH 8.5, or pH 8 and pH 9. Any buffer with a suitable buffer capacity may be used, e.g. phosphate buffered saline (PBS) and imidazole buffer. Other suitable buffers may be found in Good, N E., et al (1966) Hydrogen ion buffers for biological research. Biochem. 5(2), 467-477. The pH value of the media may be essential for binding of binding agent to the target; it may be optimized depending on the nature of the binding agent and the target.

In some embodiments the binding agent medium may comprise an organic modifier (by the term "organic modifier" is meant any non water solvent), e.g. N-Methyl pyrolidone (NMP), dimethylsulphoxide (DMSO), mono- and diethylene glycol, sulpholane, N,N-dimethylformamide (DMF), polyethylene glycol (PEG), propylene glycol, etc. The amount of the organic modifier may vary from around 1% to around 20% (v/v or w/v), or, in some embodiments, be higher than 20%.

In some embodiments the binding agent medium may comprise a detergent, e.g. polyethylenglycol-p-isooctyphenyl ether (NP-40)) or a surfactant (e.g. selected from the surfactants based on polyoxyethylene sorbitanmonolaurate (Tween), or a surfactant based on block copolymers (pluronic etc.), etc. The amount of the detergent may vary from about 0.001% to about 5%/v/v or w/v).

In some embodiments the binding agent medium may comprise a binding agent stabilizing agent, e.g. bovine serum albumin or dextran. The amount of the stabilizing agent may vary from 0.01% to 20% (w/v).

In some embodiments the binding agent medium may comprise an ion chelator (e.g. ethylene diamine tetra acetic acid (EDTA) or ethylene diamine hydroxyl phenylacetic acid type chelator (EDHPA), etc.). The amount of the chelator may vary from about $10^{-9}$ M to about $10^{-6}$ M.

In some embodiments, the binding agent medium may comprise one or more blocking agents for saturating non-specific binding sites, i.e. sites of the solid support that do not comprise the target. Some non-limiting examples of blocking agents suitable for different embodiments may be the Denhard's solution, bovine serum albumin, skimmed milk, etc.

As discussed above, the invention contemplates a great variety of species of targets, binding agents and assay formats, accordingly, composition of the binding agent medium may vary and should be adjusted for every particular embodiment using the knowledge of the art. Some non-limited examples of the binding agent medium are described in EXAMPLES.

In one embodiment, when a sample comprise a target that present in a low concentration range it may be preferred to use relatively high amounts of binding agents in a binding agent media which content (e.g. pH, salt concentration, etc) and incubation conditions (e.g. duration of incubation, temperature) are optimized to facilitate interaction between the binding agents and the target. Such optimization is to secure binding of maximal number of single units of the target with the binding agents and formation of maximal number of discrete single target sites. In this embodiment, due to a low expression of a target in the sample, a significant number of overlaps between single target sites is not expected.

In one embodiment, when the sample comprise a target that present at a low concentration range it may be preferred to use relatively high amounts of binding agents in a binding agent media which content (e.g. pH, salt concentration, etc) and incubation conditions (e.g. duration of incubation, temperature) is optimized to facilitate interaction between the binding agents and the target. Such optimization is to secure binding of maximal number of single units of the target with the binding agents and formation of maximal number of discrete target sites. In this embodiment, due to a low expression of a target in the sample, it is not expected a significant number of overlaps between single target sites.

In one preferred embodiment, the quantity of binding agents in the binding media is adjusted to bind all or a substantial majority of available single target units present in the sample and form discrete single target sites with them.

In another embodiment, when a target is abundantly expressed in the sample, the amount of one or more binding agents in the medium, e.g. the first, second, and/or third binding agent, is to be adjusted so that the binding agents will capable of forming discrete single target sites only with a fractional subpopulation of single units in the sample. Alternatively, in such embodiments, composition of a binding agent medium such as pH, salt content, etc., or incubating conditions, such as temperature etc, may be adjusted so that they affect target binding capability of one or more binding agents involved in formation of single target sites and the binding agents will therefore form the target sites only with a fractional subpopulation of single units of the target present in the sample.

Thus, in one embodiment, a sample comprising a target that is expressed abundantly or in a broad dynamic concentration range is incubated in a binding agent media under conditions wherein the binding agents are capable of forming discrete single target sites with a fractional subpopulation population of single target units. The term "fractional subpopulation" in the present context is defined a portion of the total population that is equal or less than 99%. e.g. equal or less than 90% of the total quantity of single units of the target in the sample, such as less than 85%, e.g. 75-80% of the total quantity of units of the target in the sample, such as less than 75%, for example from 1% to 50% of the total quantity of single units of the target in the sample, such as. from 1% to 25% of the total quantity of units of the target in the sample, etc. In one embodiment, incubation conditions may be adjusted so that the binding agents will form discrete single target sites with a fractional subpopulation of single target units that is less than 1% of the total quantity of single units of the target present in the sample, such as from about 0.1% to about 1%.

Aqueous Solutions (i)

Following the incubation in a binding agent medium, the sample is incubated in an aqueous solution (i) comprising a first substrate of the enzyme with oxidoreductase activity and, a second substrate of the enzyme with oxidoreductase activity and a peroxide compound.

Optionally, before the incubation in the aqueous solution (i), the sample may be incubated in an aqueous solution (ii), which is an aqueous solution (i) that lacks the second substrate.

Accordingly, in one embodiment the invention relates to incubation media which is in an aqueous solution (i) and in another embodiment the invention relates to incubation media which is an aqueous solution (ii).

Both aqueous solution (i) and aqueous solution (ii) may be an aqueous buffered solution with a suitable buffer capacity, e.g. phosphate buffered saline (PBS) and imidazole buffer. Other suitable buffers may be found in Good, N E., et al (1966) Hydrogen ion buffers for biological research. Biochem. 5(2), 467-477. The pH value of the solutions may be adjusted in order to achieve the technical effect of the incubation, namely formation of discrete deposits of the second substrate of an enzyme with oxidoreductase activity at discrete single target sites of the invention, for example adjusted to pH ranging from about 4 to about 9. However, pH of the aqueous solutions (i) and (ii) is of minor importance for the technical effect of the incubation.

Both aqueous solution (i) and aqueous solution (ii) may further comprise an organic or inorganic salt.

The inorganic salt may be selected form e.g. sodium chloride, magnesium chloride, potassium chloride, calcium chloride, sodium phosphate, or ammonium sulfate, etc.

The organic salt may be selected form e.g. sodium acetate, ammonium acetate or imidazole salts, e.g. imidazole hydrochloride, etc.

The amount of salt in an aqueous solution (i) and aqueous solution (ii) may range from approximately $10^{-3}$ M to saturation, e.g. from approximately 20 mM to approximately 200 mM, or from approximately 50 mM to approximately 500 mM. In one preferred embodiment, the media may comprise salt in the amount from approximately 10 mM to 500 mM. In another preferred embodiment the medium may be free of salt.

Both aqueous solutions (i) and aqueous solutions (ii) may in different embodiments further comprise:
(i) an organic modifier and/or
(ii) an enzyme enhancer, and/or
(iii) an iron chelator, and/or
(iv) a detergent, and/or
(v) an anti-microbial agent The organic modifier may be present in the media in the amount from around 1% to around 20% (v/v or w/v), however, in some embodiments higher concentrations of the organic modifier may be required. The organic modifier may for example be polyethylene glycol (PEG). Other examples include but not limited to organic modifiers selected from the group essentially consisting of C1-C4, i.e. lower, alcohols, N-Methyl pyrolidone (NMP), dimethylsulphoxide (DMSO), mono- and diethylene glycol, sulpholane, N,N-dimethylformamide (DMF). In some embodiments it may be advantageous to use polyethylene glycol (PEG), e.g. PEG2000, or propylene glycol. The amount of polyethylene glycol in the media in these cases may vary from about 0.1% (v/v) to about 20% (v/v), for example from about 1% (v/v) to about 15%, such as 5-10% (v/v).

By the term "enzyme enhancer" is meant any compound which enhances the catalytic activity of peroxidase. Such enzyme enhancer may be selected from the group essentially consisting of phenylboronic acid derivatives and divalent metal ions such as nickel or calcium. The amount of the enzyme enhancer may vary from about $10^{-7}$ to about $10^{-3}$ M.

The iron chelator may be ethylene diamine tetra acetic acid (EDTA) or ethylene diamine hydroxyl phenylacetic acid type chelator (EDHPA). Concentration of the iron chelator may vary from about $10^{-9}$ to about $10^{-6}$ M.

The detergent may be selected from polyethylenglycol-p-isooctyphenyl ether (NP-40), a surfactant selected from the surfactants based on polyoxyethylene sorbitanmonolaurate (Tween), or a surfactant based on block copolymers (pluronic etc.). Concentration of the detergent may vary from about 0.001% to about 5%.

Essential components of an aqueous solution (i) are a first substrate of an enzyme with oxidoreductase activity, a second substrate of said enzyme and a peroxide compound.

Embodiments of the first substrate and the second substrates are discussed in detail above.

In one preferred embodiment the first substrate may be 3,3"-diaminobenzidine (DAB) or a derivative thereof. In another preferred embodiment, the first substrate may be ferulic acid or a derivative thereof.

The amount of the first substrate in an aqueous solution (i) may vary depending on the compound chosen as the first substrate (see discussion above). For example, in embodiments, when DAB is chosen as the first substrate, the amount of DAB in an aqueous solution (ii) and in aqueous solution (ii) is less than 1.4 mM, preferable less than 1.2 mM, preferably less than 1 mM, such as from around 0.005 mM to around 0.5 mM, for example around 0.3 mM, or around 0.2 mM, such as around 0.15 mM, etc. In embodiments when ferulic acid is used as the first substrate, the amount of said compound is less than 2.5 mM, preferably less than 2 mM, e.g. around 1.5. mM. The term "around" in the present context means +/−0.05-0.5 mM.

The aqueous solution (i) may comprise various amounts of the second substrate of the enzyme, such as from about $10^{-10}$ M to about $10^{-4}$ M. For example, in embodiments when the second substrate (as any of the described above) comprises a radioactive label, an applicable amount may be in the range from about $10^{-10}$ M to about $10^{-6}$ M. In other embodiments, e.g. when the second substrate comprises a fluorescent label or a label which is a member of a specific binding pair, the amount may be in the range from about $10^{-9}$ M to about $10^{-4}$ M.

In one embodiment, an aqueous solution (i) may comprise a population of identical conjugate molecules of second substrate. In another embodiment, an aqueous solution (i) may comprise a population of different conjugate molecules of second substrate.

A preferred peroxide compound of the invention is hydrogen peroxide, however, other peroxide compounds may also be used in different embodiment, e.g. in some embodiments it may be preferred an organic peroxide such as e.g. tert-butyl peroxide, ditert-butyl peroxide, peracetic acid, etc, or in some embodiments it may be an adduct of hydrogen peroxide, such as hydrogen peroxide urea adduct.

The amount of a peroxide compound in an aqueous solution (i) and an aqueous solution (ii) may not be higher than 5 mM, preferably less than 5 mM, preferably in the range of 0.1 mM to 5 mM, e.g. between 0.1 mM and 1 mM, between 1 mM and 2 mM, between 2 mM and 3 mM, or between 3 mM and 4 mM, preferably in the range between from around 1 mM to around 2 mM, such as around 1.5 mM. The term "around" in the present context means+/−0.05-0.5 mM An aqueous solution (i) comprising a first substrate of enzyme with oxidoreductase activity, a second substrate of said enzyme and a peroxide compound is termed herein "deposition medium".

An aqueous solution (ii) may comprise the same compounds in the same amounts as an aqueous solution (i), with the exception that the aqueous solution (ii) does not comprise the second substrate of enzyme with oxidoreductase activity.

In some embodiment a sample comprising single target sites may be initially incubated in an aqueous solution (ii) and sequentially in an aqueous media (i).

In another embodiment a sample comprising single target sites is incubated an aqueous solution (i), without preincubation in an aqueous solution (ii).

According to the invention the deposition media is a stable solution, i.e. no precipitation of the solved compounds occurs for a relatively long period of times, such as at least 5 hours. To prolong the shelf-life of the media it may be useful to store the media at temperatures below +20° C., e.g. at +4-+10° C., and/or to add to the media an anti-microbial compound. The anti-microbial compound may be any anti-microbial compound commonly used for such purpose, e.g. sodium azid, Proclin™ or Bronidox®.

Detection Media

In one embodiment the invention relates to a method comprising one or more steps following the step (b) which comprise detection of discrete single deposits of the second substrate at single target sites, e.g. a sample comprising discrete deposits of the second substrate may be incubated in incubation media comprising a binding agent capable of specifically binding to a detectable label of the deposited molecules of second substrate.

An incubation medium comprising a binding agent capable of specifically binding to a detectable label of the deposited molecules of second substrate will typically have a similar or the same composition as the binding agent medium discussed above.

The binding agent bound to a detectable label of the deposited second substrate may in one embodiment comprise an enzyme, e.g. horse radish peroxidase (HRP) or alkaline phosphotase (AP). Such binding agent can be detected using a standard visualization system employing chromogenic substrates of the enzymes, e.g. an enzyme substrate solution or a color developing solution. This kind of media may be any suitable media known in the art which is to be selected depending on available means for visualization and following the common general knowledge of the art concerning the nature of the detectable label of the deposits. Non-limiting examples of such detection are described in EXAMPLES.

Alternatively, in case the binding agent comprises HRP, the visualization method of the invention may comprise a further step of incubation of a sample comprising discrete deposits of the second substrate bound to said binding agent in the deposition media described above. Such further step may be advantageous in some embodiments when a signal associated with the deposited second substrate may weak, or the size of the primary deposit is relatively small. The additional deposition step allows further amplification of the signal associated with the deposit and it may also increase the size of detectable deposits at single target sites. Further, the step also allows modifying the character of the detectable signal, e.g. changing spectral characteristics of the signal, e.g. the initial label detectable as a red signal may be substituted for a label detectable as a green signal by using conjugate molecules comprising said green label for this additional deposition instead of conjugate molecules comprising a red label used for the initial deposition (at step (b) of the method). Such flexibility of the method of the invention, however do not add an extra complexity to reagents used in additional steps of detection, as all embodiments of incubation media of steps (a) and (b) (discussed above) of the method may be successfully used without substantial modifications in these addition steps.

In one embodiment the invention relates to washing media, i.e. media for removing the rests of compounds (of incubation medium) from the sample after the technical effect of the incubation has taken place. The method of the invention may comprise one or more washing steps typically following a step of incubation of the sample in media described above, e.g. between steps (a) and (b), etc. Typically, a washing medium will be the same medium that has been used for incubating of the sample in a step preceding the washing step without the essential compounds of the incubation media, i.e. without binding agent, substrates of the enzyme, etc.

In one embodiment, the invention relates to a media for quenching the endogenous oxidoreductase activity. This type of media may be any media of such kind that is routinely used for the purpose in the art, for example a solution of hydrogen peroxide. This medium may be used before step (a) of the method. It can also be used after step (b) and before additional steps of detection of the deposited second substrate. Application of this medium at this stage of the procedure may used for quenching the residual oxidoreductase activity in the sample.

Discrete Deposits of Second Substrate

It is surprisingly found that using particular conditions of deposition media comprising particular conjugate molecules of the second substrate of enzyme with oxidoreductase activity and relatively low amounts of the first substrate of enzyme with oxidoreductase activity a peroxide compound, such as DAB and hydrogen peroxide, it is possible to form discrete deposits of said conjugate molecules at single target sites of the invention that have distinct physical features, namely round-shaped deposits larger than 0.4 micrometer in diameter, which can be directly observed using a regular microscopic optics or visualized as distinct dots. Using a similar amplification system (that employs the HRP-DAB mediated deposition of detectable conjugate molecules, see for details WO2009036760, WO2010094283 and WO2010094284) it has been possible to improve the traditional HRP-DAB IHC staining in that the homogeneous color pattern of target staining has become more crisp improving thereby the intracellular resolution of cellular structures, e.g. membrane, cytoplasm, and nucleus. The present visualization system provides instead a dotted pattern of target staining, wherein one single dot correspond to one individual target unit, such as one individual target molecule, allowing thereby the intracellular resolution of individual single target units such as single target molecules.

The deposits of detectable conjugate molecules of the invention produced by the method of the invention are three dimensional and have a substantially spherical shape, which in a two dimensional field, e.g. a microscopic field, are observed as distinct substantially rounded dots. Accordingly, the term "rounded dot" (interchangeably used herein with terms "dot" and "distinct dot") designates in the present context a spherical deposit of detectable conjugate molecules of the invention observed in a two-dimensional field as a distinct substantially rounded dot. The term "distinct" in the present context means that a dot of the invention is distinguishable to the eye or mind as discrete The term "substantially rounded" means that a distinct dot of the invention has eccentricity that is around or less than 0.65. A dot according to the invention has a diameter of around or greater than 0.4 microns. The term "around" in the present context means+/−0.05-0.5 micrometer. In comparison, a "dot" of a deposit of the DAB stain by the traditional DAB-HRP method, or a single deposit of the stain at target sites obtained by the methods of WO2009036760, WO2010094283 and WO2010094284, or biotinyl- and fluorescyl-tyramide deposits by the CARD method has a size that is under the resolution limits of the regular microscopic optics (such as 4× or 10× magnification bright field or fluorescent optics), i.g. less than 0.1 microns. Accordingly, it is impossible to directly observe individual single target units visualized by the latter methods in a low magnification microscopic field (such as. 4× or 10×). The method described herein allows detecting and visualizing single deposits of detectable conjugate molecules of the invention at single target sites and thereby observe immobilized single units of targets in samples using low-magnification optics.

The term "one single deposit of the second substrate" (of enzyme with oxidoreductase activity) or "one single deposit of detectable conjugate molecules" (of the invention) relates to a single accumulation of a plurality of conjugate molecules of the second substrate. According to the invention, one distinct deposit of second substrate the invention may comprises from about 1000 and up to 1000000 conjugate molecules or more.

As discussed above, the second substrate deposited at a single target site may comprise visually identifiable molecules, e.g. molecules that comprise a visually detectable label, e.g. a fluorescent label. Accordingly, in one embodiment, a dot of deposit of such second substrate may be detected by a microscopist by using a conventional fluorescence microscope straight after the deposit has been formed. Deposits of reporter molecules that comprise labels that are not directly observable by standard microscopic optics, e.g. a member of a specific binding pair, are to be visualized according to the invention using at least one an additional step detection step, e.g. an additional step (c) described above.

The number of dots, their size and visual appearance can be controlled. For example, in different embodiments dots of a particular size and particular appearance (e.g. particular color) may be produced.

In one embodiment, the size of deposit and the dot size may be varied by using binding agents involved in formation of target sites of the invention comprising different number of enzyme moieties (the terms "enzyme moieties" or "enzyme" is in the present context mean an enzyme with oxidoreductase activity), e.g. the number of HRP per binding agent. In another embodiment the dot size may be controlled by duration the deposition process. In another embodiment, the dot size may be regulated by the content of the deposition media, such as the amount of first and/or second substrates, or a peroxide compound in the deposition media.

Thus, in one embodiment the number of the enzyme units per molecule of binding agent used for formation of a target site may influence the size of a dot. It is found that the dot size may be directly correlated to the number of the enzyme moieties per complex comprising one or more binding agents and one single unit of a target: Larger dots are observed when binding agents used for formations the target sites comprise a larger number of enzyme moieties per molecule (under otherwise the same deposition conditions (i.e. same incubation time, same composition of the deposition media) compared to the dots obtained with use of the same binding agents, but comprising less enzyme moieties per molecule.

To produce a visible dot corresponding to one single deposit under conditions of the invention, it is sufficient that the target site comprises a single, i.e. one enzyme moiety, e.g. a binding agent involved in formation of a target site comprises a single HRP moiety; however, in embodiments when two or more enzyme moieties are present at the same target site, the dot associated with this target site is larger than the dot in the first case. Accordingly, in one embodiment, a binding agent associated with one single target site may comprise one single moiety of HRP, in another embodiment, the binding agent may comprise two or more moieties of HRP, e.g. 2, 3, 4, 5, 6, 7, 8, 9 or 10. In one embodiment, the number of the enzyme moieties per binding agent is at least 2, preferably from 3 to 10, such as from 4 to 8 moieties.

It was surprisingly found that using binding agents that involved in formation of target sites of the invention wherein the number of enzyme moieties is at least 2 per molecule of binding agent, it is possible to produce dots of approximately equal size, under otherwise the same conditions, i.e. same conditions of the visualization procedure. Accordingly, in one embodiment, the invention relates to a method, wherein a sample comprising a immobilized target is incubated to one or more binding agents, wherein at least one of the binding agent comprises at least two enzymes with oxidoreductase activity. Thus, individual units of the target in this embodiment are visualized as individual substantially identical dots, i.e. as dots of the same size. In one embodiment the pool of molecules of a binding agent comprising an enzyme with peroxidase activity may be heterogeneous in that said molecules of comprise different number of the enzyme moieties per molecule, such as e.g. between 2 and 10 molecules, between 11 and 20 molecules, etc. In another embodiment, invention relates to the method, wherein every molecule of the pool of molecules of binding agent comprising an enzyme with peroxidase activity comprises the substantially identical number of the enzyme moieties per molecule of the binding agent, such as 1-3, 2-4-, 3-5, 4-6, 5-7, 6-8, 7-9, 8-10, 9-11, 10-12 etc. enzyme moieties per binding agent molecule.

In another embodiment the size of a dot is regulated by the amount of the first substrate in a deposition media, e.g. by the amount of DAB. Large dots, i.e. the dots which diameter is equal or larger than 0.4 microns, or equal or larger than 1 micron, or equal or larger than 2 or 3 microns, such as 4 or 5 microns, wherein the amount of deposited reporter (per dot) is not less than 1000 molecules, may be formed when the amount of DAB in the deposition media (in otherwise the same conditions of the visualization procedure, i.e. same binding agent, same reporter, same amount of the reporter, same concentration of the peroxide, same incubation time, etc) is in the range from about 0.01 mM about 1 mM, e.g. between 0.05 mM and 0.75 mM, such from around 0.075 mM to around 0.5 mM, such as. around 0.1 mM, e.g. 0.15 mM, or around 0.3 mM, e.g. 0.28 mM, etc. Dots of a smaller size, i.e. less than 0.4 microns, may be observed when both the higher and lower amounts of DAB in deposition media are used.

Composition and structure of the conjugate molecules of the inventions influence the capability of said molecules to be deposited as the second substrate of the invention (discussed above), and therefore they influence size of the deposits and apparent size of a dot. Further, a label of the conjugate may influence the appearance of a dot. For example, in embodiment when the conjugate molecule comprises a fluorescent label, the nature of the fluorofore group of the label will influence the appearance of the dot, e.g. under identical conditions conjugates comprising Lissamine (red fluorofore group) produce more intense dots than similar conjugates comprising Fluorescein (green fluorofore group). Further, higher amounts of the second substrate in the deposition medium, under otherwise the same conditions, may lead to formation of larger deposits.

The size of a dot may also be regulated by the time used for deposition of the second substrate. Longer incubation time in a deposition media allows depositing a larger amount of conjugate molecules at single target sites, increasing thereby the size of a single deposit and sequentially the size of a single dot. Increasing incubation time from 30 seconds to 10 minutes, in otherwise the same conditions, i.e. the same binding agent, same media, etc, may allow to the enzyme producing deposits that can be observed as single dots of a diameter around 5 micrometer. However, a further increase in duration of the incubation does not increase the size of a single deposit. However, longer times of the incubation in the deposition media do not decrease the size of single deposits, and if desirable, longer incubation times, e.g. up to 20 or 30 minutes or longer may be used. Thus, in different embodiments the duration of the deposition step of the method may vary from about 30 seconds to about 20 minutes, e.g. 1, 2, 3, 4, 5, 10, or 15 minutes, e.g. in one embodiment, the incubation time may be about 30 seconds, in another embodiment the time may be about 2 minutes. In one embodiment it is preferred that conjugate molecules are deposited during 5-10 minutes.

The amount of a peroxide compound in the deposition media may also be used as a factor for the regulation of size of the reporter deposit and, accordingly, the dot size. To obtain single dots that are up to 5 micrometers in diameter, the amount of a peroxide compound, such as e.g. hydrogen peroxide, in the deposition media should be less than 2 mM, preferably the amount does not exceed 1.5 mM. Higher amounts of a peroxide compound lead to formation of dots of a smaller size.

All the factors discussed above are termed in the present context "primary factors" as they influence formation of the initial, i.e. primary deposit of the second substrate. As mentioned, such primary deposits may be observed immediately after the deposition has taken place, e.g. in case conjugate molecules of the second substrate comprise a fluorescent label. In other embodiments, the primary deposits are not directly observable, however they may be visualized in one or more detection steps (termed in the present context "secondary visualization procedure") following the deposition step, e.g. in case the conjugates comprise a label that is a member of a specific binding pair, e.g. a hapten. Several factors of the secondary visualization procedure may also influence the visual size and appearance of the deposit as a dot, adding thereby to flexibility of the visualization system of the present invention. These factors are termed "secondary factors" accordingly.

The deposits of reporter molecules comprising a label that is a member of a specific binding pair may be visualized performing following detection steps (c') and (c") which directly or indirectly follows the deposition step:

(c') incubating a sample comprising discrete deposits of second substrate at single target sites with one or more binding agents capable of directly or indirectly binding to a detectable label of the deposited second substrate, wherein at least one of the binding agents comprises one or more detectable labels selected from radioactive, fluorescent or luminescent substances, members of specific binding pairs, or enzymes, thereby forming a complex comprising the deposited reporter and said at least one binding agent, (c") detecting in the sample the binding agent comprising the detectable label, thereby visualizing one or more reporter deposits at one or more individual target sites, and thereby visualizing one or more individual units of the target in the sample.

The term "indirectly" in the present context means that it may be one or more optional steps between the step (b) and (c'), e.g. a washing step.

By using reporter recognizing binding agents that comprise multiple enzyme moieties (as detectable labels) that can utilize chromogenic or fluorescent substrates, e.g. HRP or alkaline phosphotase (AP), it is possible to "stain" the deposits and produce distinct visibly detectable dots. In this case, the original size of a single deposit may be "increased" or "decreased" by producing a distinct visually detectable dot of a certain size. In one embodiment, using a binding agent labeled with HRP or another oxidoreductase enzyme, and optimal conditions of the deposition (discussed above) the step of deposition may be repeated one or more times, thereby increasing the size of a detectable deposit at a single target site after every repetition. In another embodiment, using a binding agent labeled with HRP or another oxidoreductase enzyme, and sub-optimal conditions of the deposition (discussed above), the deposition step may be repeated yielding in deposits of a smaller size and, accordingly, smaller size of H the corresponding detectable dots. In one embodiment, the deposition step may be repeated using conjugate molecules as second substrate which are different from the conjugate molecules used for the primary deposition, e.g. comprising another label, e.g. Lissamin label instead of Fluorescein label. In other embodiment, deposition time or deposition media conditions may be optimized to produce smaller or larger secondary deposits at the primary single target sites.

Thus, the visualization method of the present invention comprises a flexible and powerful amplification system. The double regulation system provide en extra flexibility which may be particular advantageous in some embodiments, e.g. in an embodiment when it is desirable to visualize large primary deposits as dots of smaller size. Dots of a smaller size may allow a more precise target unit positioning in the sample and also may allow detection of a larger dynamic range of target.

The double regulation described above may also be desirable in embodiments when two or more different targets are to be detected, or in embodiments when a target is present in the sample in a broad dynamic concentration range, or in embodiments when the primary deposit provides a weak detectable signal, etc. Visualization and quantification of targets present in a sample in a broad dynamic concentration range, i.e. there is a gradient of target concentration in the sample, may be challenging. At the lowest end of the range the number of the target site related dots may be insufficient to provide statistically valid information about the presence of the target throughout the entire sample, whereas at the highest end of the dynamic range, visualization of single units of the target may be challenged by the presence of a number of overlapping dots that cannot be visually distinguished separately from each other. Use of the primary and/or secondary factors described above to decrease an apparent size of the dots corresponding to large primary deposits may allow overcoming these problems and visualize and quantify targets present in samples in broad dynamic ranges.

Methods of detection of primary deposits of the second substrate may be different depending on type of the sample, features of the deposited molecules, etc. Any suitable method of the art may be used, e.g. in histological samples the deposits may be detected by using any standard IHC staining e.g. HRP-DAB staining, ELISA visualization or immunoblot staining may be used in other embodiments, etc.

Embodiments of Method of Detection of Individual Units of Targets in Samples

The following are non-limited examples of embodiments of the method of the invention.

Method of Detection of Single Target Molecules of a Biological Marker in a Histological Sample In one embodiment the method of the invention may be used for visualization of single target molecules, such as single molecules of a biological marker, in a histological sample, wherein said method comprises the following steps:

a) incubating a sample supposedly comprising one or more single molecules of the biological marker with one or more binding agents, wherein at least one of the binding agents is capable of directly binding to one individual molecule of said biological marker and wherein at least one of the binding agents comprises an enzyme with peroxidase activity, thereby forming one or more target sites, each single target site comprising a complex of one single molecule of the biological marker and one or more binding agents, wherein at least one of the binding agents comprises the enzyme with peroxidase activity;

b) incubating the sample supposedly comprising one or more target sites of (a) in an aqueous solution comprising
 i) 3,3'-diaminobenzidine (DAB)
 (ii) a peroxide compound,
 wherein the amount of DAB is from about 0.1 mM to about 1 mM, and the amount of the peroxide compound is from about 0.5 mM to about 2 mM,
 and
 (iii) one or more populations of conjugate molecules, wherein said conjugate molecules are selected from the group of compounds defined by the formula:

$(Y)n\text{-L-}(Z)m$, wherein
 Y is a substrate of the enzyme with peroxidase activity
 Z is a detectable label;
 L is a linker, and
 n is an integer from 2 to 150, and m is an integer from 1 to 150,
 thereby forming one or more discrete deposits of said reporter molecules at single target sites of (a); and visualizing said single target sites in the sample as distinct single dots, and, optionally, c) visualizing the discrete deposits at single target sites as distinct single dots;
 thereby visualizing one or more single molecules of the biological marker in the sample.

Embodiments of binding agents, conjugate molecules, incubation media (e.g. the aqueous solution of step (b)), visualizing means, etc. are discussed above).

It is understood that instead of HRP another enzyme of the oxidoreductase family discussed above and other compounds than DAB as the first substrate may be used. Further, other compounds that suitable as the second substrate of the invention may be used instead of the compounds of formula (Y)n-L-(Z)m defined above.

In one embodiment the method above may comprise any further steps discussed above. In one embodiment, the method may comprise one or more steps following any of the steps a, b or c. In another embodiment, the method may comprise one or more steps preceding any of the steps a, b or c. The method may comprise at least one of automated step, or further comprise at least one automated step.

In some embodiments, e.g. when the biological marker is abundantly expressed in the sample or expressed in a broad dynamic concentration range, it may be preferred that the sample is incubated with one or more binding agents involved in formation single target sites under conditions when the binding agents are capable of forming the target sites with a fractional subpopulation of single target molecules. Embodiments of such conditions are discussed above, In other embodiment, e.g. when the biological marker is a low expression target, it may be preferred that substantially all single molecules of the biological marker are involved in formation of the target sites. In these embodiments it is preferred to incubate the sample with one or more binding agents under optimal conditions, i.e. under conditions when binding agents are capable of forming the target sites with all available target units.

In one embodiment the target an epidermal growth factor receptor (EGFR) or the corresponding nucleic acids, in particular Her2 receptor or nucleic acids encoding thereof.

Any protein or another biological molecule, structure or molecular complex that is known in the art as a biological marker of a disease is included in the scope of the invention. In particular, the invention relates to biological markers of cancer.

Method of Detection of Single Units of at Least Two Different Immobilized Targets in One Sample In another embodiment the method of the invention may be used for the detection and visualization of single units of two or more different targets, e.g. single molecules of two or more different biological markers, in one and the same sample.

A method for visualization and detection of single units of at least two different immobilized targets in a sample, e.g. a histological sample, according to the invention comprises
 incubating the sample with one or more binding agents capable of binding a first target, wherein
  (1) at least one of the binding agents comprises an enzyme;
  (2) at least one of the binding agents is capable of directly binding to an individual single unit of first target,
 thereby forming one or more discrete first single target sites with individual single units of the first target, wherein each single discrete first target site comprises a complex of one individual single unit of the first target and one or more binding agents, at least one of the binding agents comprising the enzyme;

b) incubating the sample of (a) with a first substrate of the enzyme associated with the first single target sites, a first population of molecules of second substrate of said enzyme and a peroxide compound according to step (b) of method (1) above (i.e. step (b) of claim 1), thereby forming discrete deposits of molecules of second substrate of the first population at the first single target sites of (a);

c) incubating the sample of (b) with a solution of hydrogen peroxide in an amount sufficient to quench the residual activity of the enzyme associated with the first single binding sites of (a);

d) incubating the sample (c) with one or more binding agents capable of binding to a second target, wherein
   (1) at least one of the binding agents comprises an enzyme;
   (2) at least one of the binding agents is capable of directly binding to an individual unit of second target,
   thereby forming one or more discrete second single target sites with individual single units of the second target, wherein each single discrete second target site comprises a complex of one individual unit of the second target and one or more binding agents, at least one of the binding agents comprising the enzyme;
e) incubating the sample of (d) with a first substrate of the associated with the second single binding sites, a second population of a molecules of second substrate of the enzyme with oxidoreductase activity and a peroxide compound according to step (b) of methods (1) above (i.e. step (b) of claim 1), thereby forming discrete deposits of molecules of second substrate of the second population at the second target sites of (d);
f) detecting in the sample the discrete deposits of molecules of second substrate of the first population at the first target sites as first visually distinct dots, thereby detecting one or more individual single units of the first target;
g) detecting in the sample the discrete deposits of molecules of second substrate of the second population at the second target sites as second visually distinct dots, thereby detecting one or more individual single units of the second target.

The targets of the method above are in one embodiment different biological markers, e.g. different biological molecules. In one embodiment, the targets are different nucleic acid sequences or different protein molecules. In one embodiment a first target may be a nucleic sequence and a second target may be a protein molecule, e.g. Her2 receptor and a Her2 related nucleic sequence.

In one embodiment at least one of the targets may be a biological marker and at least one another may be a reference marker, e.g. one target is Her2 receptor (biological marker) and another target is cytokeratin (reference marker). Selection of a biological marker and reference marker is depend on the sample and can be done according to the knowledge of accumulated in the relevant prior art, in particular in embodiments when biological and reference markers of a disease or another physiological condition are concerned.

The method above may comprise any further steps discussed above. In one embodiment, the method may comprise one or more steps following any of the steps a, b or c. In another embodiment, the method may comprise one or more steps preceding any of the steps a, b or c. The method may comprise at least one automated step, or further comprise at least one automated step In one embodiment the sample is a histological sample.

In one embodiment the enzyme with oxidoreductase activity is HRP. In one embodiment the first substrate of enzyme with oxidoreductase activity is DAB. Embodiments relating to HRP and DAB may be any of the discussed above. In other embodiments the enzyme may be preferred from any other oxidoreductase enzymes, e.g. selected from the discussed above. In other embodiments the first substrate may be preferred from any other compounds suitable as the first substrate, e.g. selected from the discussed above Molecules of the second substrate of any of the populations used for the detection of single units of different targets may be e.g. conjugate compounds described above. Some exemplary compounds are also described in the EXAMPLES section. Conjugate molecules of the first population and conjugate molecules of the second population differ by different detectable labels they comprise. In another embodiment molecules of the first population and reporter molecules of the second population may further differ by the composition of compounds that are capable of serving as substrates for the enzyme with oxidoreductase activity. In other embodiments the molecules may further differ by other features, e.g. structure of a conjugate molecule, length of the linker between the substrate of the enzyme with oxidoreductase activity and the label, number of detectable labels, etc.

The step of deposition of molecules of the second substrate, i.e. step (b) and/or (e), may be performed according to any embodiment described above, e.g. the sample may be first pre-incubated in a solution with a first substrate of the enzyme with oxidoreductase activity and a peroxide compound, and, then, incubated in a solution comprising a combination of a first substrate, a second substrate and a peroxide compound.

In one embodiment at least one of the at least two targets present in the sample in a broad dynamic concentration range.

Non-limiting examples of visualization of at least two targets in one sample may be visualization of a biological marker and a reference marker Method of Detection of Single Units of an Immobilized Target Present in a Sample in a Broad Dynamic Concentration Range Detection and visualization of single units of a target present in the sample in a broad concentration range may be challenged at the lowest end of the range by formation a very few actual reporter deposits compared to the level of noise and false deposits through entire sample to provide statistically valid information, whereas at the highest end of range, visualization of the single units may be limited by the presence of overlapping dots that cannot be visually separated. Accordingly, it may be advantageous to utilize at least two separate steps of deposition of two different reporters wherein molecules of the first reporter are deposited at the first target sites that are located in the area of sample having abandon presence of units of the target, and molecules of the second reporter are deposited at second target sites that are located in the areas of low presence of the target.

Thus, a method for detection and visualization of single units of a target in a sample, wherein the target is present in a broad concentration range, according to the invention comprises:
a) incubating the sample with one or more binding agents, wherein
   (1) at least one of the binding agents comprises an enzyme;
   (2) at least one of the binding agents is capable of directly binding to an individual single unit of said target,
   and forming one or more discrete first target sites with a first fractional sub-population of individual single units of the target, wherein each single discrete first target site comprises a complex of one individual single unit of said first fractional sub-population of individual single units and one or more binding agents, at least one thereof comprising the enzyme with oxidoreductase activity;
b) incubating the sample of (a) with a first substrate of the enzyme associated with the first target sites of (a), a first population of molecules of second substrate said enzyme and a peroxide compound according to step (b) of claim 1, thereby forming discrete deposits of molecules of second substrate of the first population at the first target sites of (a);

c) incubating the sample of (b) with a solution hydrogen peroxide in an amount sufficient to quench the residual activity of the associated with the first single target sites of (a);
d) incubating the sample (c) with one or more binding agents, wherein
   (1) at least one of the binding agents comprises an enzyme;
   (2) at least one of the binding agents is capable of directly binding to an individual unit of said target,
thereby forming one or more discrete second target sites with a second fractional sub-population of individual single units of the target, wherein each single discrete second target site comprises a complex of one individual unit of said second fractional sub-population of individual single units and one or more binding agents, at least one thereof comprising the enzyme;
e) incubating the sample of (d) with a first substrate of the enzyme associated with the second single target sites, a second population of a molecules of second substrate of said enzyme and a peroxide compound according to step (b) of method (1) above (i.e. step (b) of claim 1), thereby forming discrete deposits of molecules of second substrate of the second population at the second target sites of (d);
f) detecting in the sample the discrete deposits of molecules of second substrate of the first population at the first target sites as first visually distinct dot, thereby detecting one or more individual single units of the first population of the target;
g) detecting in the sample the discrete deposits of molecules of second substrate of the second population at the second target sites as second visually distinct dots, thereby detecting one or more individual single units of the second population of the target.

In one embodiment the binding agents of (a) and (d) may be same binding agents. In one embodiment it may be preferred that the quantity of the binding agent used on step (a) to form single target sites with the first fractional subpopulation of the target is lesser than the quantity of binding agent used to form single target sites with the second fractional subpopulation of the target on step (d).

In another embodiment, the binding agents of (a) and (d) may be different binding agents, e.g. two different antibody binding agents, two different nucleic acid binding agents, an antibody as binding agent (a) and nucleic acid as binding agent (b), two the target specific antibody that have different affinity to the target, etc.

In one embodiment reporter molecules of the first population and reporter molecules of the second population differ by different detectable labels they comprise. In another embodiment molecules of the first population and reporter molecules of the second population differ by the composition of compounds that are capable of serving as substrates for the enzyme with oxidoreductase activity. In other embodiments the molecules may differ by other features, e.g. structure of a conjugate molecule, length of the linker between the substrate of the enzyme with oxidoreductase activity and the label, number of detectable labels, etc.

Quantification of an Immobilized Target in a Sample

In one aspect the invention relates to a method of quantification of an immobilized target in a sample. The methods of visualization and detection of single units of targets of the invention (described above) may be used for quantitative evaluation of relative amounts of such targets in samples, in particular in histological samples.

A method for quantitative evaluation of an immobilized target in a sample, e.g. quantitative evaluation of expression of a biological marker in a sample, in one embodiment may comprise:
a) processing the sample according to one of the methods of the invention, such as
   (i) of claim 1 (as discussed in the above section Method of visualization of individual units of an immobilized target in samples or section Method of detection of single target molecules of a biological marker in a histological sample;
   (ii) of claim 36 (as discussed in the above section Method of detection of single units of an immobilized target present in a sample in a broad dynamic concentration range); or
   (iii) of claim 40 (as discussed in the above section Method of detection of single units of at least two different immobilized targets in one sample);
b) quantifying distinct dots in the sample; and
c) evaluating quantity of the target in the sample.

Quantification of distinct dots of the invention in the processed sample may be done manually or automatically considering different features of the dots, e.g. because of the dots are distinguishable to the eye or mind as discrete they may be counted wherein the number of counted dots will indicated levels of expression of a marker in the sample, the color characteristics of dots may be used to distinguish and count the dots associated with two different targets in one sample, etc. Using software for processing images of samples comprising single target units visualized by the methods of the invention, it is possible to make evaluation of target expression based on different features, e.g. dot color characteristics, intensity of the signal associated with single dots or with the entire sample, relative distribution of dots within the sample, etc.

In one embodiment, the counting may be performed manually, i.e. by a microscopist observing a microscopic field of the sample, or an observer that analyze a digital image of the sample. Counting can also be done automatically using any available software developed in the art for cell image processing, e.g. CellProfiler software. An exemplary quantification of Her2 in a sample is described in EXAMPLES.

In one embodiment the amount of a target in a sample may be evaluated without any reference, e.g. as a relative amount of the target or relative amount single units of a target in the sample. In another embodiment, the amount of a target may evaluated considering a reference marker, e.g. relatively per a particular biological molecule or a cellular structure of the sample, relatively per sample volume, relatively per sample area, etc.

The methods as described above are of particular advantage for the quantitative evaluation of targets in complex histological samples. Accordingly, in one preferred embodiment the invention relates to a quantitative evaluation of a target in histochemical sample.

Using the method of the present invention a target in a histological sample may be quantified without use of any reference marker, e.g. a sample of a particular body tissue may be characterized by using such reference as the number of dots corresponding to a target, presumed that samples of that particular tissue are being processed by using the same visualization procedure according to the invention. In one embodiments, a target may be quantified relative to a sample volume, sample area (i.e. an area of a microscopic field or an area of a digital image of the sample) every time per staining of biological targets and quantification of the staining results.

Diagnostic Applications

Estimation of expression of biological markers, i.e. markers which expression has a diagnostic, prognostic or therapeutic value, is routinely used for making or confirming medical diagnoses or for predicting outcomes of therapeutic treatments, or for monitoring development of diseases. When such evaluation is based on analysis such complex samples as histological samples, it has relative value because the results of analysis are strongly depends on the quality of a sample, sensitivity of the detection method, variations in the expression levels, etc, and therefore evaluation of expression a biological marker in a series of histological samples of same tissue of same patient may give very different results, and lead to an erroneous assumption and diagnosis, and, as a consequence, to non-effective therapy. Evaluation of expression of diagnostic and therapeutic markers based on estimation of the content of single molecules of said markers in a patient sample according to the described herein method can provide more reliable evaluation and errorless medical diagnostics and furthermore a personalized target directed therapy.

Accordingly, in one embodiment, methods of the invention may be used in for diagnosing a disease in a patient, wherein said diagnosing comprising a step of processing a biological sample obtained from the patient according to any of the methods of the invention.

In another embodiment, methods of the invention may be used in for estimating efficacy of a therapeutic treatment in a patient, wherein said estimating comprises analysis of a patient sample which has been processed according to any of the methods of the invention.

In another embodiment, methods of the invention may be used for providing a medical prognosis, e.g. a prognosis of the risk of development of a disease in a patient, or prognosis of the likelihood of recovery or failure form a disease, wherein a method of said prognosis comprises a step of processing and analysis of a biological sample obtained from a patient according to any of the methods of the invention.

In another embodiment, methods of the invention may be used for stratification of patients for a therapeutic regime, wherein said stratification comprising analysis of samples of patients which have been processed according to any of the method of the invention.

The method may also be used for monitoring a disease, e.g. disease progression or amelioration, or can also be used in the process of new drug screening, e.g. for estimating a therapeutic potential of a new drug in an in vitro assay, etc.

Visualization methods of the invention may be employed in a variety assay formats that typically used for latter applications, e.g flow cytometry (FC), ELISA, histochemistry (both IHC and ISH), blotting, etc. For example, in one embodiment the biological sample may be a suspension of cells. Target biological molecules or target structures of cells in suspension may be detected using FC, ELISA, IHC or ISH. When ELISA, IHC or ISH are used for the detection, cells of a suspension are to be attached to a solid support, e.g. a plate (ELISA) or a slide (IHC). In another embodiment the biological sample may be a sample of a body tissue, e.g. a section of a fixed and paraffin embed tumor sample. Target molecules or structures of cells of such samples will be typically detected using IHC or ISH.

IHC and ISH assay formats usually require a series of treatment steps preceding visualization of target molecules which may be conducted on a tissue section mounted on a suitable solid support for microscopic inspection, or the production of photomicrographs, e.g., a glass slide or other planar support, to highlight by selective staining certain morphological indicators of disease states or detection of biological markers. Thus, for example in IHC, a sample is first taken from an individual, then fixed and only then it exposed to antibodies which specifically bind to the biological marker of interest. The sample processing steps may also include other steps preceding a visualization procedure according to the invention, for example, It may involve the steps of: cutting and trimming tissue, fixation, dehydration, paraffin infiltration, cutting in thin sections, mounting onto glass slides, baking, deparaffination, rehydration, antigen retrieval, blocking steps, etc., Washing steps may be performed with appropriate buffers or solvents, e.g., phosphate-buffered saline (PBS), tris buffered saline (TBS), distilled water. The wash buffers may optionally contain a detergent, e.g., Tween 20. All these procedures are well-known routine procedures in laboratories.

Both of two categories of histological samples: (1) preparations comprising fresh tissues and/or cells, which generally are not fixed with aldehyde-based fixatives, and (2) preparations of fixed and embedded tissue specimens, often archived material, may be processed using methods of the invention.

Many methods of fixing and embedding tissue specimens are known, for example, alcohol fixation and formalin-fixation and subsequent paraffin embedding (FFPE).

Fixatives are needed to preserve cells and tissues in a reproducible and life-like manner. To achieve this, tissue blocks, sections, or smears are immersed in a fixative fluid, or in the case of smears, are dried. Fixatives stabilize cells and tissues thereby protecting them from the rigors of processing and staining techniques.

Any suitable fixing agent may be used, for example, ethanol, acetic acid, picric acid, 2-propanol, tetrahydrochloride dihydrate, acetoin (mixture of monomer and dimer), acrolein, crotonaldehyde (cis+trans), formaldehyde, glutaraldehyde, glyoxal, potassium dichromate, potassium permanganate, osmium tetroxide, paraformaldehyde, mercuric chloride, tolylene-2,4-diisocyanate, trichloroacetic acid, tungstic acid. Other examples include formalin (aqueous formaldehyde) and neutral buffered formalin (NBF), glutaraldehyde, acrolein, carbodiimide, imidates, benzoequinone, osmic acid and osmium tetraoxide.

Fresh biopsy specimens, cytological preparations (including touch preparations and blood smears), frozen sections and tissues for immunohistochemical analysis are commonly fixed in organic solvents, including ethanol, acetic acid, methanol and/or acetone.

To facilitate the specific recognition in fixed tissue, it is often necessary to retrieve or unmask the targets, i.e., the biological markers of interest, through pre-treatment of the specimens to increase reactivity of the majority of targets. This procedure is referred to as "antigen retrieval", "target retrieval" or "epitope retrieval", "target unmasking" or "antigen unmasking." An extensive review of antigen retrieval (antigen unmasking) may be found in Shi et al. 1997, *J Histochem Cytochem*, 45(3):327.

Antigen retrieval includes a variety of methods by which the availability of the target for interaction with a specific detection reagent is maximized. The most common techniques are enzymatic digestion with a proteolytic enzyme (for example proteinase, pronase, pepsin, papain, trypsin or neuraminidase) in an appropriate buffer or heat induced epitope retrieval (HIER) using microwave irradiation, heating in a water bath, a steamer, a regular oven, an autoclave or a pressure cooker in an appropriately pH stabilized buffer, usually containing EDTA, EGTA, Tris-HCl, citrate, urea, glycin-HCl or boric acid. Detergents may be added to the HIER buffer to increase the epitope retrieval or added to the dilution media and/or rinsing buffers to lower non-specific binding.

The antigen retrieval buffer is most often aqueous, but may also contain other solvents, including solvents with a boiling point above that of water. This allows for treatment of the tissue at more than 100° C. at normal pressure.

Additionally, the signal-to-noise ratio may be increased, if desired, by different physical methods, including application of vacuum and ultrasound, or freezing and thawing of the sections before or during incubation of the reagents.

Endogenous biotin binding sites or endogenous enzyme activity (for example phosphatase, catalase or peroxidase) may be removed as a pre-detecting step in the detection procedure, e.g., endogenous biotin and peroxidase activity may be removed by treatment with peroxides. Endogenous phosphatase activity may be removed by treatment with levamisole. Endogenous phosphatases and esterases may be destroyed by heating. Other methods of such pretreatment known in the art may also be used.

Blocking of non-specific binding sites is not necessary when the methods of the present invent are used, however, if desired, blocking may be performed using standard approached of the art, e.g. with inert proteins like, horse serum albumin (HSA), casein, bovine serum albumin (BSA), and ovalbumin, fetal calf serum or other sera, or detergents like Tween20, Triton X-100, Saponin, Brij or Pluronics may be used. Blocking non-specific binding sites in the tissue or cells with unlabeled and target non-specific versions of the specific reagents may also be used.

Samples may also be prepared and target molecules detected using the free floating technique. In this method a tissue section is brought into contact with different reagents and wash buffers in suspension or freely floating in appropriate containers, for example micro centrifuge tubes.

The tissue sections may be transferred from tube to tube with different reagents and buffers during the staining procedure using for example a "fishing hook like" device, a spatula or a glass ring. The different reagents and buffer can also be changed by gentle decantation or vacuum suction. Alternatively, containers with the tissue sections can be emptied into a special staining net, like the Corning "Netwells" (Corning,) and the tissue section washed before being transferred back into the tube for the next staining step.

All the steps, including for example fixation, antigen retrieval, washing, incubation with blocking reagents, immuno-specific reagents and the oxidoreductase-mediated deposition, are done while the tissue section is floating freely or withheld on nets. After deposition of the reporter, the tissue section is mounted on slides, the reporter is detected and slide covered with a cover slip before being analyzed, e.g., by light or fluorescent microscopy.

In some embodiments, the tissue section may be mounted on slides following the critical incubation with the immuno-specific reagents following the procedure (a) of the method. The rest of the process of detection is then conducted on the slide mounted tissue sections.

Any of the assays employing the methods of the invention may comprise one or more automated steps. In one embodiment the assays may comprise a manual detection, in another embodiment the assays may be fully automated, in another embodiment the assays may be adjusted for a semi-automated detection.

EXAMPLES

The following are non-limiting working example of the disclosed invention.

Abbreviations
MBHA 4-Methylbenzhydrylamine
NMP N-Methyl Pyrolidon
HATU 2-(1h-7-azabenzotriazole-1-yl)-1,1,3,3 tetramethyl uronium hexafluorophosphate; methenamminium
DIPEA DiIsopropyl EthylAmine
DCM Dichloro Methane
TFA TriFluoroacetic Acid
TFMSA TriFluor Methyl Sulphonic Acid
Flu Fluorescein
Dex Dextran
HPLC High Performance Liquid Chromatography
equi. Equivalent
L30 1,10,16,25-tetraaza-4,7,13,19,22,28-hexaoxa-11,15,26,30-tetraoxo-triacontane
L60, L90, L120, L150 different polymers of L30, comprising 2, 3, 4 or 5 L30 reapeats
ClZ 2-chloroZ=2-chloro Benzyloxycarbonyl
FITC FlouresceinIsoThioCyanate
HRP Horse Radish Peroxidase
GaM Goat anti-Mouse antibody
DNP 2,4 dinitro-fluorbenzene (DiNitroPhenyl)
ACim 4-amino-Cinnamic acid
LPR Liquid Permanent Red (Dako K0540)
Sin sinnapinic acid (4-hydroxy-3,5-dimethoxy cinnamic acid)
Caf caffeic acid (3,4-dihydroxy cinnamic acid)
PNA-X peptide nucleic acid oligomer (N-(2-aminoethyl)-glycine) comprising different substituents coupled to the central nitrogen
A adenine-9-acetic acid,
C cytosine-1-acetic acid,
D 2,6-diaminopurine-9-acetic acid,
G guanuine-9-acetic acid,
Gs 6-thuioguanine-9-acetic acid,
P 2-pyrimidinone-1 acetic acid,
T thymine-1-acetic acid,
Us 2-thiouracil-1-acetic acid.
Dpr 2,3 diamino-propioninc acid,
Phe phenylalanine,
Tyr tyrosine,
Trp tryptophane,
Lys lysine,
Cys cysteine,
betaala betaalanine, N,N diacetic acid
FFPE formaldehyde fixed paraffin embedded
SMD single molecule detection
Cross-linker a first substrate of an enzyme with oxidoreductase activity
Reporter a second substrate with an enzyme with peorxidase activity
Second Substrate Molecules

TABLE 1

Conjugate molecules, intermediate products of their synthesis and control constructs

| | Conjugate ID | Structure | Synthesis protocol No. |
|---|---|---|---|
| 1 | D19112/D19057 | Fer-Lys(Fer)-Lys(Fer)-L150-Lys(Flu) | 2 |
| 2 | D19185/D20068/ D20171/D20166/ D21025/ | Fer-Lys(Fer)-Lys(Fer)-Lys(Fer)-L150-Lys(Flu) | 2 |

TABLE 1-continued

Conjugate molecules, intermediate products of their synthesis and control constructs

| | Conjugate ID | Structure | Synthesis protocol No. |
|---|---|---|---|
| | D21030/D21032/ D21045 | | |
| 3 | D20086 | Fer-Lys(Fer)-Lys(Fer)-L30-Lys(Flu) | 2 |
| 4 | D20118 | Fer-Lys(Fer)-Lys(Fer)-L60-Lys(Flu) | 2 |
| 5 | D20120 | Fer-Lys(Fer)-Lys(Fer)-Glu-L30-Lys(Flu) | 2 |
| 6 | D19048/D21053 | Fer-Lys(Fer)L150-Lys(Lissamine) | 2 |
| 7 | D19059 | Fer-Lys(Fer)-Lys(Fer)-L150-Lys(DNP) | 2 |
| 8 | D18146 | ACin-(Lys(ACin)L30)$_5$-(L90-Lys(Flu))$_3$ | 2 |
| 9 | D18044 | Ac-(Tyr-L30)$_5$-(L90-Lys(Flu))$_3$ | 1 |
| 10 | D21008 | (D18074)$_{18.5}$-Dex70-(D18118)$_{27.7}$ | 8 |
| 11 | D18074/D17120/ D17137/D18114 (intermediate) | Fer(Lys(Fer)-L30)$_5$-Lys(NH$_2$) | 3 |
| 12 | D21020 | Caf-Lys(Caf)-Lys(Caf)-L150-Lys(Flu) | 2 |
| 13 | 0328-018/ D21047/D21067 | Sin-Lys(Sin)-Lys(Sin)-L150-Lys(Flu) | 2 |
| 14 | D17093 intermediate | Fer(PNA-Fer)5L30-Lys(NH2) | 3 |
| 15 | D17127/D18118 intermediate | NH2-Cys(SH)-L90Lys(Flu)-L90-Lys(Flu)-L90-Lys(Flu) | 1 |
| 16 | D17128 | (D17093)$_{18.6}$-Dex70-(D17127)$_{26.2}$ | 8 |
| 17 | D17130 | (D17120)$_{18.8}$-Dex70-(D17127)$_{18.6}$ | 8 |
| 18 | D17132 control (no enzyme substrate) | Dex70-(D17127)$_{23}$ | 7 |
| 19 | D17126/D17165 intermediate | Betaala-L90-Lys(Flu)-L90-Lys(Flu)-L90-Lys(Flu) | 1 |
| 20 | D17134/D17135/ D17136 | Fer(Lys(Fer)-L30)5-Lys-(betaala)-(L90-Lys(Flu))3 | 6 |
| 21 | D17138 | Fer(Lys(Fer)-L90)$_5$-Lys(NH$_2$) | 3 |
| 22 | D17139 | Fer-Lys(Fer)L30-(Lys(Fer))2-L30(Lys(Fer))2L30-Lys(NH2) | 3 |
| 23 | D17140 | Fer-Lys(Fer)L60-(Lys(Fer))2-L60(Lys(Fer))2L30-Lys(NH2) | 3 |
| 25 | D17148/D17150/ D17151 | Fer-Lys(Fer)-(L30-Lys(Fer)-Lys(Fer))2-L30-Lys-(betaala)-(L90-Lys(Flu))3 | 6 |
| 24 | D17152 | Fer-L30-Lys(L30Fer)-(L30Lys(L30Fer))4-L30-Lys(NH2) | 5 |
| 26 | D17156 | Fer-L30-Lys(L30Fer)-(L30Lys(L30Fer))4-L30-Lys(betaala)-(L90-Lys(Flu))3 | 6 |
| 27 | D17157 | Fer-L150-Lys(Flu) | 2 |
| 28 | D17158 | Fer-L30-Lys(Flu) | 2 |
| 29 | D17161 control (no enzyme substrate) | Flu-L150-Lys(Flu) | 1 |
| 30 | D17162 control (no enzyme substrate) | Dex270-(D17127)$_{62.9}$ | 7 |
| 31 | D17104 intermediate | Fer-(Lys(Fer)-Gly)4-Lys(Fer)-L30-Lys(NH2) | 3 |
| 32 | D17188 | Fer-(Lys(Fer)-Gly)4-Lys(Fer)-L30-Lys(betaala)-(L90-Lys(Flu))3 | 6 |
| 33 | D17192 intermediate | 7-OH-Cou-(Lys(7-OH-Cou)-L30)5-Lys(NH2) | 3 |
| 34 | D18003 | 7-OH-Cou-(Lys(7-OH-Cou)-L30)5-Lys(betaala)-(L90-Lys(Flu))3 | 6 |
| 35 | D18007 control (no enzyme substrate) | Ac-(PNA-D)5-L120-Lys(Flu)-L90-Lys(Flu)-L90-Lys(Flu) | 1 |
| 36 | D18008 control (no enzyme substrate) | Ac-(PNA-G)5-L120-Lys(Flu)-L90-Lys(Flu)-L90-Lys(Flu) | 1 |
| 37 | D18009 control (no enzyme substrate) | Ac-(PNA-Gs)5-L120-Lys(Flu)-L90-Lys(Flu)-L90-Lys(Flu) | 1 |
| 38 | D18010 control (no enzyme substrate) | Ac-(PNA-P)5-L120-Lys(Flu)-L90-Lys(Flu)-L90-Lys(Flu) | 1 |
| 39 | D18011 control (no enzyme substrate) | Ac-(PNA-A)5-L120-Lys(Flu)-L90-Lys(Flu)-L90-Lys(Flu) | 1 |
| 40 | D18012 control (no enzyme substrate) | Ac-(PNA-C)5-L120-Lys(Flu)-L90-Lys(Flu)-L90-Lys(Flu) | 1 |

TABLE 1-continued

Conjugate molecules, intermediate products of their synthesis and control constructs

| | Conjugate ID | Structure | Synthesis protocol No. |
|---|---|---|---|
| 41 | D18013 control | Ac-(PNA-T)5-L120-Lys(Flu)-L90-Lys(Flu)-L90-Lys(Flu) | 1 |
| 42 | D18014 control (no enzyme substrate) | Ac-(PNA-Us)5-L120-Lys(Flu)-L90-Lys(Flu)-L90-Lys(Flu) | 1 |
| 43 | D18015/D18126/D19130 | Fer-(Lys(Fer)-L30)5-(L90-Lys(Flu))3 | 2 |
| 44 | D18019/D18029 intermediate | Fer-(Lys(Fer)-L30)5-L270-Lys(NH2) | 3 |
| 45 | D18031 | (D18019)$_6$-Dex70-(D17127)$_{22.3}$ | 8 |
| 46 | D18049 | Ac-(Tyr)6-L30-(L90Lys(Flu))3 | 1 |
| 47 | D18077 similar to D17130 | (D18074)$_{17.8}$-Dex70-(D17127)$_{22.2}$ | 8 |
| 48 | D18079 similar to D17130 | (D18074)$_{16.8}$-Dex70-(D17127)$_{23}$ | 8 |
| 49 | D18080/19028 intermediate | Fer-(Lys(Fer)-L30)5-(L90-Lys(NH2))3 | 3 |
| 50 | D18081 | Fer-(Lys(Fer)-L30)5-(L90-Lys(Texas-Red-X))3 | 4 |
| 51 | D18084 | NH2-Dpr(NH2)-(L30-Tyr)7 | 1 |
| 52 | D18085 | NH2-Dpr(NH2)-(L90-Lys(Flu))3 | 1 |
| 53 | D18086 control (no enzyme substrate) | Dex70(D18085)$_{2.6}$ | 7 |
| 54 | D18088 control (no enzyme sunstrate) | Dex70-(D17127)$_{8.6}$ | 7 |
| 55 | D18090 similar to D17130 | (D18074)$_{16.8}$-Dex70-(D17127)$_{23.9}$ | 8 |
| 56 | D18096 | Fer-(Lys(Fer)-L30)5-(L90-Lys(7-OH-Cou))3 | 4 |
| 57 | D18122 | (D18114)$_{17.6}$-Dex70-(D18118)$_{32.9}$ | 8 |
| 58 | D18128 | NH2-Cys(SH)-(L30-Tyr)5-(L90Lys(Flu))3 | 1 |
| 59 | D18130 | Dex70-(D18128)$_{12.4}$ | 7 |
| 60 | D18132 | NH2-Cys(SH)-(Tyr)5-(L90Lys(Flu))3 | 1 |
| 61 | D18133 | Dex70-(D18132)$_{21.8}$ | 7 |
| 62 | D18137 | Ac-(Tyr)5-(L90Lys(Flu))3 | 1 |
| 63 | D18138 | Ac-(Tyr)5-(L90Lys(DNP))3 | 1 |
| 64 | D18141/D18155/D19032 | Fer-(Lys(Fer)-L30)5-(L90-Lys(DNP))3 | 2 |
| 65 | D18157 | Fer-(L30-Lys(Fer))5-(L90-Lys(Flu))3 | 2 |
| 66 | D19037 | Fer-Lys(Fer)-L150-Lys(Flu) | 2 |
| 67 | D19040/D19046 | Fer-Lys(Fer)-L150-Lys(DNP) | 2 |
| 68 | D21028 | Sin-Lys(Sin)-Lys(Sin)-Lys(Sin)-L150-Lys(Flu) | 2 |
| 69 | D21048 | Sin-Lys(Sin)-Lys(Sin)-L150-Lys(DNP) | 2 |
| 70 | D21150 | Sin-Lys(Sin)-Lys(Tyr)-L150-Lys (Flu) | 2 |

Different conjugates and their intermediate compounds are classified in column 3 of the table according to methods of their synthesis, roughly in increasing order of complexity:

1. Solid phase chemistry only.
2. Solid phase, then one solution phase step.
3. Solid phase, then two solution phase steps.
4. Solid phase, then two solution phase steps
5. Solid phase, then four solution phase steps.
6. Solution phase coupling between amino and betaalaanhydride intermediates.
7. Dextran conjugates with one substituent.
8. Dextran conjugates with two substituents.
1. This group includes the 8 conjugates prepared from Tri-Fluorescein labeled PNA-pentamers of the 4 natural and further 4 unnatural bases. (D18007-D18014). There are 4 tyrosin conjugates with 5-6 tyrosines and 3 fluoresceins, D18044, D18049, D18137 and D18138 with three DNPs in place of fluorescein labels. D18128 and D18132 have 5 tyrosines and 3 fluoresceins each, and as such they are potential conjugates, though they also include an N-terminal cystine residue for further dextran coupling, bringing them into the group of "intermediates". Intermediates further include the important Cysteine (D17127) and betaalnine (D17126) tri-fluorescein linkers, as well as the Diamino-propionic-acid linker with 7 tyrosines (D18084) or three fluoresceines (D18085). Finally the small di-fluorescein linker (D17161) used as control was also prepared by solid phase synthesis alone. The synthetic strategy behind all these compound is simple: Boc-protected monomers are commercially available or have prepared in house, and the conjugates and intermediates are prepared by linear solid phase syntheses, followed by cleavage from resin by a cocktail of 6:2:1:1 TFMSA:TFA:m-cresol:thioanisol. For the best results consequent double coupling of all monomers is used. Fluoresceins are introduced on lysine side chains (and the N-terminal, D17161) following Fmoc-deprotection on solid phase. HATU activated Carboxy-fluorescein (mixed isomers) was used for fluorescein labeling (0.2 M in NMP for 3×20 min). DNP labeling was achieved with 2,4-dinitro-fluor-benzene (0.5 M in NMP with DIPEA for 2×10 min).
2. This group includes a large number of conjugates labeled with cinnamic acid derivatives in solution phase following solid phase synthesis of intermediates carrying free N-terminal amino groups and free lysine side chains amino groups. Alpha-N-Boc-(epsilon-N-2-Cl-Z)-lysine was used to introduce lysine residues giving free epsilon-N-amino groups following cleavage from resin. The solution phase labeling is basically an extension of solid phase techniques, utilizing that the relative high molecular weight intermediates can be almost quantitatively precipitated with diethyl ether from TFA or NMP solution.

3. From a synthetic point of view, this group of intermediates represents a yet higher degree of complexity. Solid phase synthesis and solution phase labeling as in 1 and 2, then followed by an additional step of solution phase Fmoc-deprotection. By combining Boc-L30 linkers with Boc-2ClZ and Boc-Fmoc-lysine, intermediates with a combination of protected (Fmoc) lysine side chains and free N-terminal and other lysine side chain free amino groups (from N-terminal Boc and 2-ClZ lysine residues during resin cleavage). These intermediate can be labeled with ferulic acid in solution as in 2. However, prior to the scrubbing step with ethylenediamine, an extra 5 min step with 5% ethanolamine is used. This extra scrubbing step deactivates amino reactive species prior to Fmoc de-protection by ethylenediamine. Without this extra step, ethylenediamine de-protects Fmoc-groups faster than it deactivates HATU activated ferulic acid, and Fmoc "protected" amino groups become labeled with ferulic acid. This group with free amino groups comprises D17120 (six ferulic acids) D17093 (five ferulic acids attached to PNA backbone), D17138 (L90-linkers between ferulic acids) D17139 (six ferulic acids in three close pairs), D17104 (glycine spacers between ferulic acids) D17192 (with six 7-hydroxy coumarins instead of ferulic acids), D18019 (extended L270 linker between closest ferulic acid and free amino group), D18080 (three free amino groups with L90 spacing).

4. From the intermediate D18080 with six ferulic acids and three free aminogroups two conjugates were prepared by further solution phase labeling. D18081 with three Texas-Red-X's and D18096 with three 7-hydroxy coumarins. This illustrates how conjugates can be labeled in solution with two different substituents. The advantage is that the intermediate D18080 can be purified prior to the final labeling, an advantage when using labile or expensive labels such as Texas Red.

5. The synthesis of D17152 illustrates the extent of solid phase synthesis chemistries that can be applied to linkers in solution, followed by repeated precipitation by diethyl ether to remove low molecular weight reactants and solvents: On solid phase NH2-Lys(NH2)-(L30-Lys(NH2))4-L30-Lys(Fmoc) was prepared and cleaved from the resin. Boc-L30 linkers were then coupled to the six free amino groups in solution. The intermediate was precipitated and dissolved in 5% m-cresol in TFA twice. Then ferulic acid labeling was performed as in 2 on the now L30 extended amino groups, followed by ethanolamine and ethylenediamine scrubbing as in 3 and finally 3 TFA precipitations as in 1.

6. Fragment couplings were carried out between amino substituted intermediates and "betaalaanhydride" activated intermediates. D17126 with three fluoresceins further carries an N-terminal betaalanine-N,N-diacetic acid. By activation (NMP:diisopropyl carbodiimide:pyridine; 88:10:2) for 10 min a cyclic "betaalaanhydride" is formed that can be used for coupling to amino groups. This gave D17134 (six ferulic acids with L30 spacing) from D17120, D17148 (six ferulic acids in three pairs with L30 spacing) from D17139, D17156 (six L30 extended ferulic acids) from D17152 and D18003 (with six 7-hydroxy coumarins) from D17192. The advantage of such fragment coupling is that intermediates can be HPLC purified prior to coupling, affording large and complex, yet quite pure conjugates. Another advantage is that a single intermediate as D17126 can be used to prepare a series of related, but different conjugates.

7. Dextran conjugates with a single substituent includes the control fluorescein-only conjugates D17132, D18130 and D18088 (all Dex70 conjugates from D17127 via cystein coupling), D17162 (dex270 conjugate from D17127) and D18086 (from D18085 with less efficient coupling via diamino proprioninc acid). These were used as controls to demonstrate that fluorescein-only conjugates did not work. Conjugates were also prepared this way, by coupling multiple intermediate conjugates to dextran. These include D18133 (dex 70 with L30 spaced tyrosine-fluorescein conjugate D18132) and D18130 (dex 70 with tyrosine-fluorescein conjugate D18128. The advantage of coupling a single conjugate with both HRP substrates and labels, is that a fixed ratio between the two substituents is assured.

8. Dextran conjugates with two different substituents include D17130, D18077, D18079, D18090, D18122 and D21008 that are all dex70 with six ferulic acid linker D18074 and tri-fluorescein linker D17127 (or reproductions of linkers). There was good reproducibility between D17130, D18077, D18079 and D21008 with around 100 ferulic acids and 70 fluoresceins, whereas D18122 was coupled with further excess of fluorescin linker to give a conjugate with approx 100 ferulic acids and fluoresceins each. D17128 resembles D17130, but the ferulic acid linker used (D17093) has ferulic acids attached to PNA backbone rather than lysine side chains. The conjugate D18031 is also with D17127, but with the L270 extended ferulic acid linker D18019. This conjugate was an attempt to make ferulic acids more readily accessible to HRP enzymes.

Examples of Synthesis Procedures for Selected Compounds
D19185 Boc-(Lys(2-C1-Z))3-L150-Lys(Fmoc) is prepared on solid phase. The Fmoc group is removed, followed by fluorescein labeling as described above. The intermediate NH2-((Lys(NH2))3-L150-Lys(Flu) results from cleavage from resin. It is precipitated with diethyl ether, dissolved in TFA, precipitated then dissolved in NMP and made basic with DIPEA. This solution is mixed with an equal volume of 0.2 M ferulic acid in NMP activated by HATU and DIPEA. After 10 min the labeling is complete and the crude product is further "scrubbed" by addition of ethylene diamine to a concentration of 10% for 5 minutes. Following precipitation with diethyl ether, the product is further dissolved in TFA and precipitated with diethyl ether three times to remove low molecular weight debris. Prior to "scrubbing" with ethylene diamine, mass spectroscopy shows two kinds of adducts (and combinations thereof): +(176)n indicating extra ferulic acids (phenolic esters on other ferulic acids and fluorescein) and +98 (N,N'-tetramethyl uronium adducts, likewise on unprotected phenolic groups). These are completely removed by the ethylene diamine treatment, and active esters and ferulic acid oligomers are likewise decomposed.

The synthesis of D19185 is illustrated in FIG. 1.

The following fluorescein-Ferulic acid conjugates were made according to this scheme: D17157, D17158, D19112, D19185, D18015, D20086, D20118, D20120, D19037 and D18157 (detailed synthesis some of these conjugates is described below). Ferulic acid conjugates with other labels include: D19048 (lissamine labeled); D19059, D18141 and D19040 (DNP labeled). Conjugates with sinnapinic acid in place of ferulic acid were prepared by the same methodology and include 0328-018 and D21028 with fluorescein labels and the DNP labeled D21048. D21020 is with is with three caffeic acids and a fluorescein, D18146 with six 4-aminocinnamic acids and three fluoresceins and are both prepared by the same strategy.

D17158 MBHA resin was downloaded with Fmoc-Lys(ivDDE) to a loading of 150 micro mol/g. 200 mg resin was de-Fmoc'ed with 20% piperidine in NMP, the subjected to one coupling with Boc-L30-OH (1.5 mL 0.26 M in NMP, preactivated with 0.9 equi. HATU, 2 equivalents DIPEA for 2 min) for 20 min. The ivDDE group was removed with 5% hydrazine in NMP, and the lysine side chain was labelled with carboxy fluorescein (Flu) (1.5 mL 0.2 M in NMP, preactivated for 2 min with 0.9 equi. HATU, 2 equi DIPEA) for 2×20 min. The resin was treated with 20% piperidine in NMP, NMP, DCM then DCM. The intermediate product H-L30-Lys(Flu)-$NH_2$ was cleaved of the resin with TFA:TFMSA:mCresol (7:2:1, 1.5 ml for 1 h), precipitated with diethyl ether, re-suspended in TFA, precipitated with diethyl ether, re-suspended in NMP and again precipitated with diethyl ether. It was made basic with 100 microL DIPEA and dissolved directly in 0.5 mL 0.3M Ferulic acid preactivated with 0.9 equi. HATU and 2 equi. DIPEA. After 25 min the crude product was precipitated with diethyl ether, dissolved in 450 microL NMP and 50 microL ethylenediamine. After 5 min the product was precipitated with diethyl ether, dissolved in 15% acetonitril in water (8 mL) and acidified with 100 microL TFA and subjected to RP-HPLC purification.

D17157 MBHA resin was downloaded with Boc-Lys(Fmoc) to a loading of 100 micro mol/g. 100 mg resin was subjected to 5 coupling cycles with Boc-L30-OH (a. Coupling with Boc-L30-OH as in 1. b. Capping with 2% acetic anhydride in NMP:Pyridine 1:1, 2 min. c. De-Bc with 5% mCresole in TFA 2×5 Min.). The lysine side chain was De-Fmoc'ed and labelled with carboxy fluoresceine, as in 1. The intermediate product H-L150-Lys(Flu)-$NH_2$ was cleaved of the resin, and labelled N-terminally with Ferulic Acid and purified as in 1.1.

D16127 Boc-L90-Lys(Fmoc)-L90-Lys(Fmoc)-L90Lys(Fmoc) was prepared on 0.5 g MBHA resin with standard solid phase chemistry (as in 1.1. and 1.2). Fmoc groups were removed from lysine side chains with 20% piperidine in NMP and the compound was subjected to repeated carboxy fluorescein labelling (3×30 min). Following removal Boc groups with TFA, the N-terminal was labeled on solid phase with betaalanine-N,N-di acetic acid (betaala) tert—butyl ester. Following cleavage from resin and HPLC purification, betaala-L90-Lys(Flu)-L90Lys(Flu)-L90-Lys(Flu)-NH2 was isolated.

D17127 Boc-L90-Lys(Fmoc)-L90-Lys(Fmoc)-L90Lys(Fmoc) resin was prepared and labeled with fluorescein using the procedure described in 1.3. Following removal Boc groups the N-terminal was labeled with N-Boc-S(4-Methoxybenzyl)-Cys-OH. The compound was cleaved from the column and purified by HPLC:

D18074/D17128 To MBHA resin was sequentially coupled Boc-Lys(Fmoc) (2 cycles), Boc-L30-OH (5 cycles) and Boc-Lys(2ClZ)-OH. The intermediate product was cleaved from the resin in the presence of 10% thioanisol scavenger to remove 2ClZ-groups. The N-terminal and the 5 de-protected lysine side chains were labeled with Ferulic acid as in 1.1 (2×30 Min). The Fmoc group on the N of the C-terminal Lysine residues was then removed with 10% ethylene diamine in NMP prior to purification.

D17134 betaala-L90-Lys(Flu)-L90Lys(Flu)-L90-Lys(Flu)-NH2 (D16126) (see 1.4 above) 500 nmol was dissolved in 88 microL NMP and 2 microL pyridine, and converted to cyclic anhydride by reaction with 10 microL diisopropyl carbodiimide for 10 min. The anhydride was precipitated with diethyl ether, and the pellet was dissolved in 100 microL NMP comprising 250 nmol Fer-(Fer-L30)$_5$-Lys(NH$_2$)-NH$_2$. After 20 min 5 microL ethylene diamine was added, and after 5 min the product was precipitated with diethyl ether, acidified and HPLC purified.

D18044 Ac-(Tyr(2BrZ)-L30)$_6$-L90-Lys(Fmoc)-L90-Lys(Fmoc)-Lys(Fmoc) was prepared on MBHA resin. On solid phase the Fmoc groups were removed, and the lysine side chains labeled with carboxy fluorescein. Following cleavage from the resin, the product was HPLC purified.

D17140 Boc-Lys(2ClZ)-L60-Lys(2ClZ)-Lys(2ClZ)-L60-Lys(2ClZ)-Lys(2ClZ)-L30-Lys(Fmoc) was prepared on MBHA resin. Following cleavage from the resin, the intermediate product H-Lys(NH$_2$)-L60-Lys(NH$_2$)-Lys(NH$_2$)-L60-Lys(NH$_2$)-Lys(NH$_2$)-L30-Lys(Fmoc) was isolated by precipitation, and labeled with Ferulic acid as in 1.1. The final product was isolated by HPLC.

D18090 Dextran MW 70 kDa, activated with divinyl sulphone, 10 nmol, was reacted with Fer-(Fer-L30)$_5$-Lys(NH$_2$)-NH$_2$ (D18074) (see (see 1.4 above). 500 nmol, in a total volume of 300 microL 0.16M NaHCO$_3$ pH 9.5 for 30 min at 40 C. After a slight precipitation was observed, further 100 microL water was added and the reaction was allowed to proceed for another 30 min. Further 200 microL 0.15 M NaHCO$_3$ was added together with 500 nmol H-Cys-L90-Lys(Flu)-L90Lys(Flu)-L90-Lys(Flu)-NH2 (D17127) (see 1.5 above). After 1 h at 40 C, the reaction mixture was quenched by addition of 50 microL 0.165M cystein for 30 min, solution was filtered, and the product was purified by FPLC on superdex 200 with 20% EtOH in aqueous solution containing 10 mM CHES, pH 9.0, and 0.1 M NaCl. The product eluted was a Dextran conjugate comprising around 56 Fluorescein and 113 Ferulic Acid residues.

D19112 On solid phase MBHA resin Boc-Lys(2Clz)-Lys(2ClZ)-L150-Lys(Fmoc) was prepared using standard solid phase Boc chemistry. The Fmoc group was removed using 20% piperidine in NMP (2×5 min), and the free amino group was labeled with carboxy fluorescein (0.2 M carboxy fluorescein activated with 0.9 equi. HATU and 1 equi. DIPEA in NMP for 3 times 20 min). The resin was then subjected to treatment with 20% piperidine in NMP for 2×5 min. Cleavage from the resin was performed in TFA:TFMSA:m-cresole: thioanisole (6:2:1:1) mixture for one hour and resulted in the intermediate product H2N-Lys(NH2)-Lys(NH2)-L150-Lys(Flu). This product was dissolved in TFA, precipitated with diethyl ether, and then dissolved in NMP and again precipitated with diethyl ether. The precipitate was then dissolved in 0.3 M ferulic acid activated with 0.9 equivalents HATU and two equivalents Diisopropyl-ethyl-amine. After 10 min reaction, the product was precipitated with diethyl ether and then dissolved in 10% ethylenediamine in NMP for 2 min. The final product was then precipitated with diethyl ether, dissolved in 30% acetonitrile in water and HPLC purified on a C18 column.

D19185, D20068 and D20171 were prepared in the same way as D19112, with the introduction of an additional Lys(Fer) group.

D21020: Caf-Lys(Caf)-Lys(Caf)-L150-Lys(Flu), was prepared as D19185. Following solid phase synthesis, caffeic acid labeling was performed in solution.

0328-018: Sin-Lys(Sin)-Lys(Sin)-L150-Lys(Flu) was prepared as D19185. Following solid phase synthesis, sinapinnic acid labeling was performed in solution D20118: was prepared in the same way as D19112, using L60 linker.

D20086: was prepared in the same way as D19112, using L30 linker.

D20120: was prepared in the same way as D19112, using L30 linker, and, additionally, a glutamic acid residue. Boc-Glu(O-benzyl) was used for solid phase synthesis to build in the glutamic acid residue.

D19048: On 0.5 g MBHA resin Boc-$L_{150}$-Lys(Fmoc) was prepared. The Fmoc group was removed and the lysine side chain amino group was labeled with Lissamin (Molecular Probes product nr. L20, rhodamine B sulphonyl chloride) using 100 mg in 2 mL NMP with addition of 80 microL DIPEA for 3 times 10 min. The Boc group was then removed with TFA, and Boc-Lys(2ClZ) was coupled to the N terminal. The intermediate product $H_2N$-Lys($NH_2$)-L150-Lys(Lissamine) was cleaved from the resin with TFA:TFMSA:m-cresole:thioanisole (6:2:1:1) and labeled with ferulic acid as described for D19112 to give Fer-Lys(Fer)-L150-Lys(Lissamin). The product was purified by RP-HPLC, splitting into two separate peaks representing different isomers of Lissamine. The first isomer turned almost colorless in basic aqueous solution, and was discharged. The second isomer retained color and fluorescence in basic aqueous solution and was collected.

D19059: was prepared in the same way as D19112, but labeled on the C-terminal lysine side chain amino group on solid phase with DiNitroPhenyl using 100 mg 2,4-dinitrofluorobenzen in 1.5 mL NMP with addition of 50 microL DIPEA for 2 times 20 min.

D18126: Fer-Lys(Fer)-L30-Lys(Fer)-L30-Lys(Fer)-Lys(Fer)-L30-Lys(Fer)-L120-Lys(Flu)-L90-Lys(Flu)-L90-Lys(Flu)=Fer-(Lys(Fer)-L30)5-(L90-Lys(Flu))3. This extended conjugate was prepared by the same route as D19112: Boc-(Lys(2ClZ)-L30)5-(L90-Lys(Fmoc))3 was prepared on solid phase. The three Fmoc groups were removed with piperidine in NMP, and three carboxy fluoresceins introduced as in D19112. The intermediate product, NH2-(Lys(NH2)-L30)5-(L90-Lys(Flu))3 was cleaved of the resin and labeled with Ferulic acid at the N-terminal and 5 free lysine side chains, washed with 10% ethylenediamine in NMP, precipitated from TFA and HPLC purified.

D18146: ACim-(Lys(ACim)L30)5-(L90-Lys(Flu))3 was prepared on the same Lysine-Linker skeleton as D18126. Following cleavage from solid phase, the intermediate fluorescein labeled linker was dissolved in NMP and made basic with DIPEA. 4-amino-cinnamic acid, 0.1 M in NMP was activated with 0.9 equi. HATU and 3 equi DIPEA for 30 seconds, and added to the linker. The reaction was quenched after 2 min by addition of ethylenediamine to a final concentration of 10%. Following precipitation the product was purified by RP-HPLC.

D18074: Fer(Lys(Fer)-L30)5-Lys(NH2). this intermediate linker with 6 ferulic acids and a free lysine side chain amino group was prepared by solid phase chemistry, using a C terminal Boc-Lys(Fmoc) followed by alternating coupling with Boc-L30 linker and Boc-Lys(2ClZ). Following cleavage from resin, the intermediate product NH2(Lys(NH2)-L30)5-Lys(Fmoc) was labeled with ferulic acid in solution as described for D19112. In the final treatment with 10% ethylenediamine, the Fmoc group was also removed. This homo ferulic acid oligomer was used in the preparation of dextran conjugate D21008.

D18118: NH2-Cys-(L90Lys(Flu)) This intermediate trifluorescein linker was prepared directly on solid phase, using Boc-Lys(Fmoc) to introduce lysines, that following removal of the Fmoc were labeled with carboxy fluorescein. The N-termina cystein was introduced using Boc(S-p-methoxybenzyl) cysteine.

D18044: On solid phase Fer-(Tyr-L30)5-(L90-Lys(Flu))3 was prepared as D18126. N-Boc-O-2BrZ tyrosine was used to introduce the tyrosines. Following cleavage from the resin the product was HPLC purified.

D21008: Dex70 conjugate with D18074 and D18118. 10 nmol vinyl sulphone activated 70 kDa dextran in 140 microL water was mixed with further 200 microL water and 60 microL 0.8 M sodium hydrogen carbonate, pH 9.5. This mixture was used to dissolve 500 nmol freeze dried D18074. The reaction mixture was maintained at 40 C for 60 min, then further 500 mmol D18118 dissolved in 250 microL water was added to the reaction mixture together with further 50 microL 0.8M sodium hydrogen carbonate, pH 9.5. After additional 60 min reaction at 40 C, the reaction was stopped by addition of 70 microL 0.165 mM cystein in 0.8 M sodium hydrogen carbonate, pH 9.5. The conjugate was purified on superdex 200, using 10 mM CHES pH 9.0, 100 mM NaCl in 20% ethanol in water as eluent. This resulted in a first peak containing the conjugate, followed by unconjugated linkers. Based on a total recovery of 81% of fluorescien and ferulic acid, and assuming the same recovery rate (81%) for the dextran conjugate, a ratio of 111 ferulic acids and 83 fluoresceins per dextran was calculated, corresponding to $(D18074)_{18.5}$-Dex70-$(D18118)_{27.7}$.

D19059: On 0.1 g of MBHA resin with standard solid phase chemistry Boc-Lys(2ClZ)-Lys(2ClZ)-$L_{150}$-Lys(Fmoc) was prepared. The Fmoc protected Lysine side chain was deprotected with 20% piperidine in NMP (2×5 min) and subjected to labeling with 150 mg 2-4-dinitro-fluorobenzene dissolved in 1.5 ml NMP 1.5 mL and 50 µL DIPEA for 2×20 min. The resin was treated with 20% piperidine in NMP, NMP and DCM.

The intermediate product was cleaved of the resin with TFA: TFMSA: thioanisol: m-cresol (6:2:1:1, 1.5 mL, for 1 h), precipitated with diethyl ether, resuspended in TFA, precipitated with diethyl ether, resuspended in NMP and again precipitated with diethyl ether. It was made basic with 100 µL DIPEA and dissolved directly in 0.5 mL 0.3 M Ferulic acid preactivated with 0.9 equi HATU and 2 equi DIPEA. After 10 min. the crude product was precipitated with diethyl ether, redissolved in 900 µL NMP and 100 µL ethylendiamine. After 2 min. the product was precipitated with diethyl ether. Resuspended in TFA, precipitated with diethyl ether, dissolved in 22% acetonitril in water (8.2 mL) and subjected to RP-HPLC purification.

Yield 8 µmol, MS found 3582 (M+Na), calc 3558.784 for Fer-Lys(Fer)-Lys(Fer)-$L_{150}$-Lys (DNP).

D19112: On 1 g of MBHA resin with standard solid phase chemistry Boc-Lys(2ClZ)-Lys(2ClZ)-$L_{150}$-Lys(Fmoc) was prepared. The Fmoc protected Lysine side chain was deprotected with 20% piperidine in NMP (2×5 min) and subjected to repeated carboxy fluorescein labeling (3 mL 0.2 M in NMP, preactivated for 2 min with 0.9 equi HATU, 1 equi DIPEA) 3×20 min. The resin was treated with 20% piperidine in NMP then washed with NMP, DCM and TFA. The intermediate product was cleaved of the resin with TFA: TFMSA: thioanisol: m-cresol (6:2:1:1, 3 mL, for 1 h), precipitated with diethyl ether, resuspended in TFA, precipitated with diethyl ether, resuspended in NMP and again precipitated with diethyl ether. It was made basic with 200 µL DIPEA and dissolved directly in 2 mL 0.3 M Ferulic acid preactivated with 0.9 equi HATU and 2 equi DIPEA. After 10 min. the crude product was precipitated with diethyl ether, redissolved in 1350 µL NMP and 150 µL ethylendiamine was added. After 2 min. the product was precipitated with diethyl ether. Resuspended in TFA, precipitated with diethyl ether, dissolved in 25% acetonitril in water (24 mL) and subjected to RP-HPLC purification.

Yield 19 μmol, MS found 3749, calc 3750.998 for Fer-Lys (Fer)-Lys(Fer)-L$_{150}$-Lys (Flu).

D19185: D19185 was prepared analogously to D19112, by solid phase synthesis, followed by labelling with Ferulic acid in solution. MS found 4054.

D19037: D19037 was prepared analogously to D19112, by solid phase synthesis, followed by labelling with Ferulic acid in solution. MS found 3447.

D18126: On MBHA resin with standard solid phase chemistry Boc-(Lys(2ClZ)-L$_{30}$)$_5$L$_{90}$-Lys(Fmoc)-L$_{90}$Lys(Fmoc)-L$_{90}$ Lys(Fmoc)) was prepared. The Fmoc protected Lysine side chain was deprotected with 20% piperidine in NMP (2×5 min) and subjected to repeated carboxy fluorescein labeling (3 mL 0.2 M in NMP, preactivated for 2 min with 0.9 equi HATU, 1 equi DIPEA) 3×20 min. The resin was treated with 20% piperidine in NMP then washed with NMP, DCM and TFA. The intermediate product was cleaved of the resin with TFA: TFMSA: thioanisol: m-cresol (6:2:1:1, 3 mL, for 1 h), precipitated with diethyl ether, resuspended in TFA, precipitated with diethyl ether, resuspended in NMP and again precipitated with diethyl ether. It was made basic with 200 μL DIPEA and dissolved directly in 2 mL 0.3 M Ferulic acid preactivated with 0.9 equi HATU and 2 equi DIPEA. After 10 min. the crude product was precipitated with diethyl ether, redissolved in 1350 μL NMP and 150 μL ethylendiamine was added. After 2 min. the product was precipitated with diethyl ether. Resuspended in TFA, precipitated with diethyl ether, dissolved in 25% acetonitril in water (24 mL) and subjected to RP-HPLC purification.

Yield 2 μmol, MS found 10666.

Biding Agents

Goat-Anti-Mouse-Dex70-HRP (D18033/D18175)

13.7 nmol divinylsulphone were activated 70 kDA MW dextran and reacted with 602 nmol HRP were in 600 microL buffer (100 mM NaCl, 25 mM NaHCO$_3$, pH 9.5) for 3 h at 30 C. Then 41.1 nmol Goat-anti-Mouse F(ab)$_2$ antibody in 105 microL water was added, and the reaction was continued for additional 16 h. The reaction mixture was quenched by addition of 70 microL 0.165M cystein for 30 min and the product was purified on superdex 200 in 100 mM NaCl, 10 mM HEPES pH 7.2. The eluded product was a Dextran conjugate comprising Goat-anti-Mouse (GaM) and HRP (8 HRP and 1,3 antibody pr conjugate; ratio dex/GaM/HRP=1/1.1/7.5).

Anti-FITC-Dex70-HRP (D18058/D18144)

10 nmol divinylsulphone activated 70 kDA MW dextran and 440 nmol HRP were reacted in 400 microL buffer (100 mM NaCl, 25 mM NaHCO$_3$, pH 9.5) for 3 h at 30 C. Then, 30 nmol Anti-Mouse F(ab)$_2$ antibody in 80 microL water was added, and the reaction was continued for additional 90 min at 40 C. The reaction mixture was quenched by addition of 50 microL 0.165M cystein for 30 min and the product was purified on superdex 200 in 100 mM NaCl, 10 mM HEPES pH 7.2. The eluded product was a conjugate of Dextran with anti-FITC and HRP (9 HRP and 1.5. antibody per conjugate; Dex/anti-FITC/HRP Ratio=1/2/9).

Rabbit-Anti-FITC F(ab')$_1$-HRP conjugate (D19142/D19154)

Polyclonal rabbit-anti_FITC IgG antibody was digested with pepsin for 4 h at 37 C. and subjected to purification on superdex 200 to remove pepsin and Fc fragments.

The F(ab')$_2$ fragment was further dialysed against 5 mM EDTA in 0.2 M sodium phosphate, pH 6.0. The solution was concentrated with Amicon Ultra spin columns to a protein concentration of 25 g/L. To 6.0 mL of said solution (150 mg F(ab')$_2$) was added 487 microL 50 mg/mL DTT and 423 microL 56 mM 2-mercaptoethanol, both in water. The reaction mixture was gently stirred for 40 min at room temperature, and immediately after purified on PD-10 column with 5 mM EDTA in 0.2 M sodium phosphate, pH 6.0. 118 mg F(ab'), was recovered in 8.0 mL buffer.

HRP (Servac), 250 mg, was dissolved in 2.5 mL 0.15 m NaCL, 0.05M potassium phosphate pH 8 and dialysed against the same buffer. Following dialysis the enzyme solution was concentrated and adjusted to a concentration of 40 mg/mL. To 3.21 mL, 128.6 mg HRP solution was added 860 micoL 15 mg/mL SMCC, and the reaction was allowed to proceed for 30 min in the dark at room temperature. The SMCC activated HRP enzyme was purified on PD-10 column with 0.15 m NaCL, 0.05M potassium phosphate pH 8. 126.9 mg were recovered in 7.9 mL.

To the 8.0 mL of F(ab')$_1$ was added 6.25 mL of the SMCC activated HRP solution, and the total volume was adjusted to 43.8 mL with 0.15 m NaCL, 0.05M potassium phosphate pH 8. The reaction between antibody fragment and enzyme was carried out for 210 min in the dark at room temperature. The reaction was then quenched by addition of 343 microL 25 mg/mL cysteamine in water for 15 min at room temperature, and the reaction mixture was stored in the cold over night awaiting purification. The sample was concentrated to 8 mL, and in 4 portions applied to a superdex 200 column and eluded with 150 mM NaCL, 50 mM Tris, pH 7.6. The product eluded in the first peak, followed by a peak of un-reacted antibody and enzyme. 100 mg of conjugate was isolated in several fractions. UV-measurements at 280 nm/403 nm showed antibody enzyme ration between 0.8 and 1.2.

Goat-Anti-Mouse F(ab')$_1$-HRP (D19150/D19147)

Goat-anti-Mouse F(ab')$_1$-HRP was prepared as Rabbit-anti-FITC F(ab')$_1$-HRP, by reduction of F(ab')$_2$ with DTT and mercaptoethanol and coupling to SMCC activated HRP. As with Rabbit-anti-FITC F(ab')$_1$-HRP, 12 equivalents of SMCC was used for HRP activation and a 1:1 molar ration between F(ab')$_1$ and HRP was used.

Goat-anti-Rabbit F(ab')$_1$-HRP (AMM 279.168)

Goat-anti-Rabbit F(ab')$_1$-HRP was prepared as Rabbit-anti-FITC F(ab')$_1$-HRP, by reduction of F(ab')$_2$ with DTT and mercaptoethanol and coupling to SMCC activated HRP. As with Rabbit-anti-FITC F(ab')$_1$-HRP, 12 equivalents of SMCC was used for HRP activation and a 1:1 molar ration between F(ab')$_1$ and HRP was used.

Binding Agent Goat-Anti-Mouse F(ab')$_1$-HRP Conjugate (D19150)

This was prepared by the same procedure as D19142 (with GaM instead of FITC).

Binding Agent Rabbit-Anti-DNP F(Ab')$_1$-HRP Conjugate (D19053

This binding agent was prepared by the same procedure as D19142 using a polyclonal rabbit anti DNP antibody.

Binding Agent Rabbit-Anti-FITC F(ab')$_1$-Alkaline Phosphatase Conjugate (D20036)

Rabbit-anti-FITC was pepsin digested and reduced to F(ab)1 as described for D19142. 44.9 mg of the fragmented antibody in 4.23 mL buffer was used for the conjugation. Alkaline Phosphatase (Boehringer, MW 140.000) 56 mg in 2.8 mL buffer (25 mM borate, 200 mM NaCl, 5 mM MgCl2, 0.2 mM ZnCl2, pH 8.2) was reacted with 1.6 mg SMCC (12 equivalents relative to enzyme) dissolved in 107 microL DMSO for 25 min at room temperature in the dark. This activated enzyme solution was subjected to gel filtration using a buffer with 0.1 M TRIS, 0.2 M NaCl, 5 mM MgCl2, 0.2 mM ZnCl2, pH 8.2. 55.3 mg enzyme was isolated in a volume of 7 mL. The fragmented antibody and activated enzyme were immediately mixed together and further 2.47 mL 0.1 M TRIS, 0.2 M NaCl, 5 mM MgCl2, 0.2 mM ZnCl2, pH 8.2 was added. The mixture was allowed to react for 150 min at room temperature, and was then quenched by addition of 11.2 mg cysteamine for 15 min. The product was purified on a Superdex 200 column using 0.1 M TRISI, 5 mM MgCl2, 0.2 mM ZnCl2, pH 7.2, eluding as a single broad peak. Individual fractions assayed for AP activity and FITC binding in an IHC assay using D19150 to deposit reporter D19185, followed by the different fractions and finally Liquid Permanent red as chromogen. All major product containing fractions perform equally well and were pooled.

Binding Agent Goat Anti-Mouse Antibody Conjugated with Dex70 Conjugated with HRP (D20052)

11 nmol 70 kDA MW dextran was reacted with 484 nmol HRP in 316 microliters of buffer A (100 mM NaCl, 25 mM NaHCO$_3$, pH 9.5) for 3 h at 30 C. Thereafter 66 nmol Goat-anti-Mouse-F(ab)$_2$ in 169 microL water was added to the dextran-HRP conjugate and allowed to react for 1 h. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Mouse (GaM) and HRP. The use of a relatively short conjugation time, in combination with high molecular weight optimized purification allowed separating the final conjugate product into 15 fractions based on conjugate size. Measurements on individual product fractions, as well as fractions containing non-conjugated antibody and HRP, showed the conjugate recovery of 81%, corresponding to 8.91 nmol dextran. Collectively the conjugate fractions (fractions 7 to 22 of the eluate) contained 72.3 nmol HRP and 7.9 nmol antibody corresponding to 8.1 HRPs/dextran and 0.88 antibodies/dextran in average. Fractions 7-8 produced an initial peak, followed by a broad peak (fractions 9-17) that trailed off (fractions 18-22).

Goat Anti-Mouse Antibody Conjugated with Dex70 Conjugated with HRP (D20168)

This conjugate was produced in exactly the same way as D20052. To obtain a product with a uniform number of HRPs only fractions 9 and 10 were collected and pooled together.

Goat Anti-Mouse Antibody Conjugated with Dex-150 Conjugated with HRP (D20060)

This binding agent was prepared as D20052, though a larger molecular weight (150 kDa) dextran was used. During purification the vast majority of conjugate was eluded in a single peak in the first 4 fractions. Calculations showed 16.5 HRPs and 1.8 antibodies per dextran molecule in average.

Goat-Anti-Mouse Antibody Conjugated with Dex150 Conjugated with HRP (L348.121)

5.13 nmol 150 kDA MW dextran was reacted with 484 nmol HRP in 300 microliters of buffer, (100 mM NaCl, 25 mM NaHCO$_3$, pH 9.5) for 3 h at 40 C. Thereafter 66 nmol Goat-anti-mouse F(ab)2 in 169 microL of water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Mouse F(ab)2 and HRP. The product was divided into 3 fractions based on conjugate size: The first fractions (8-11) containing the largest conjugates, the trailing fractions with smaller conjugates, and un conjugated proteins. Measurements on individual product fractions, as well as fractions containing non-conjugated antibody and HRP, showed a total conjugate recovery of 87%. Assuming direct proportionality between incorporated HRP and Dextran showed that fractions 8-11 contained 20.6 HRPs and 2.32 antibodies per Dextran. fractions 10-11 contained 10.9 HRPs and 0.96 antibodies per Dextran. Only Fractions 8-11 were used for experiments.

This conjugate exemplifies how use of larger dextran conjugates allows incorporation of more HRPs.

Goat Anti-Rabbit Antibody Conjugated with Dex70 Conjugated with HRP (L348.111, Fractions 10-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 44 nmol Goat-anti-Rabbit 196 microL water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising Goat-anti-Rabbit (GaR) and HRP. The product was divided into 4 fractions based on conjugate size: The first two fraction containing product (Frac. 8-9) eluded as a first peak, presumably containing some cross linked conjugates, then followed by a broad shoulder that was divided into fractions 10-11 (homogeneous large conjugates) and fractions 12-21 (smaller variable conjugates) and finally unconjugated enzymes and antibodies in fractions 22-42. Measurements on individual product fractions, as well as fractions containing non-conjugated antibody and HRP, showed a total conjugate recovery of 87%. Assuming direct proportionality between incorporated HRP and Dextran showed that fractions 10-11 contained 10.9 HRPs and 0.96 antibodies per Dextran. Only these two fractions were used for experiments.

Anti-HER2-Antibody Conjugated with Dex70 Conjugated with HRP (D21100, Fractions 9-10)

4.6 nmol 70 kDA MW dextran was reacted with 202 nmol HRP in 125 microliters of buffer A (100 mM NaCl, 25 mM NaHCO$_3$, pH 9.5) for 3 h at 30 C. Thereafter 18 nmol anti-Her2 in 489 microL of water was added to the dextran-HRP conjugate and the mixture was allowed to react for further 21 h at 30 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiHer2 and HRP. The product was divided into 4 fractions based on conjugate size: The first two fraction containing product (Frac. 7-8) eluded as a first peak, presumably containing some cross linked conjugates, then followed by a broad shoulder that was divided into fractions 9-10 (homogeneous large conjugates) and fractions 11-19 (smaller variable conjugates) and finally unconjugated enzymes and antibodies in fractions 20-41. Measurements on individual product fractions, as well as fractions containing non-conjugated antibody and HRP, showed a total conjugate recovery of 68%. Assuming direct proportionality between incorporated HRP and Dextran showed that fractions 9-10 contained 9.1 HRPs and 0.6 antibodies per Dextran. Only these two fractions were used for experiments.

antiFITC Antibody Conjugated with Dex70 Conjugated with HRP (AMM 353-022 Fractions 8-11.)

11 nmol 70 kDA MW dextran was reacted with 484 nmol HRP in 316 microliters of buffer A (100 mM NaCl, 25 mM NaHCO$_3$, pH 9.5) for 3 h at 40 C. Thereafter 66 nmol anti-FITC in 196 microL of water was added to the dextran-HRP conjugate and allowed to react for further 1 h at 40 C. The reaction mixture was quenched by addition of 70 microL 0.165M cystein for 30 min and the product was purified on Sephacryl 300 (GE Medical) in buffer B (100 mM NaCl, 10 mM HEPES pH 7.2). The eluded product was a dextran conjugate comprising antiFITC and HRP. The product was divided into 3 fractions based on conjugate size: The first fractions (8-11) containing product eluded as a first peak, then followed by a broad shoulder (smaller variable conjugates, frac. 12-27) and finally unconjugated enzymes and antibodies in fractions 28-45. Measurements on individual product fractions, as well as fractions containing non-conjugated antibody and HRP, showed a total conjugate recovery of 90%. Assuming direct proportionality between incorporated HRP and Dextran showed that fractions 10-11 contained 11.7 HRPs and 0.80 antibodies per Dextran. Only these two fractions were used for experiments.

Other Reagents
Anti-cytokeratin monoclonal antibody (Dako M3515)
incubation media (a) (ABCPT-buffer): 0.1% 4-aminoantipurine, 0.2% Procline 2% BSA, 0.2% Casein, 2% PEG, 0.1% Tween20, 0.1 M NaCL, 10 mM HEPES, pH 7.2.
Incubation media (b): 50 mM imidazole HCl pH 7.5, 0.1% Nonidet P40, 0.1%, benzalkonium chloride, 0.005% (1.5 mM) hydrogen peroxide,
DAB chromogen solution (Dako K3465)
LPR chromogen solution (Dako K0640)
Haematoxilin counterstain (Dako S3301)
Wash buffer (Dako S3306)
Target retrieval solution (Dako S1699)

Example 1

Dot Size as Function of the Amount of Reporter, DAB and $H_2O_2$ in Incubation Media or Incubation Time General Procedure:
Staining experiments were run on formalin fixed paraffin embedded tissue. As pretreatment slides were de-paraffinized in 2 baths of xylene (5 min each), two baths of 96% ethanol, 2 baths of 70% ethanol (2 min each). The slides were then boiled in a microwave oven for 10 min in target retrieval solution (Dako S 1699). The slides were allowed to cool, endogenous peroxidase activity was quenched with 10% hydrogen peroxide for 2 min Experiment 1
All slides were: incubated with an experimental monoclonal mouse antibody directed at the C-terminal of the HER2 protein was used, "clone 6C2", The following protocol was used: Incubation with clone 6C2, 55 picoM for 3 min, washed with wash buffer (Dako S3306) then incubation with GaM/HRP (D20052 frac. 8) in concentration 370 picoM for 3 min, then washed. Then the slides were subjected to a deposition step, a reporter binding agent step (all reporters, D19112, D20068, D20086, D20118, D20120 were used in concentration 10 µM) and a staining step with LPR chromogen as detailed in table 1. Washing steps were used between each step.

TABLE 1

| | Deposition media (step b) | Detection (step c) Reporter binding agent (step c') | Stain (step c") |
|---|---|---|---|
| Slide 1 | D19112: DAB 0.28 mM, $H_2O_2$ 1.5 mM, 10 min | D20036 50 nM, 10 min | LPR 10 min |
| Slide 2 | D19112: DAB 0.28 mM, $H_2O_2$ 1.5 mM, 10 min | D20036 50 nM, 10 min | LPR 5 min |
| Slide 3 | D19112: DAB 0.28 mM, $H_2O_2$ 1.5 mM, 10 min | D20036 50 nM, 10 min | LPR 3 min |
| Slide 4 | D19112: DAB 0.28 mM, $H_2O_2$ 1.5 mM, 10 min | D20036 50 nM, 10 min | LPR 2 min |
| Slide 5 | D19112: DAB 0.28 mM, $H_2O_2$ 1.5 mM, 10 min | D20036 50 nM, 10 min | LPR 1 min |
| Slide 6 | D19112: DAB 0.28 mM, $H_2O_2$ 1.5 mM, 5 min | D20036 50 nM, 10 min | LPR 10 min |
| Slide 7 | D19112: DAB 0.28 mM, $H_2O_2$ 1.5 mM, 3 min | D20036 50 nM, 10 min | LPR 10 min |
| Slide 8 | D19112: DAB 0.28 mM, $H_2O_2$ 1.5 mM, 2 min | D20036 50 nM, 10 min | LPR 10 min |
| Slide 9 | D19112: DAB 0.28 mM, $H_2O_2$ 1.5 mM, 1 min | D20036 50 nM, 10 min | LPR 10 min |
| Slide 10 | D19112: DAB 0 mM, $H_2O_2$ 1.5 mM, 10 min | D20036 50 nM, 10 min | LPR 10 min |
| Slide 11 | D19112: DAB 0.07 mM, $H_2O_2$ 1.5 mM, 10 min | D20036 50 nM, 10 min | LPR 10 min |
| Slide 12 | D19112: DAB 0.14 mM, $H_2O_2$ 1.5 mM, 10 min | D20036 50 nM, 10 min | LPR 10 min |
| Slide 13 | D19112: DAB 0.56 mM, $H_2O_2$ 1.5 mM, 10 min | D20036 50 nM, 10 min | LPR 10 min |
| Slide 14 | D19112: DAB 1.12 mM, $H_2O_2$ 1.5 mM, 10 min | D20036 50 nM, 10 min | LPR 10 min |
| Slide 15 | D19112: DAB 2.09 mM, $H_2O_2$ 1.5 mM, 10 min | D20036 50 nM, 10 min | LPR 10 min |
| Slide 16 | D19112: DAB 0.28 mM, $H_2O_2$ 0.6 mM, 10 min | D20036 50 nM, 10 min | LPR 10 min |
| Slide 17 | D19112: DAB 0.28 mM, $H_2O_2$ 5.9 mM, 10 min | D20036 50 nM, 10 min | LPR 10 min |
| Slide 18 | D19112: DAB 0.28 mM, $H_2O_2$ 14.7 mM, 10 min | D20036 50 nM, 10 min | LPR 10 min |
| Slide 19 | D19112: DAB 0.28 mM, $H_2O_2$ 58.8 mM, 10 min | D20036 50 nM, 10 min | LPR 10 min |
| Slide 20 | D20068: DAB 0.28 mM, $H_2O_2$ 1.5 mM, 10 min | D20036 50 nM, 10 min | LPR 10 min |
| Slide 21 | D20086: DAB 0.28 mM, $H_2O_2$ 1.5 mM, 10 min | D20036 50 nM, 10 min | LPR 10 min |
| Slide 22 | D20118: DAB 0.28 mM, $H_2O_2$ 1.5 mM, 10 min | D20036 50 nM, 10 min | LPR 10 min |
| Slide 23 | D20120: DAB 0.28 mM, $H_2O_2$ 1.5 mM, 10 min | D20036 50 nM, 10 min | LPR 10 min |
| Slide 24 | D19112: DAB 0.28 mM, $H_2O_2$ 1.5 mM, 10 min | D20036 50 nM, 10 min | LPR 10 min |

Experiment 2
All slides were treated as in example 1, then subjected to deposition, reporter binding agent and chromogen stain as detailed in table 2.

TABLE 2

| | Deposition media (step b) | Detection (step c) Reporter binding agent (step c') | Stain (step c") |
|---|---|---|---|
| Slide 1 | D19112: 10 µM, DAB 0.14 mM, $H_2O_2$ 1.5 mM, 10 min | D20036 50 nM, 10 min | LPR 10 min |
| Slide 2 | D19112: 20 µM, DAB 0.14 mM, $H_2O_2$ 1.5 mM, 10 min | D20036 50 nM, 10 min | LPR 10 min |
| Slide 3 | D19112: 5 µM, DAB 0.14 mM, $H_2O_2$ 1.5 mM, 10 min | D20036 50 nM, 10 min | LPR 10 min |
| Slide 4 | D19112: 3 µM, DAB 0.14 mM, $H_2O_2$ 1.5 mM, 10 min | D20036 50 nM, 10 min | LPR 10 min |
| Slide 5 | D19112: 2 µM, DAB 0.14 mM, $H_2O_2$ 1.5 mM, 10 min | D20036 50 nM, 10 min | LPR 10 min |
| Slide 6 | D19112: 1 µM, DAB 0.14 mM, $H_2O_2$ 1.5 mM, 10 min | D20036 50 nM, 10 min | LPR 10 min |

TABLE 2-continued

| | Deposition media (step b) | Detection (step c) | |
|---|---|---|---|
| | | Reporter binding agent (step c') | Stain (step c") |
| Slide 7 | D19112: 10 μM, DAB 0.14 mM, $H_2O_2$ 1.5 mM, 10 min | D20036 100 nM, 10 min | LPR 10 min |
| Slide 8 | D19112: 10 μM, DAB 0.14 mM, $H_2O_2$ 1.5 mM, 10 min | D20036 25 nM, 10 min | LPR 10 min |
| Slide 9 | D19112: 10 μM, DAB 0.14 mM, $H_2O_2$ 1.5 mM, 10 min | D20036 12.5 nM, 10 min | LPR 10 min |
| Slide 10 | D19112: 10 μM, DAB 0.14 mM, $H_2O_2$ 1.5 mM, 10 min | D20036 6 nM, 10 min | LPR 10 min |
| Slide 11 | D19112: 10 μM, DAB 0.14 mM, $H_2O_2$ 1.5 mM, 10 min | D20036 3 nM, 10 min | LPR 10 min |
| Slide 12 | D19112: 10 μM, DAB 0.14 mM, $H_2O_2$ 1.5 mM, 10 min | D20036 50 nM, 10 min | LPR 10 min |

Experiment 3

All slides were treated as in example 1, then subjected to deposition, reporter binding agent and chromogen stain as detailed in table 3.

TABLE 3

| | Deposition media (step b) D 19112: all slides 5 μM | Detection (step c) | |
|---|---|---|---|
| | | Reporter binding agent (step c') | Stain (step c") |
| Slide 1 | D19112: DAB 0.14 mM, $H_2O_2$ 1.5 mM, 10 min | D20036 50 nM, 10 min | LPR 10 min |
| Slide 2 | D19112: DAB 0.14 mM, $H_2O_2$ 1.5 mM, 10 min | D20036 50 nM, 10 min | LPR 5 min |
| Slide 3 | D19112: DAB 0.14 mM, $H_2O_2$ 1.5 mM, 10 min | D20036 50 nM, 10 min | LPR 3 min |
| Slide 4 | D19112: DAB 0.14 mM, $H_2O_2$ 1.5 mM, 10 min | D20036 50 nM, 10 min | LPR 2 min |
| Slide 5 | D19112: DAB 0.14 mM, $H_2O_2$ 1.5 mM, 10 min | D20036 50 nM, 10 min | LPR 1 min |
| Slide 6 | D19112: DAB 0.14 mM, $H_2O_2$ 1.5 mM, 20 min | D20036 50 nM, 10 min | LPR 10 min |
| Slide 7 | D19112: DAB 0.14 mM, $H_2O_2$ 1.5 mM, 15 min | D20036 50 nM, 10 min | LPR 10 min |
| Slide 8 | D19112: DAB 0.14 mM, $H_2O_2$ 1.5 mM, 5 min | D20036 50 nM, 10 min | LPR 10 min |
| Slide 9 | D19112: DAB 0.14 mM, $H_2O_2$ 1.5 mM, 3 min | D20036 50 nM, 10 min | LPR 10 min |
| Slide 10 | D19112: DAB 0.14 mM, $H_2O_2$ 1.5 mM, 2 min | D20036 50 nM, 10 min | LPR 10 min |
| Slide 11 | D19112: DAB 0.14 mM, $H_2O_2$ 1.5 mM, 1 min | D20036 50 nM, 10 min | LPR 10 min |
| Slide 12 | D19112: DAB 0 mM, $H_2O_2$ 1.5 mM, 10 min | D20036 50 nM, 10 min | LPR 10 min |
| Slide 13 | D19112: DAB 0.07 mM, $H_2O_2$ 1.5 mM, 10 min | D20036 50 nM, 10 min | LPR 10 min |
| Slide 14 | D19112: DAB 0.28 mM, $H_2O_2$ 1.5 mM, 10 min | D20036 50 nM, 10 min | LPR 10 min |
| Slide 15 | D19112: DAB 0.56 mM, $H_2O_2$ 1.5 mM, 10 min | D20036 50 nM, 10 min | LPR 10 min |
| Slide 16 | D19112: DAB 1.12 mM, $H_2O_2$ 1.5 mM, 10 min | D20036 50 nM, 10 min | LPR 10 min |
| Slide 17 | D19112: DAB 2.09 mM, $H_2O_2$ 1.5 mM, 10 min | D20036 50 nM, 10 min | LPR 10 min |
| Slide 18 | D19112: DAB 0.14 mM, $H_2O_2$ 0 mM, 10 min | D20036 50 nM, 10 min | LPR 10 min |
| Slide 19 | D19112: DAB 0.14 mM, $H_2O_2$ 0.6 mM, 10 min | D20036 50 nM, 10 min | LPR 10 min |
| Slide 20 | D19112,: DAB 0.14 mM, $H_2O_2$ 5.9 mM, 10 min | D20036 50 nM, 10 min | LPR 10 min |
| Slide 21 | D19112,: DAB 0.14 mM, $H_2O_2$ 14.7 mM, 10 min | D20036 50 nM, 10 min | LPR 10 min |
| Slide 22 | D19112,: DAB 0.14 mM, $H_2O_2$ 58.8 mM, 10 min | D20036 50 nM, 10 min | LPR 10 min |

Results of Experiments 1-3.

Experiment 1 (Table 1, slides 1-5) and 3 (Table 3, slides 1-5) demonstrate that, in otherwise the same conditions (same binding agents in the same concentration, same reporter, same concentrations of DAB, reporter and $H_2O_2$, same incubation time), the dot size depends on deposition time of the chromogen on the final, detection, stage of the procedure, i.e. deposition time of Liquid Permanent Red (LPR) chromogen staining the reporter deposits. The largest dots are produced with 10 min precipitation of LPR, the size of the dots were decreasing with decreasing the precipitation time. However, even 1 min of the precipitation (slides 5) was enough to observe small but distinguished dots.

Experiment 1 (Table 1: slide 1 and slides 6-9) and experiment 3 (Table 3: slide 1 and slides 6-11) demonstrate that the dot size varies depending on the duration of incubation of a sample containing complexes of the target, i.e. Her2 receptor, with the HRP-labeled binding agent, i.e. D20052, fraction 8, in the media containing a reporter, DAB and $H_2O_2$, thus, depending on the time used for depositing the reporter from the media (when the other conditions are fixed, i.e. same reporter, same binding agents, same detection agents, same concentrations of DAB, $H_2O_2$ reporter, binding agent and detection stain, same duration of the deposition of the stain on the detection step). The largest dots were produced with 10 min precipitation. Further increasing time to 15 or 20 min did not result in larger dots, but in a significant increase in background staining. The dot size decreases with decreasing the precipitation time from 10 min to 1 min.

Experiment 1 (Table 1: slides 1 and 16-19) and 3 (Table 3; slides 1 and 18-22) demonstrate that the dot size may be varied by varying concentration of $H_2O_2$ in the deposition media containing DAB and reporter. The largest dots are produced when the concentration of hydrogen peroxide is 1.5 mM. In the absence of hydrogen peroxide, no dots are produced Table 3: slide 18). Both lower and higher concentrations of hydrogen peroxide reduce the size of the dots. At 58.8 mM the dots become almost indistinguishable.

Dot size varies as function of DAB concentration in the deposition media containing DAB and reporter as shown in Experiment 1 (Table 1: slides 1 and 10-15) and Experiment 3 (Table 3: slides 1 and 12-17). The largest dots are produced when the DAB present in the concentration range from 0.14 mM to 0.28 mM. In the absence of DAB no dots are produced. Reducing DAB concentration to 0.07 mM leads to the dots which are smaller and more diffuse than at 0.14 mM, likewise does the higher concentrations of DAB: at 2.09 mM DAB very small dots are produced.

The number of ferulic acid residues (3 vs 4 residues) in a reporter molecule has a minor influence on the dot size: dot size varied only marginally with different reporters. As showed Experiment 1, (Table 1: slides 20-24). D20068 reporter with 4 ferulic acid moieties produced slightly larger dots than the reporters having 3 moieties but at the same time the level of background staining was also increased. The best signal to noise was obtained with D19112 which comprises 3 moieties ferulic acid.

Dot size varies with concentration of the reporter, Experiment 2 (Table 2: slides 1-6) demonstrates that in the range from 5 microM to 20 microM reporter D19112 (in otherwise the same conditions) forms deposits that only marginally differ in size: 10 and 20 microM produce slightly larger dots than 5 microM, but the background staining increases as well. Below 5 microM, the dot size significantly reduces; however even at 1 microM small dots are still well visible.

The concentration of the binding agent capable of binding to the deposited reporter, i.e., D20036, influenced the dot size only slightly (as showed in Experiment 2 Table 2: slides 7-12). The largest dots were obtained (in otherwise the same conditions) when the concentration of anti-Flu-AP conjugated antibody (D20036), was 50 nM. 100 nM and concentrations below 50 nM did not produce dots as large size. At very low concentrations (6 or 3 nM) very small, but still distinguishable dots were produced.

The dots which size regulated, in particular reduced, by reporter concentration, concentration of the reporter binding agent and precipitation time of the detection stain (i.e. LPR stain on the detection step) showed a characteristic intensity gradient, being most intense stained at the center and diffused on periphery, giving these dots overall a diffuse look The dots that size was regulated, in particular reduced, by high DAB concentration, high hydrogen peroxide concentration or reduced time in the precipitation step has a crisp look, with the uniform intensity and sharp boarders.

Example 2

Dot Size as Function of Structure of the Second Substrate of an Enzyme with Oxidoreductase Activity: Testing Different Conjugate Molecules All slides were pretreated as in example 1. And then subjected to the following protocol: Incubation with anti cytokeratin Dako M3515 2 nM for 3 min, washed with wash buffer (Dako S3306) then incubation with GaM/HRP (D20168 frac. 9+10) in concentration 100 picoM for 3 min. Then the slides were subjected to a deposition step with different reporters but under otherwise identical conditions. (50 mM imidazole HCl pH 7.5, 0.1% Nonidet P40, 0.1%, benzalkonium chloride, DAB 0.14 mM, $H_2O_2$ 1.5 mM) for 10 min. This was followed by a reporter binding agent step D20036, 20 nM for 10 min) and a staining step with LPR chromogen, 10 min. Washing steps were used between each step. The following reporters were tested under these conditions:

D19112, D18044, D181126, D18146, D20171, D21016, 0328-014 (all 5 microM) The dextran reporter conjugate D21008 was tested in 50 nM and 250 nM. In combination with the reporters tested in experiment 1 this leads to the following conclusion:

The nature of the reporter critically affects how efficiently reporter deposition takes place. Surprisingly relative small reporters such as D20171 (1 fluorescein, 4 ferulic acids), and D19112 (1 fluorescein, 3 ferulic acids) proved more efficient than larger molecules such as D18126 (3 fluoresceins, 6 ferulic acids) or the large dextran conjugate D21008 (83 fluoresceins and 111 ferulic acids). In case of the dextran conjugate this may be ascribed to poor penetration into the sample. The fact that tissue type and fixation affected dot size when using this large conjugate supports this notion.

In case of D18126, which is a relatively (to antibody-enzyme conjugates) small molecule lack of penetration does not seem an adequate explanation for poor performance. A number of control experiments were run to better elucidate the deposition mechanism: In the absence of DAB in the deposition media, no dots were formed. If however a deposition reaction was run with DAB alone, then followed by a deposition reaction with D20171 without DAB addition very small dots resulted. This finding strongly suggest that part of the mechanism is an HRP driven coating of the sample with DAB polymers, that subsequently serve as anchors for reporters. Another experiment was carried out with a 10 minutes washing step in boiling CHES buffer following the deposition step. This was performed to reduce background, however this very stringent wash also led to a significant drop in dot size.

This demonstrates that most deposited reporters are not covalently cross linked to the sample but rather precipitated as insoluble deposits, where as other reporters can be considered truly immobilized. This finding indicates two further mechanisms; a solution phase reactions between DAB and reporters leads to adducts of reduced solubility that precipitate in combination with true covalent cross linking between reporters and sample. It seems likely that the large reporters are less likely to precipitate, as it will require several reactions with DAB to render these insoluble, whereas the smaller reporters are rendered insoluble by a single or a few reaction with DAB.

The reporters with reduced linker length, D 20086 (L30) and D20118 (L60), gave almost as big dots as did D19112 (L150), though these shortened reporters also produced slightly more background. This slightly decreased signal (dot size) to noise is likely do to decreased solubility resulting in more stickiness and decreased accessibility of the fluorescein haptens. Thus long stretches of linker enhances reporter performance.

A critically important factor is the nature of the reactive groups in the reporter. The fact that reporters can be deposited in the absence of DAB, if following a DAB coating step, demonstrates that HRP catalyzed radical formation of reporters plays a role. Likewise does the fact that the reporter D 18126 with ferulic acids results in bigger dots than the similar reporter D 18146 with 4-amino cinnamic acid, and that the likewise similar D18044 with tyrosine residues does not produce dots at all, show the importance of the reactive groups in the reporter. Reporters D21020 and 0328-014 that are similar in structure to D19112 but with respectively caffeic acid and sinapinic acid in place of ferulic acid give either somewhat small dots (D21020) or slightly larger (0328-014) than D19112. Ferulic, caffeic acid and sinapinic acid are all very good HRP substrates and HRP radical activation of reporters is a likely main contributor to linker deposition.

In conclusion, many factors contribute to make efficient reporters: Relative small size yet extended stretches of water soluble linker. A balanced overall water solubility that is significantly reduced upon reaction with DAB. The presence of two or more phenols or aromatic amines that are good HRP substrates make good reporters. Preferably are 3-4 ferulic acid derivatives, most preferably are 3 sinnapinic acid derivatives; i.e. the reporter 0328-014 performed best of all tested.

The table below summaries results of several SMD staining using exemplary conjugate molecules having different structures (different Y-head, different molecular distance between Y-head and Z-tail, same Z-tail (one Flu)):

| Conjugate | Molecular distance between Y-head and Z-tail | Y-Head | Relative Dot size* |
|---|---|---|---|
| D19112 | L150 | Fer-Lys(Fer)-Lys(fer)- | 3 |
| D20118 | L60 | Fer-Lys(Fer)-Lys(fer)- | 2 |
| D20086 | L30 | Fer-Lys(Fer)-Lys(fer)- | 2 |
| D19185 | L150 | Fer-Lys(Fer)-Lys(fer)-Lys(Fer) | 3 |
| D21047 | L150 | Sin-Lys(Sin)-Lys(Sin)- | 4 |
| D21028 | L150 | Sin-Lys(Sin)-Lys(Sin)-Lys(Sin) | 3 |
| D21150 | L150 | Sin-Lys(Sin)-Tyr- | 3 |

*The relative dots size approximately corresponds to maximum dot diameter in microns under optimal conditions: High pH target retrieval of tissue, 10 microM reporter, 1.6 mM Hydrogen peroxide and 0.28 mM DAB in precipitation reaction for 10 min at room temperature, reporter recognition for 10 min with 20 nM antiFITC-AP, followed by 10 min LPR. The relative scores have been judged from several experiments under different conditions (target retrieval and reporter concentration) on different tissue samples and control cell lines and are qualitative.

Example 3

Dot Size as Function of the Amount of HRP-Labeled Binding Agent and Number of Moieties of HRP Per Binding Agent 10 slides were deparaffinzed and target retrieved in the Dako target retrieval media (Dako S2763) by 10 min boiling in microwave oven. 100 nM anti-cytokeratin mouse antibody (Dako M3515) was premixed with different number of molar equivalents of anti-mouse secondary antibody-HRP conjugates, and after 30 min the mixtures were diluted to final concentrations as described in table 4:

TABLE 4

| Slide number | Secondary-HRP conjugate | Equivalents secondary-HRP | Final antibody concentration |
|---|---|---|---|
| 1 | D19150 (1 HRP) | 0.5 | 20 pM |
| 2 | D19150 (1 HRP) | 1 | 20 pM |
| 3 | D19150 (1 HRP) | 2 | 20 pM |
| 4 | D19150 (1 HRP) | 4 | 20 pM |
| 5 | D19150 (1 HRP) | 8 | 20 pM |
| 6 | D19150 (1 HRP) | 16 | 20 pM |
| 7 | D20052 fraction 8 (10 HRP) | 1 | 200 pM |
| 8 | D20052 fraction 8 (10 HRP) | 2 | 200 pM |
| 9 | D20052 fraction 8 (10 HRP) | 3 | 200 pM |
| 10 | D20052 fraction 8 (10 HRP) | 4 | 200 pM |

All the slides were subjected to immunostaining according to the same protocol:
1. Primary antibody/secondary antibody-HRP mixture; 3 min incubation
2. 50 mM imidazole HCl pH 7.5, 0.1% Nonidet P40, 0.1% benzalkonium chloride, 0.005% hydrogen peroxide, 140 microM DAB, 5 microM D19112; 8 min incubation
3. antiFITC-HRP, D20154, 100 nM; 5 min incubation
4. DAB chromogen solution; Dako K3468; 2 min incubation
5. Haematoxilin counterstain; 1 min incubation In steps 1 and 3 0.1% 4-aminoantipurine, 0.2% Procline-2% BSA, 0.2% Casein, 2% PEG, 0.1% Tween20, 0.1 M NaCL, 10 mM HEPES, pH 7.2. (ABCPT-buffer) was used as diluents.

All slides showed a cytokeratin specific dotted staining looked like brown to black dots. The number of dots, and their size increased through slides 1-3. On slides 3-5 the number of dots remained essentially invariable, but the size of the dots was increased from slide 3 to 5. Slide 6 had fewer dots but generally of a larger size. The biggest dots were observed on slides 7-10, though the size only marginally increased with number of equivalents secondary HRP conjugates in the premix. The number of dots decreased with increasing number of secondary HRP conjugates, supporting that premixing with an excess of secondary conjugates leads to larger assemblies and slower target binding.

Example 4

Dot Size as Function of the Number of HRP Per Binding Agent

Fractions of D20052 (7,8,9,11,13,15,17,19,21) were diluted in ABCPT buffer to a total HRP concentration of 100 pM, and dot size was assessed for each fraction. A pool of the fractions was also analysed, likewise was D19150 (F(ab)1-HRP1) included in the test.

The following protocol was used:
1. antiCytokeratin (Dako 3515) 1 nM; 1 min
2. Fractions of D20052 (100 pM HRP)/D19150; 1 min
3. 50 mM imidazole HCl pH 7.5, 0.1% Nonidet P40, 0.1% benzalkonium chloride, 0.005% hydrogen peroxide, 140 microM DAB, 10 microM D19112; 8 min.
4. antiFITC-HRP, D19154 100 nM; 5 min
5. DAB chromogen solution; 50 mM imidazole HCl pH 7.5, 0.1% Nonidet P40, 0.1% benzalkonium chloride, 0.2% hydrogen peroxide, 5.6 mM DAB; 1 min
6. Haematoxilin counterstain; 1 min Results: Fractions 7 and 8 produced significantly fewer dots than the following fractions. These were also the largest dots, however fractions 9-12 produced significantly more dots of almost as large size. Fractions 13-22 produced dots of decreasing size. D19150 with a single HRP enzyme per molecule, produced a lot more dots than any of the fractions of D20052, the dots were also much smaller. Each fraction produced dots of relatively uniform size, while the pool of all the fractions produced dots of highly variable size.

Example 5

Test of fractions 1-4 of D20075, a larger dex150 conjugate, was performed as described in experiment 5 above. The dots produced resemble the dots of fractions 7 and 8 of D20052; i.e. few dots were produced, though they were not significantly larger than those produced by fractions 9-12 of D12052.

Conclusions

From experiments 4-6 we conclude that there is a strong correlation between the number of HRP per binding agent molecule and the size of dots produced under similar circumstances. Increasing number of HRP in each molecule of a binding agent, independently, whether obtained through premixing or conjugation, leads to larger dots. This effect, however, seems to level off around 10 HRP/molecule: larger dextran conjugates do not produce larger. The number of dots shows a reverse correlation: larger molecules, especially very large ones, produce fewer dots. This might be result of a steric hindrance originating from the mass of enzymes bound to each antibody molecule, and slower diffusion rate of large molecules in general. Experiment 4, slides 1-3, however, also indicates that binding agent molecules comprising a single enzyme moiety produce fewer and downwards variable dots than those with a few enzymes per molecule, presumably, because some single enzyme molecules fail to produce visible dots because of rapid enzyme inhibition. Experiments 4-6 all utilize very short chromogen precipitation time on the stage of detection of the reporter deposits, leading to dots appear to look smaller than they could have been seen. Experiments 1-3 (above) show that the final chromogen precipitation time during detection of the reporter deposits may affect the visual dot size. To minimize the effect, this time has been kept short to highlight the influence of the enzyme amount.

Example 6

Fluorescent Double Stain

4 Slides were pretreated as described in example 1.
D20168 frak. 9-10 was premixed with an equimolar amount of anti cytokeratin (Dako M3515) in ABCPT binding agent buffer, both reagents in 100 nM concentration for 5 min. Following this premixing step, a 20 pM solution in ABCPT binding agent buffer was prepared, "20 pM mix".

Slide 1 was treated with 20 pM mix for 1 min, washed (Dako wash buffer, S3006) then treated with 20 microM D20171 and 0.28 mM DAB in deposition media for 1 min and washed.

Slide 2 was treated with 20 pM mix for 1 min, washed (Dako wash buffer, S3006) then treated with 5 microM D19048 and 0.28 mM DAB in deposition media for 1 min and washed Slide 3 was treated with 20 pM mix for 1 min, washed (Dako wash buffer, S3006) then treated with 20 microM D20171+5 microM D19048 and 0.28 mM DAB in deposition media for 1 min and washed.

Slide 4 was treated with 20 pM mix for 1 min, washed (Dako wash buffer, S3006) then treated with 20 microM D20171 and 0.28 mM DAB in deposition media for 1 min and washed. The slide was treated with 3 M hydrogen peroxide for 1 min, washed, then again treated with 20 pM mix for 1 min, washed (Dako wash buffer, S3006) then treated with 5 microM D19048 and 0.28 mM DAB in deposition media for 1 min. All slides were finally washed with water, dehydrated in ethanol and mounted with fluorescence mounting media (Dako K5331).

Results. Slide 1 gave fluorescent round green dots in cytokeratin positive tissue. Slide 2 gave fluorescent round red dots in cytokeratin positive tissue. Slide 3 gave fluorescent round dots that were green when viewed through a FITC filter, red when viewed in a TRITC filter and yellow in a double filter in cytokeratin positive tissue. Through the double filter, no green or red dots were observed. Slide 4 gave a mixture of fluorescent round green and red dots in cytokeratin positive tissue when viewed through a double filter. In tissue of high cytokeration expression there was some yellow overlap of green and red dots. The roundness of the dots in combination with the observed mixture of red and green dots on slide 4 leads us to conclude that each dot is produced by a single molecule: Based on slides 1 and 2 alone it could be argued that, despite the extremely low concentration of binding agent used, the observed dots are not derived from single molecules. Rather the dots might be associated with sub cellular clusters of high cytokeratin concentration each with several bound molecules of binding agent. If this was the case, slide 4 would however be expected to exhibit dots in a variety of hues, depending on how many binding agent molecules were bound to each cluster in each of the incubation steps on slide 4, or in case multiple molecules were bound to each cluster, yellow dots as on slide 3.

This example also illustrates the value of simultaneous deposition of two different reporters.

Example 7

Chromogenic Double Stain of Two Different Co-Localized Targets

Slides were pretreated as in example 1. For this experiment a tissue micro array of mamma tissue with different HER2 status (assessed to be from 0+ to 3+ by Dakos Herceptest) were used as test material. An experimental monoclonal mouse antibody directed at the C-terminal of the HER2 protein was used, "clone 6C2", The following protocol was used:
1. 10 pM anti cytokeratin premixed with D20168 frak. 9-10 as in example 7, in
   ABCPT binding agent buffer; 3 min.
2. 5 microM D19059 in deposition buffer with 0.45 microM DAB for; 8 min.
3. 3 M hydrogen peroxide, 3 min 4. 15 pM "clone 6C" premixed with D20168 frak. 9-10 as in example 7, in ABCPT binding agent buffer (a), 3 min.
5. 5 microM D19112 in deposition buffer (b) with 0.45 microM DAB for; 8 min.
6. 25 nM D20036 (antiFITC-AP)+25 nM D19053 (anti-FITC-AP) in ABCPT buffer for 10 min.
7. Liquid Permanent Red, Dako K0640, 6 min
8. Blue chromogen 400 mg/L in 50 mM imidazole HCl pH 7.5, 0.1% Nonidet P40, 0.1% benzalkonium chloride, 5.8 mM hydrogen peroxide; 6 min Results: This protocol produced red (Her2) and blue (cytokeratin) dots on mamma tissues, and despite the double stain only a very faint blue background. Photo micrographs were acquired of the different tissues, and images were printed using a standard color printer. This allowed manual counting of several hundred dots per picture. Tissue that had been assessed HER2 negative (0+) by Herceptest showed 9 times as many blue dots as red dots. Tissue that had been assessed strongly HER2 positive (3+) showed more than three times as many red dots as blue dots; i.e. the ration of red to blue dots was approx. 30 times higher for the 3+ tissue than the 0+ tissue. Tissue assessed as 1+ and 2+ showed intermediate ratios.

Example 8

Staining of Low Abundance mRNA Targets

Slides with FFPE sections of blocks with different tissue samples were de paraffinized by emersion in xylene (2×5 min) followed by 96% ethanol (2×2 min) and 70% ethanol (2×2 min).

The slides were washed with de ionized water and transferred to target retrieval solution, 20 mM MES (2-(N-Morpholino)ethanesuphonic acid) pH 6.55, and boiled in a microwave oven for 5 min. Following 15 min cooling the slides were rinsed twice with wash buffer (Dako S3006), subjected to pepsin digestion for 2 min at 37 C, then rinsed twice with wash buffer.

The slides were dehydrated, 70% ethanol 1 min, 85% ethanol 1 min, 96% ethanol 1 min. FITC labeled anti Kappa mRNA probes (Dako Y5202, Ready To Use) were applied to the slides, and they were cover slipped. The slides were denaturized at 82 C for 5 minutes, followed by 1 hour hybridization at 45 C. The slides were stringent washed for 10 min at 65 C in stringent wash buffer (from Dako kit K5201).

The slides were then subjected to the following SMD protocol:
Peroxidase block, 2 min with Dako S2023
Wash 3 min
antiFITC-HRP, AMM353.022, 20 min in incubation media 1. Five different concentrations were used (10, 20, 40, 80, 160 picoM)
Wash 3 min
Reporter D21047, 5 microM, DAB 0.14 mM, hydrogen peroxide 1.5 mM in incubation media 2 for 10 min.
Wash 3 min
antiFITC-Alkaline phosphatase (D20036) 20 nM for 10 min in incubation media 1.
Wash 3 min
Liquid Permanent Red, Dako K0640, 10 min
Wash 2 min
Counterstain with haematoxilin (Dako S3309 diluted 6× with water), 2 min.
Wash with deionized water
Mounting with Dako Fairmount, S3025.

Results: All slides showed distinct red dots of around 3 micron diameter. The dots were present in all types of tissue, and the number of dots increased with increasing concentration of antiFITC-HRP. In high concentration (80 and 160 picoM) Kappa positive cells could be clearly identified in tonsil and colon tissues as each being stained with tens of coalescent Dots. Multiple coalescent Dots were not observed in other tissues, nor in Kappa negative cells in tonsil or colon. This illustrates how this technique with advantage also can be used in a qualitative manner in case of low abundance target such as mRNA.

Example 9

Ferulic Acid as the First Substrate

Slides with FFPE sections of blocks of control cell lines were de paraffinized by emersion in xylene (2×5 min) followed by 96% ethanol (2×2 min) and 70% ethanol (2×2 min).

The slides were washed with de ionized water and transferred to target retrieval solution, Dako pH 9, S2367, and boiled in a microwave oven for 10 min.

The slides were then subjected to the following SMD protocol:
Peroxidase block, 5 min with Dako S2023
Wash 2 min
Anti Cytokeratin Dako M3515 dilluted 1:50 in incubation media 1 for 5 min.
Wash 2 min
1 picoM Goat-anti-Mouse, L348.121 in incubation media 1 for 5 min.
Wash 3 min
Reporter D21047, 20 microM, hydrogen peroxide 1.5 mM in incubation media 2 for 10 min with varying concentrations of Ferulic acid (52 mM, 16 mM, 5.2 mM, 1.6 mM, 0.52 mM) or 0.14 mM DAB
Wash 9 min
antiFITC-Alkaline phosphatase (D20036) 20 nM for 10 min in incubation media 1.
Wash 9 min
Liquid Permanent Red, Dako K0640, 10 min
Wash 2 min
Wash with deionized water
Mounting with Dako Fairmount, S3025.
Results.

The performed To assure very efficient reporter deposition the protocol was optimized by using a binding agent with many (20) HRP enzymes/molecule, conditions of high pH target retrieval (to assure a good tissue accessibility) and an efficient reporter, D21047, has been used in a relatively high amount. Under these conditions control slides with 0.14 mM DAB produced dots up to 4 microns in diameter. In case of ferulic acid (as cross-linker), the concentration 1.6 mM was optimal: dots up to two microns have been produced. Lower and higher concentrations of ferulic acid resulted in smaller dots, at the highest concentration, 52 mM, no dots were observed. No dots were observed in slides incubated without ferulic acid or DAB.

Without bound to the theory, it suggested that ferulic acid, like DAB, has a capacity of cross-link molecules of the second substrate, albeit it is less efficient then DAB and has a different concentration optimum.

Production of dots up to 4 microns in the presence of cross-linker, and no dots without it (under otherwise the same conditions of incubation) suggests that direct enzymatic reporter activation plays only a minor role in the deposition reactions. Both DAB and ferulic acid can undergo homopolymerization in the presence of HRP and peroxides. The presence of large dots (4 microns) shows that reporters can be deposited up to several microns apart of the site with HRP activity and suggest that a possible mechanism of the deposition is that some cross-linker molecules react with HRP and produce the corresponding radicals, these trigger radical chain reactions with cross-linker molecules and with reporter molecules and produce oligomeric radicals that are sufficiently stabilized by extensive delocalization. This allows the radicals to diffuse from the enzyme and stay in the deposition medium for up to ten minutes (prior to the deposition is taken place). The concentration optima observed for both DAB and Ferulic acid supports such a mechanism. At high cross-linker concentrations cross-linkers/reporter oligomers may rapidly become insoluble and deposited close to the site of enzyme activity. At too low cross linker concentrations, oligomerisation is insufficient to produce large insoluble oligomers.

Example 10

Quantification of Her2 in a Sample

Test Material

As a test material serial sections of pellets of formalin fixed paraffin embedded cell lines sk45 (+0 line), df45 (+1 line), df23 (+3 line) expressing Her2 were used Pellets of the cell lines were embedded in a single block of paraffin to provide sections where the every cell lines present.

Pretreatment of Test Material:

Slides with FFPE sections of blocks containing the three cell lines (further referred as "slides") were deparaffinized by emersion in xylene (2×5 min) followed by 96% ethanol (2×2 min) and 70% ethanol (2×2 min). Then, the slides were washed with deionized water and transferred to Target retrieval solution, either the high pH solution (Dako S2375), diluted 10×(examples 1 and 2 with anti cytokeration) or low pH solution (Dako S1700) (see examples 10.3-10.8 below). The slides were then heated to boiling in a microwave oven (approx 5 min) and gently boiled for 10 min. Afterwards the slides were allowed to cool for min 20 min and then were transferred to a wash buffer (Dako S3006) diluted 10×.

Primary Antibodies:

Anti-Her2 antibody was a monoclonal rabbit antibody (Dako clone 25-11-3). Dilutions were made based on calculated total protein concentration in a concentrated solution and the molecular weight of the antibody of (150 kDa/mol).

Conjugates: Binding Agents and Reporters
  L348.111, fractions 10-11
  D21100, fractions 9-10
  AMM 353-022 fractions 8-11
  D21047
  (for details see description above):

Incubation Media
  solution (a): 0.1% 4-aminoantipurine, 0.2% Procline 2% BSA, 0.2% Casein, 2% PEG, 0.1% Tween20, 0.1 M NaCL, 10 mM HEPES, pH 7.2. (ABCPT-buffer)
  solution (b): 50 mM imidazole HCl pH 7.5, 0.1% Nonidet P40, 0.1%, benzalkonium chloride, 0.005% (1.5 mM) hydrogen peroxide, Instruments.

Dako Autostainer Classic. This instrument is a totally open and freely programmable automated IHC instrument where reagents and incubation times can be used and set at will. The instrument performs four basic actions
  1. Aspirate reagent.
  2. Blow wash buffer off horizontally placed slide.
  3. Dispense reagent onto slide. (Known as sip and spit.)
  4. Wash a slide by flushing it with wash buffer.

A typical program for a single slide is described below in protocol 1. For all SMD experiments the initial peroxidase block and the dot forming steps were kept invariable:

Protocol
  Peroxidase Block, 5 min in Dako S2023
  Wash
(a) Formation of Target Sites:
  Primary antibody, 100 pM in solution (a)
  Wash
  HRP-Labeled secondary antibody, as described in the examples.
  Wash.
(b) Formation of Reporter Deposits at Target Sites
  Incubation of samples (a) 10 minutes with 0.28 mM DAB and 5 µM reporter (D21047) in solution (b).
  Wash
c) Detection of Reporter Deposits at Single Target Sites
  Anti-FITC-AP, 10 min, 20 nM D20036 in incubation media 1
  Wash
  LPR, 10 min, Dako K0640
  Wash
d) Haemotoxylin Counterstain
  Haematoxylin, 5 min
  Wash with deionized water
f) Mounting Additional washes can be introduced into the automated protocol. The automated scheduler will keep overall protocol time at a minimum, by reducing duration of washing steps to a minimum; however, duration of washing steps will depend on loading of the instrument. If a single slide is programmed to be stained, a single washing step might be reduced to 20 seconds, while a full load of 48 slides significantly increase washing time. To keep this time variation minimal, 10 slides in average were stained in each run. Accordingly, washing step duration was kept approximately 2 min per step. Multiple washes following reporter deposition and incubation of the deposits with anti-FITC-AP assures a minimal LPR background staining. Despite of massive amplification (it is estimated that each red Dots derived from a single antibody-dextran-HRP molecule bound to the target comprise in average 100 billion molecules of LPR) there can virtually no background be detected.

Figure 3:
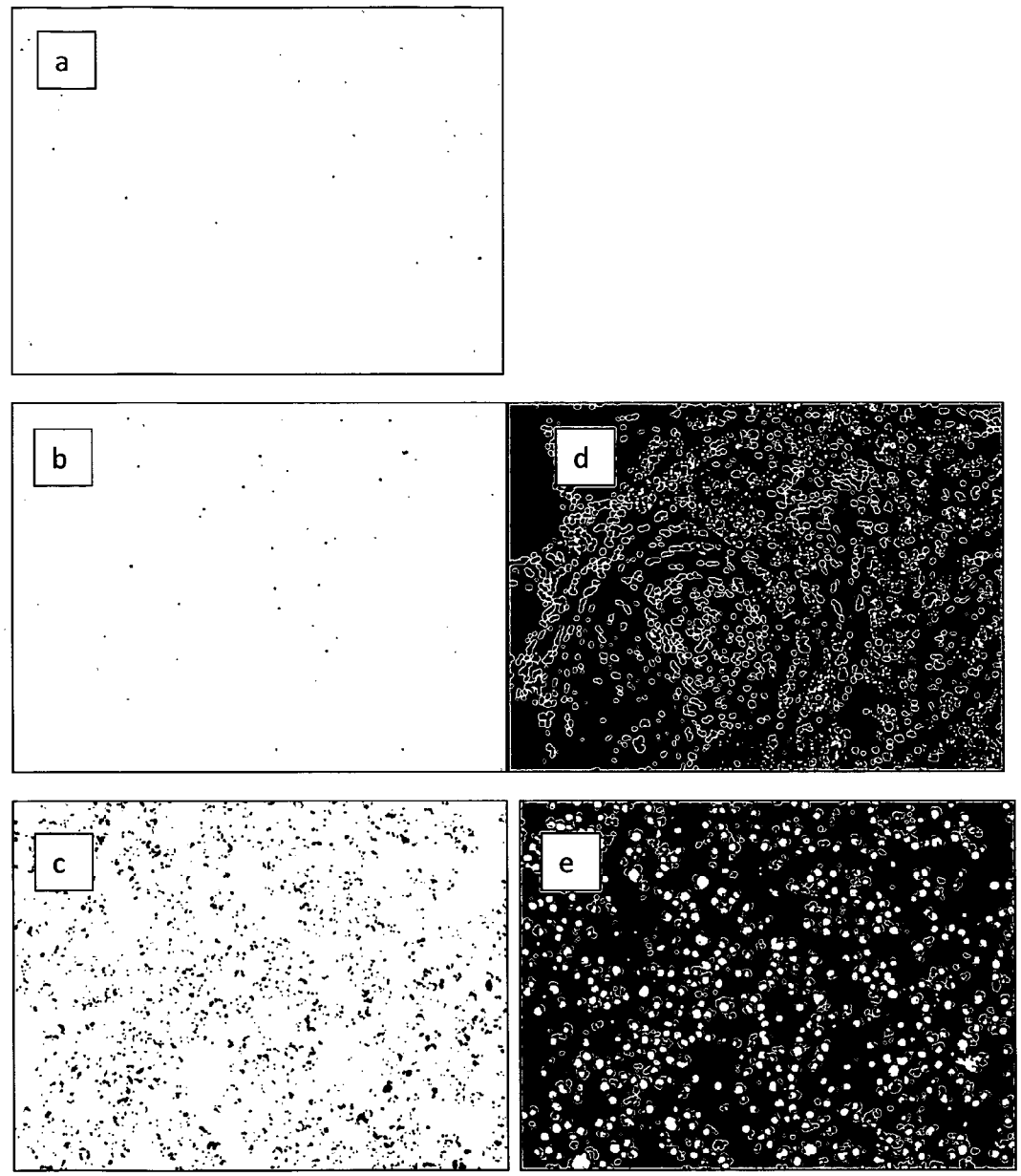
FIG. 3 shows the results of quantification of Her2 in cells according to the method the invention (see Example 10): a. Single color segmentation of 10× image of 0+ Herceptest control cell line. 21 Dots (black) per image identified; b. Single color segmentation of 10× image of 1+ Herceptest control cell line: 36 Dodts (black) per image identified; c. Single color segmentation of 10× image of 3+ Herceptest control cell line: 2567 Dots (black) per image identified; d. Two color segmentation of 10× image of Mamma carcinoma. Dots are white, nuclei black, background grey; e. Two color segmentation of 10× image of 3+ Herceptest control cell line. Dots are black, nuclei white, background grey. The same sample as c.

Dot counting was initially performed manually, by visual inspection of SMD stained slides and their images. Automated image analysis was performed using the freeware JMicrovision vs. 1.27 In an exemplary embodiment, LPR red Dots produced as described and haematoxylin stained nuclei were automatically counted. Automated counts were verified by visual inspection and manual counts. Segmentation and object abstraction could be based on hue alone in Hue, Saturation, Intensity, (HSI) color space, i.e. both intensity and saturation set to full 0-255 range. Dot hue was set to 188 (violet)-255 and 0-16 (orange), nuclear hue to 76 (green) to 163 (blue). Dot-nuclear contrast was enhanced by over exposing red (1.2), neutral green (1.0) and under exposure of blue (0.56) during image capture performed on an Olympus BX51 microscope fitted with a DP50 5.5 Mpixel camera and CellD image capture software. FIG. 3 demonstrates the processed images of the cells and the results of the dot count.

The invention claimed is:

1. A method of labeling at least one individual unit of a target in a sample, wherein said target is immobilized, comprising:

a) incubating the sample comprising a population of individual units of the target with at least one binding agent, wherein:
  (1) the at least one binding agent comprises an enzyme with peroxidase or phenoloxidase activity; and
  (2) the at least one binding agent is capable of specifically binding to an individual unit of the target, and forming at least one target site at a fractional subpopulation of the population of individual units of the target, wherein each of the at least one target sites comprises a complex of one individual unit of the target and the at least one binding agent;
b) incubating the sample obtained in step a) in an aqueous solution (i) comprising a peroxide compound at a concentration in the range from 0.001 mM to less than 5 mM, a first substrate of the enzyme, and a second substrate of the enzyme,
  wherein the first substrate is 3, 3'-diaminobenzidine or a derivative thereof at a concentration in the range from 0.05 mM to 1 mM, or another water soluble, electron rich compound which
    (1) forms a radical in the presence of the enzyme; and
    (2) cross-links molecules of the second substrate in the presence of the enzyme and the peroxide compound, thereby producing an insoluble polymer of the second substrate;
  and wherein the second substrate is a conjugate molecule comprising (i) at least two compounds that are capable of serving as substrates of the enzyme, wherein at least one of the at least two compounds is a compound of the formula (II):

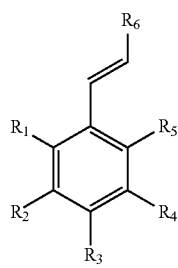

Formula II wherein
$R_1$ is —H, —O—X, —N(X)$_2$, or —S—X;
$R_2$ is —H, —O—X, —N(X)$_2$, or —S—X;
$R_3$ is —H, —OH, —NH$_2$, or —SH;
$R_4$ is —H, —O—X, —N(X)$_2$, or —S—X;
$R_5$ is —H, —O—X, —N(X)$_2$, or —S—X; and
$R_6$ is —CON(X)$_2$,
And X is H, alkyl, or aryl;
  and (ii) a detectable label, wherein the detectable label is selected from the group consisting of a fluorescent or chromogenic matter or a member of a specific binding pair;
thereby forming a labeled discrete deposit of the second substrate at the at least one target sites.

2. The method according to claim 1, wherein the at least one binding agent comprises a member of a specific binding pair.

3. The method according to claim 1, wherein the at least one target site is formed at a minority of the population of individual units of the target present in the sample.

4. The method according to claim 1, wherein the at least one target site is formed at a majority of the population of individual units of the target present in the sample.

5. The method according to claim 1, wherein the enzyme is horseradish peroxidase, soybean peroxidase, laccase, or a functional analogue of horseradish peroxidase, soybean peroxidase, or laccase.

6. The method according to claim 1, wherein the first substrate is a compound of formula (I):

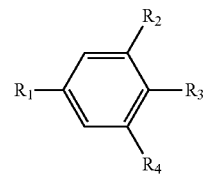

Formula I wherein
$R_1$ is an aryl or vinyl, and
$R_2$, $R_3$, and $R_4$ are each independently H, N—(X)$_2$, or O—X,
  wherein X is an alkyl, vinyl, aryl, or H,
  and wherein none of $R_2$, $R_3$, and $R_4$ are simultaneously H.

7. The method according to claim 1, wherein the first substrate is ferulic acid or a derivative thereof.

8. The method according to claim 1, wherein at least two of the compounds are defined by formula II).

9. The method according to claim 8, wherein the at least two of the compounds defined by formula II) are identical compounds.

10. The method according to claim 8, wherein the at least two of the compounds defined by formula II) are different compounds.

11. The method according to claim 1, wherein the at least one of the compounds are selected from cinnamic acid, ferulic acid, caffeic acid, amino cinnamic acid, sinappic acid, and a derviative of cinnamic acid, ferulic acid, caffeic acid, amino cinnamic acid, or sinappic acid.

12. The method according to claim 1, wherein the conjugate molecule comprises at least one tyrosine residue capable of serving as a substrate of the enzyme.

13. The method according to claim 1, wherein in the conjugate molecule each of the at least two compounds that are capable of serving as substrates of the enzyme are separated from each other by 30 or fewer consecutively connected atoms, and wherein the detectable label is separated from any of said at least two compounds by 30 or more consecutively connected atoms.

14. The method according to claim 13, wherein the 30 or more consecutively connected atoms separating in the conjugate molecule the detectable label from each of the at least two compounds comprises 2 to 10 repeats of formula (III):

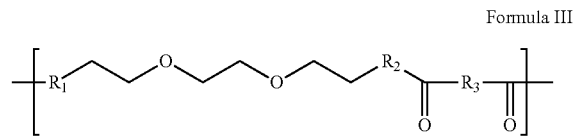

Formula III wherein $R_1$ and $R_2$ are selected from NH and O, but $R_1$ and $R_2$ are not simultaneously O, and wherein R₃ is selected from methyl, ethyl, propyl, CH₂OCH₂, and (CH₂OCH₂)₂
and wherein no more than three consecutively repeating ethyloxy groups.

15. The method according to claim 1, comprising a step (b') that precedes step (b), wherein step (b') comprises incubating the labelled sample in an aqueous solution, (ii) which is the aqueous solution (i) that does not comprise the second substrate.

16. The method according to claim 1, further comprising step (c) detecting the labeled discrete deposit of the second substrate at the at least one target sites.

17. The method according to claim 16, wherein step (c) comprises sub-steps:
   c') incubating the sample comprising the labeled discrete deposit of the second substrate with an additional binding agent capable of specifically binding to a detectable label in the deposited second substrate and forming a complex comprising one or more molecules of the deposited second substrate and one or more molecules of the additional binding agent, and
   (c") detecting the additional binding agent bound to the deposited second substrate.

18. The method according to claim 17, wherein the additional binding agent comprises an enzyme.

19. The method according to claim 17, wherein the additional binding agent comprises a detectable label selected from a chromogenic, fluorescent, luminescent or radioactive label and a member of a specific binding pair.

20. The method according to claim 1, wherein the deposit of the second substrate at a single target site has a rounded shape and is identifiable in a two-dimensional field as a visually distinct dot.

21. The method according to claim 20, wherein the distinct dot is a dot having a diameter that is equal to or greater than around 0.4 micrometers.

22. The method according to claim 1, wherein the target is selected from a biological or chemical target molecule, a particle, a molecular or cellular complex, a molecular or cellular structure, a virus, a microorganism, and a fragment of a target molecule, particle, complex, structure, virus, or microorganism.

23. The method according to claim 22, wherein the target is a biological target molecule.

24. The method according to claim 1, wherein the individual unit of a target is selected from an individual single biological or chemical molecule, individual single particle, individual single molecular or cellular complex, individual single molecular or cellular structure, or individual single virus or microorganism, or individual single fragment of said molecule, particle, complex, structure, virus or microorganism.

25. The method according to claim 1, wherein the sample is a biological, chemical, or environmental sample.

26. The method according to claim 1, wherein the sample is a histological sample.

27. The method according to claim 1, wherein the target is a polypeptide or a nucleic acid molecule, or a fragment or a derivative of a polypeptide or a nucleic acid molecule.

28. The method according to claim 27, wherein the target is a cellular membrane receptor, a cytoplasmic protein, or a cytoplasmic nucleic acid.

29. A method of detecting at least one individual unit of an immobilized target in a sample, wherein the target is present in the sample over a broad dynamic concentration range, comprising:

a) incubating the sample with at least one first binding agent, wherein
   (1) the at least one first binding agent comprises a first enzyme with peroxidase or phenoloxidase activity; and
   (2) the at least one first binding agent is capable of specifically binding to an individual unit of the target, and forming at least one first target sites at a first fractional sub-population of the population of individual units of the target, wherein each first target site comprises a complex of one individual unit of the target and the at least one binding agent;

b) incubating the sample obtained in step a) in an aqueous solution (i) comprising a peroxide compound at a concentration in the range from 0.001 mM to less than 5 mM, a first substrate of the first enzyme, and a second substrate of the first enzyme,
   wherein the first substrate is 3, 3'-diambenzidine or a derivative thereof at a concentration in the range from 0.05 mM to 1 mM or another water soluble, electron rich compound which
   (1) forms a radical in the presence of the first enzyme; and
   (2) crosslinks molecules of the second substrate in the presence of the enzyme and the peroxide compound, thereby producing an insoluble polymer of the second substrate;
   and wherein the second substrate is at least one conjugate molecule comprising (i) at least two compounds that are capable of serving as substrates of the first enzyme, wherein at least one of the of the at least two compounds is a compound of the formula (II):

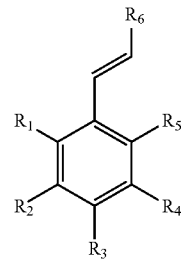

Formula II wherein
R₁ is —H, —O—X, —N(X)₂, or —S—X;
R₂ is —H, —O—X, —N(X)₂, or —S—X;
R₃ is —H, —OH, —NH₂, or —SH;
R₄ is —H, —O—X, —N(X)₂, or —S—X;
R₅ is —H, —O—X, —N(X)₂, or —S—X; and
R₆ is —CON(X)₂,
And X is H, alkyl, or aryl;
and (ii) a detectable label, wherein the detectable label is selected from the group consisting of a fluorescent or chromogenic matter or a member of a specific binding pair;
thereby forming a labeled discrete deposit of the second substrate at the at least one target sites;

c) incubating the sample obtained in step b) with a solution comprising hydrogen peroxide at a concentration sufficient to quench residual enzyme activity associated with the at least one first single target sites;

d) incubating the sample obtained in step c) with at least one second binding agent, wherein (1) the at least one second binding agent comprises a second enzyme with peroxidase or phenoloxidase activity; and
(2) the at least one second binding agent is capable of specifically binding to an individual unit of the target, thereby forming at least one second target sites at a second fractional sub-population of the population of individual units of the target, wherein each second target site comprises a complex of one individual unit of said second fractional sub-population and at least one second binding agent; and
e) incubating the sample obtained in step d) with a first substrate of the second enzyme, at least one second substrate of the second enzyme, and a peroxide compound, wherein the at least one second substrate of the second enzyme are each:
(1) a conjugate molecule comprising (i) at least two substrate groups that are each capable of serving as substrates of the second enzyme, and (ii) a detectable label; and
(2) capable of cross-linking to form an insoluble polymer;
and wherein the first substrate of the second enzyme is a water soluble, electron rich compound which
(1) forms a radical in the presence of the second enzyme; and
(2) cross-links molecules of the at least one second substrate of the second enzyme in the presence of the second enzyme and the peroxide compound, thereby producing an insoluble polymer of the second substrate of the second enzyme,
thereby forming a labeled discrete deposit of the second substrate of the second enzyme at least one of the second target sites;
f) detecting the labeled discrete deposit of the second substrate of the first enzyme at the first target sites as a first visually distinct dot, thereby detecting at least one unit of the first fractional sub-population of the target; and
g) detecting the labeled discrete deposit of the second substrate of the second enzyme at the second target sites as a second visually distinct dot, thereby detecting at least one unit of the second fractional sub-population of the target.

30. A method for detecting individual units of at least two immobilized targets present in a sample, comprising:
a) incubating the sample with at least one first binding agent capable of binding to a first target, wherein
(1) the at least one first binding agent comprises a first enzyme with peroxidase or phenoloxidase activity; and
(2) the at least one first binding agent is capable of specifically binding to an individual unit of the target, and forming at least one first target sites at a first fractional sub-population of the population of individual units of the target, wherein each first target site comprises a complex of one individual unit of the target and the at least one binding agent;
b) incubating the sample obtained in step a) in an aqueous solution (i) comprising a peroxide compound at a concentration in the range from 0.001 mM to less than 5 mM, a first substrate of the first enzyme and a second substrate of the first enzyme,
wherein the first substrate is 3, 3'-diaminobenzidine or a derivative thereof at a concentration in the range from 0.05 mM to 1 mM, or another water soluble, electron rich compound which (1) forms a radical in the presence of the first enzyme; and
(2) cross-links molecules of the second substrate in the presence of the enzyme and the peroxide compound, thereby producing an insoluble polymer of the second substrate;
and wherein the second substrate is at least one conjugate molecule comprising (i) at least two compounds that are capable of serving as substrates of the first enzyme, wherein at least one of the of the at least two compounds is a compound of the formula (II):

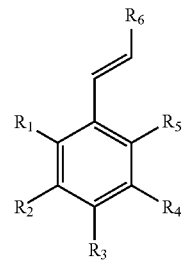

Formula II wherein
$R_1$ is —H, —O—X, —N(X)$_2$, or —S—X;
$R_2$ is —H, —O—X, —N(X)$_2$, or —S—X;
$R_3$ is —H, —OH, —NH$_2$ or —SH;
$R_4$ is —H, —O—X, —N(X)$_2$, or —S—X;
$R_5$ is —H, —O—X, —N(X)$_2$, or —S—X; and
$R_6$ is —CON(X)$_2$,
And X is H, alkyl, or aryl;
and (ii) a detectable label, wherein the detectable label is selected from the group consisting of a fluorescent or chromogenic matter or a member of a specific binding pair;
thereby forming a labeled discrete deposit of the second substrate at the at least one target sites;
c) incubating the sample obtained in step b) with a solution comprising hydrogen peroxide at a concentration sufficient to quench residual enzyme activity associated with the at least one first single target sites;
d) incubating the sample obtained in step c) with at least one second binding agent, wherein
(1) the at least one second binding agent comprises a second enzyme with peroxidase or phenoloxidase activity; and
(2) the at least one second binding agent is capable of specifically binding to an individual unit of the target, thereby forming at least one second target sites at a second fractional sub-population of the population of individual units of the target, wherein each second target site comprises a complex of one individual unit of said second fractional sub-population and at least one second binding agent; and
e) incubating the sample obtained in step d) with a first substrate of the second enzyme, at least one second substrate of the second enzyme, and a peroxide compound,
wherein the at least one second substrate of the second enzyme are each:
(1) a conjugate molecule comprising (i) at least two substrate groups that are each capable of serving as substrates of the second enzyme, and (ii) a detectable label; and (2) capable of cross-linking to form an insoluble polymer;

and wherein the first substrate of the second enzyme is a water soluble, electron rich compound which
  (1) forms a radical in the presence of the second enzyme; and
  (2) cross-links molecules of the at least one second substrate of the second enzyme in the presence of the second enzyme and the peroxide compound, thereby producing an insoluble polymer of the second substrate of the second enzyme, thereby forming a labeled discrete deposit of the second substrate of the second enzyme at least one of the second target sites;

f) detecting the labeled discrete deposit of the second substrate of the first enzyme at the first target sites as a first visually distinct dot, thereby detecting at least one unit of the target; and g) detecting of the labeled discrete deposit of the second substrate of the second enzyme at the second target sites as a second visually distinct dot, thereby detecting at least one unit of the second target.

\* \* \* \* \*